US011185418B2

(12) United States Patent
Lowry et al.

(10) Patent No.: US 11,185,418 B2
(45) Date of Patent: *Nov. 30, 2021

(54) TRANSCORPOREAL SPINAL DECOMPRESSION AND REPAIR SYSTEMS AND RELATED METHODS

(71) Applicant: GLOBUS MEDICAL, INC., Audubon, PA (US)

(72) Inventors: David Lowry, Holland, MI (US); Desmond O'Farrell, Grand Rapids, MI (US); Scott Tuinstra, Holland, MI (US); Roger Veldman, Hudsonville, MI (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,747

(22) Filed: Jun. 12, 2019

(65) Prior Publication Data

US 2019/0290445 A1 Sep. 26, 2019

Related U.S. Application Data

(63) Continuation of application No. 15/679,200, filed on Aug. 17, 2017, now Pat. No. 10,357,374, which is a
(Continued)

(51) Int. Cl.
*A61F 2/46* (2006.01)
*A61F 2/44* (2006.01)
*A61B 17/16* (2006.01)
*A61B 17/17* (2006.01)
*A61B 17/68* (2006.01)
*A61B 17/88* (2006.01)
(Continued)

(52) U.S. Cl.
CPC ............ *A61F 2/44* (2013.01); *A61B 17/1671* (2013.01); *A61B 17/1728* (2013.01); *A61B 17/1757* (2013.01); *A61B 17/686* (2013.01); *A61B 17/70* (2013.01); *A61B 17/88* (2013.01); *A61B 17/1637* (2013.01); *A61B 17/7059* (2013.01); *A61B 17/809* (2013.01); *A61B 2090/062* (2016.02); *A61F 2002/4649* (2013.01)

(58) Field of Classification Search
CPC ... A61B 17/88; A61B 17/1757; A61B 17/686; A61B 17/70; A61F 2/44
See application file for complete search history.

(56) References Cited

U.S. PATENT DOCUMENTS 5,766,253 A * 6/1998 Brosnahan, III ........ A61F 2/446
623/17.16
6,159,214 A * 12/2000 Michelson ........... A61B 17/025
606/80
(Continued)

*Primary Examiner* — Anu Ramana

(57) ABSTRACT

Bone plates for engaging bone members are described herein. The bone plates can receive one or more screws to secure the bone plates to an underlying bone member. The one or more screws can be inserted into bone plate holes that can be considered locking or non-locking. The bone plates described herein can have particular combinations of locking and/or non-locking holes. In addition, instruments such as distal and proximal aiming guides can accompany the bone plates to guide one or more screws into the bone plates.

19 Claims, 51 Drawing Sheets

Related U.S. Application Data continuation of application No. 13/874,273, filed on Apr. 30, 2013, now Pat. No. 9,763,801, which is a continuation of application No. 12/616,772, filed on Nov. 11, 2009, now Pat. No. 8,430,882, which is a continuation-in-part of application No. 12/210,089, filed on Sep. 12, 2008, now Pat. No. 8,323,320.

(60) Provisional application No. 60/972,192, filed on Sep. 13, 2007.

(51) Int. Cl.
*A61B 17/70* (2006.01)
*A61B 90/00* (2016.01)
*A61B 17/80* (2006.01)

(56) References Cited

U.S. PATENT DOCUMENTS 6,572,619 B2 * 6/2003 Santilli .............. A61B 17/1757
606/286
7,837,735 B2 * 11/2010 Malone .................. A61F 2/446
623/17.16

* cited by examiner

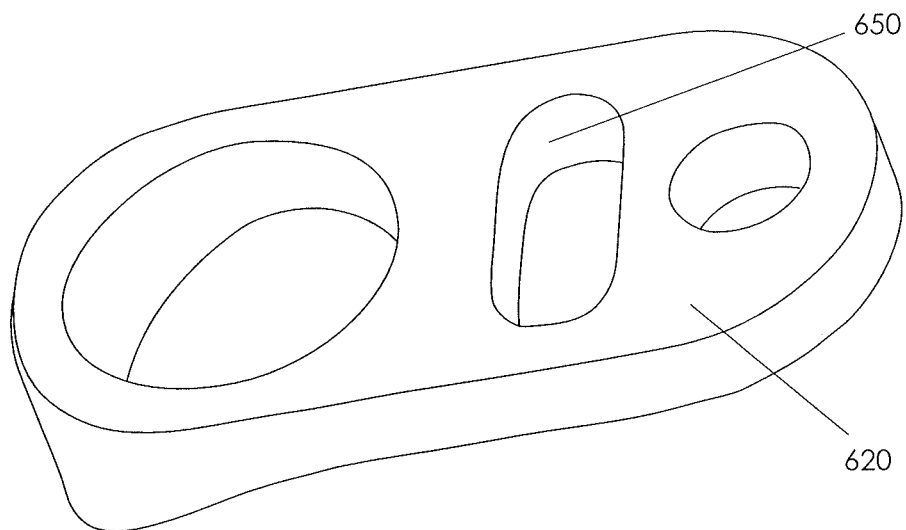
FIG. 17
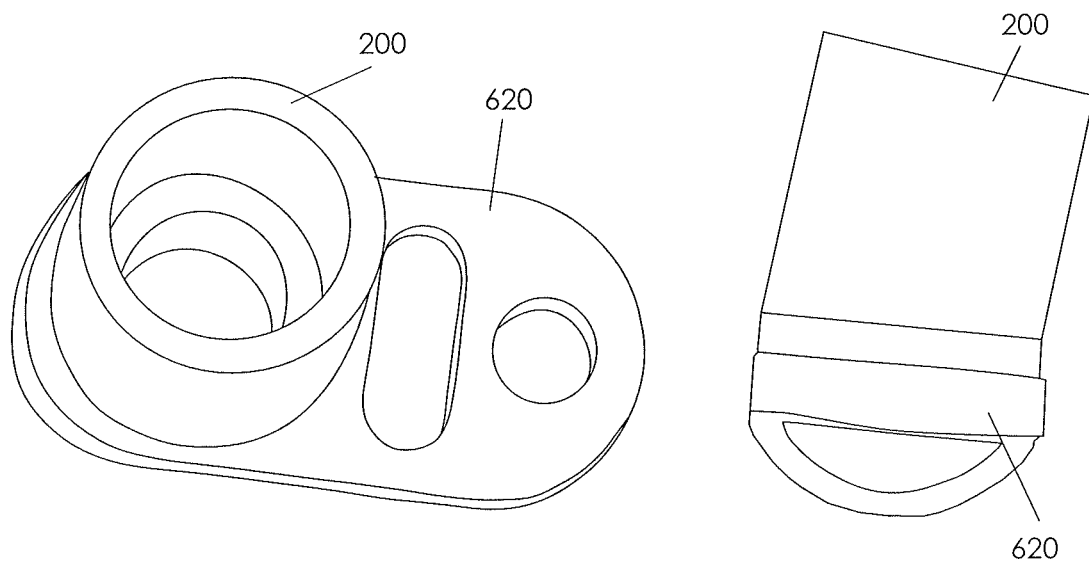
FIG. 18A
FIG. 18B

TRANSCORPOREAL SPINAL DECOMPRESSION AND REPAIR SYSTEMS AND RELATED METHODS

CROSS-REFERENCE TO RELATED APPLICATIONS

This application is a continuation of U.S. patent application Ser. No. 15/679,200 which is a continuation of U.S. patent application Ser. No. 13/874,273, filed Apr. 30, 2013, which is a continuation of U.S. patent application Ser. No. 12/616,772, filed Nov. 11, 2009, now issued as U.S. Pat. No. 8,430,882, which is a continuation-in-part of U.S. patent application Ser. No. 12/210,089, filed on Sep. 12, 2008, now issued as U.S. Pat. No. 8,323,320, which claims priority to U.S. Provisional Patent Application No. 60/972,192, filed on Sep. 13, 2007. All of these references are hereby incorporated by reference in their entireties.

FIELD OF THE INVENTION

The invention relates to devices and methods of spinal surgery. More particularly, the invention relates to systems and methods for creating and repairing a transcorporal access channel through a vertebral body.

INCORPORATION BY REFERENCE

All publications, patents and patent applications mentioned in this specification are herein incorporated by reference to the same extent as if each individual publication, patent or patent application was specifically and individually indicated to be incorporated by reference.

BACKGROUND

The performance of cervical discectomy, excision of tissue, and neural element decompression procedures have become standard neurosurgical approaches for the treatment of disorders of the spine and nervous system, as may be caused, for example, by disc degeneration, osteophytes, or tumors. The compressive pathologies impinge onto a neural element, causing a compression of nerve tissue that results in a symptomatic response such as loss of sensation or strength, occurrence of pain, or other related disorders. The majority of these procedures are performed with an anterior approach to the cervical spine. Disc and bone tissue are removed, a neural decompression is achieved, and a spinal repair procedure is performed.

The current conventional repair procedure includes a vertebral fusion in which a biocompatible implant is inserted and secured between the affected adjacent vertebrae. A bone plate is then is rigidly attached to the two vertebrae adjacent to the implant, immobilizing these vertebral segments and preventing the expulsion of the implant from the intervertebral space. Subsequently, osteogenesis of the vertebrae into the implant occurs, and ultimately the adjacent vertebrae fuse into a single bone mass. The fusion of the vertebral segments, however, can lead to problematic results. For example, the immobility of the fused vertebral joint is commonly associated with the progressive degeneration of the adjacent segments, which, in turn, can lead to degeneration of the intervertebral discs on either side of the fused joint.

Implantation of an artificial disc device offers an alternate approach to vertebral fusion. The objective of the artificial disc device is to preserve the relative motion of the vertebrae across the joint and to restore normal articulating function to the spinal column. In spite of the benefits that these procedures have brought to patients, both fusion and disc replacement have inherent problems. The surgeries are extensive, recovery time is relatively long, and there is often a loss of function, particularly with the use of fusion implants. The long-term biocompatibility, mechanical stability, and durability of replacement disc devices have not been well established. Further, there is no clinical consensus that the use of a replacement disc reduces the risk of adjacent segment degeneration.

Methods for surgery on the spine and cervical discs from an anterior approach were first developed in the 1950's, and a number of variations have been developed since then. Each anterior cervical discectomy procedure, however, has had to face the challenge represented by removing the tissue overlaying the compressing lesion (i.e., the herniated disc material, osteophyte or tumor) after having dissected through the soft tissue anterior to the spine. Early procedures exposed the compressing tissue by first making a cylindrical bone-and-disc defect in the spine centered on the disc space in sagittal and coronal planes, and generally following the plane of the disc itself. Later procedures made use of a rectangular, box-like defect in the disc space centered on the disc space and generally following the plane of the disc.

Procedures recently developed by Jho (referenced below) were motivated by the concern that procedures like those described above destroyed more of the natural disc tissue than was necessary to remove a laterally-positioned disc herniation or osteophyte (a bone spur). An alternative procedure, an uncovertebrectomy, was therefore developed that involved the removal of only the lateral-most aspect of the disc space, and the vertebral bone above and below it, which together comprise the entire uncovertebral joint. (See Choi et al., "Modified transcorporeal anterior cervical microforaminotomy for cervical radiculopathy: a technical note and early results", *Eur. Spine* 1 2007 Jan 3; Hong et al., "Comparison between transuncal approach and upper vertebral transcorporeal approach for unilateral cervical radiculopathy—a preliminary report", *Minim Invasive Spine Surgery*, 2006 October; 49 (5):296-301; and Jho et al., "Anterior microforaminotomy for treatment of cervical radiculopathy: part 1: disc-preserving functional cervical disc surgery", *Neurosurgery* 2002 November; 51 (5 Suppl.): S46-53.) This new type of procedure allows much of the disc space to remain untouched. While preserving more of the disc space and disc material than its predecessor procedures, the uncovertebrectomy nevertheless does obliterate the uncovertebral joint, and there is concern in the field regarding the eventual development of spinal instability at that disc level. Further, drilling bone at high speed adjacent to the nearby vertebral artery and sympathetic nerve process increases the concern of a higher risk of vertebral artery, secondary soft tissue injury, and Homer's Syndrome.

In another refinement of the uncovertebrectomy procedure, an anterior cervical microforamenotomy, the uncinate process and the lateral disc tissue may be left largely intact as a hole is drilled through the bone adjacent to the disc space near the uncinate process. In both uncovertebrectomy and anterior microforamenotomy, the exposure and decompression of the neural elements generally follow the plane of the disc space. While vertebral artery injury and spinal instability remain concerns with both procedures, the risk associated with anterior microforamenotomy is considered less than that of uncovertebrectomy.

An additional refinement of both uncovertebrectomy and anterior microforamenotomy is a transcorporeal decompression procedure (also referred to as an upper vertebral transcorporeal foramenotomy or a transcorporeal discectomy) may have advantages. This procedure differs from its disc space-preserving precedent procedures in several ways. First, the axis of the access hole drilled to expose the compressing pathology (e.g., herniated disc fragment) does not parallel the plane of the disc, but instead entirely avoids the disc space plane anteriorly and captures the disc only at its most posterior aspect. Second, while uncovertebrectomy and anterior cervical microforamenotomy are applicable only to lateral pathology, the transcorporeal decompression is potentially applicable to compressing pathology located laterally in the disc space region, bilaterally, or in the midline. Further, the procedure is performed from a substantially medial position on the vertebra assuring maximal distance from the vertebral artery and other sensitive soft tissue and thereby minimizing the risk of accidental injury.

Multiple technical challenges remain, however, in optimizing the transcorporeal cervical decompression procedure for general surgical use. First, manually orienting and controlling a hand-held cutting tool to make an access channel is a subjective and error-prone procedure. The target pathology is wholly behind and/or within the bony structure of the vertebra and is not visible in any way when approached from a traditional anterior approach to the cervical spine. As the channel is essentially being driven blindly, it can easily fail to capture the targeted pathology being within the range of the posterior opening of the access channel. Consequently the surgeon needs to prolong the procedure, and explore the space by excising tissue until the pathology is found. The exploration typically leads to the access channel becoming larger than necessary and undesirably irregular, thus putting surrounding bone at risk of fracturing during or after the procedure. Given the proximity of many target pathologies to the uncovertebral joint and the vertebral artery, it is likely that exploration of the space will lead to removal of the stabilizing bone and disc tissue. This tissue damage or loss can cause spinal instability, and may further result in accidental perforation of the vertebral artery.

Second, a manual drilling process increases the risk of over penetration into the spinal canal, with highly undesirable consequences.

Third, the posterior longitudinal ligament, once exposed in the access channel, can be difficult to open. The objective is to remove the ligament cleanly from the access channel area so as to provide unobstructed visualization of the compressed neural tissue. Current surgical techniques are subjective and time-consuming, often producing a shredding of the ligament within the access channel rather than its removal therefrom, thereby impeding the visualization of the underlying target pathology or dura mater protective layer.

Fourth, currently available microsurgical instruments are not well-suited for retrieving the herniated disc or bone fragments that may be found deep to the posterior longitudinal ligament.

Fifth, after the decompression is complete, the present solutions for filling the void remaining in the vertebra are not completely satisfactory. Demineralized bone matrix putties or similar materials can fill the defect but they offer no resistance to the normal compressing or torsional forces until calcification occurs. Such materials may also impose a new source of compression on the exposed neural structures if too much putty is applied or if the vertebra deforms or sustains a compression fracture subsequently because of the absence of an implant that sufficiently resists compressive forces.

Sixth, after a solid implant plug is placed in the surgically-formed access channel, there is presently no anterior cervical plate suited to preventing its outward migration. Currently available anterior cervical plates are designed to be placed across two or more adjacent vertebrae at or near the midline, not laterally, as would be needed for lateral compressing lesions. Existing plates also are designed as motion-restriction or motion-prevention devices to be placed bridging across a disc space rather than onto a single vertebral body, consequently they are too large and are counterproductive in the application such as that described above where the objective is to preserve the articulation and relative motion of the adjacent vertebrae.

Accordingly, there is a need for a system and method whereby any compressing spinal pathology may be removed or moved so as to decompress the neural elements involved while desirably also (1) preserving native disc and bone tissue and the natural motion of the spine with natural disc material, (2) minimizing the risk of injury to the vertebral artery, (3) minimizing the risk of structural spinal instability, (4) minimizing the risk of an inadequate decompression, (5) minimizing the risk of injury to the protective dura mater layer, (6) minimizing the risk of post operative bleeding and/or (7) minimizing the risk of a subsequent vertebral body fracture due to an unrepaired defect within it.

SUMMARY OF THE DISCLOSURE

The invention relates to a system and method for forming and repairing an access channel through a vertebral body, typically a cervical vertebral body, for the purpose of gaining access to a site in need of a medical intervention. In its formation, the channel originates on the anterior surface of the vertebral body, and it then provides access from the anterior approach. The channel follows a prescribed trajectory to a prescribed exit on the posterior surface of the vertebral body, and provides an opening at the site of sufficient size to address the medical need. The access channel is typically formed in cervical vertebral bodies. The nature of the medical need typically includes the need for a decompression procedure, as may occur as a result of a problematic portion or the whole of a herniated disc, an osteophyte, a thickened ligament, a tumor, a hematoma, a degenerative cyst, or any other compressing pathology. The medical intervention may be as minimal as observing the site, or performing exploration, or it may include a diagnostic procedure, or delivering a therapy, or it may include a surgery. A typical surgery performed through the access channel can include decompressing a neural element, such an individual nerve root, a spinal cord, or a cauda equina.

The system of the invention may further include an implantable bone repair device having an external geometry complementary to the internal geometry of the access channel, and a method for repairing or healing the channel by implanting such device. Some embodiments of the device include materials that are biocompatible, biologically absorbable, or any material known to be able to substitute for bone, and to be able to be stably and effectively integrated into bone. The device may further include as well as biologically active agents, such as osteogenic agents, that promote healing of the wound represented by the access channel, and fusion of the device such that it integrates into the vertebral body.

In some embodiments, the implantable bone repair device includes an assembly with a porous body that includes actual bone tissue. Such bone tissue may be provided by the bone removed during the formation of the channel itself, or it may come from another site from the patient as an autologous graft, or it may be provided by a separate donor.

The system to form and repair an access channel includes a bone cutting tool with a cutting element, a bone plate configured to be secured to the anterior surface of the vertebral body and having an opening sized to receive the cutting element; and a trajectory control sleeve configured to detachably engage the bone plate and having a cylinder configured to receive the cutting element. The bone plate and the trajectory control sleeve, when mutually engaged, are configured to cooperate to guide the cutting element to form the access channel with a prescribed trajectory from the anterior entry to the prescribed posterior opening.

Embodiments of a method for prescribing of the point of anterior entry and the channel trajectory toward the posterior opening are typically provided by a physician who observes the cervical spine of the patient radiographically. From such observation of patient anatomy and the site of pathological interest, the physician prescribes a trajectory according to a cranio-caudal axis and a medial lateral axis with respect to a point of entry on the anterior surface of vertebral body. Such radiographic observation may occur before the attachment of the bone plate, to be summarized below, and/or after the attachment of the bone plate.

Returning to summarizing the system for forming the access channel, some embodiments include fixation elements to secure the bone to the anterior surface of the vertebral body. The bone plate may include openings to accommodate fixation elements to secure the bone plate to the anterior surface of the vertebral body. In some embodiments, the bone plate and fixation elements are configured of a biocompatible material. In some embodiments, the bone plate and the fixation elements have a composition and structure of sufficient strength that that the bone plate may be permanently implanted.

Embodiments of the trajectory control sleeve may be configured to direct the bone cutting tool on a trajectory prescribed by the method above, the prescribed trajectory being an angle according to a cranio-caudal axis and a medial lateral axis with respect to a reference plane tangential to the access channel entry on the anterior surface of vertebral body.

Embodiments of the bone plate provide a reference plane such that the trajectory control sleeve, when secured to the bone plate, may be configured with a range of angles formed on two axes with respect to the plane of the bone plate, a cranio-caudal axis and a medial lateral axis, the range of the angles varying between about 1 degree and about 30 degrees from an angle perpendicular to the plate. In typical embodiments, the range of the angles varies between about 10 degrees and about 30 degrees from the perpendicular angle. In some embodiments, the system includes a plurality of trajectory control sleeves, the sleeves varying in regard to angles formed with respect to a plane represented by the bone plate when secured thereto, the angles ranging between about 10 degrees and about 30 degrees cranio-caudally from a perpendicular angle.

In some embodiments, the trajectory control sleeve and the bone plate have mutually-engageable features that orient the engagement of the trajectory control sleeve on the bone plate in a configuration that allows the trajectory control sleeve to guide the cutting tool into the vertebral body with the prescribed trajectory. And in some embodiments, the trajectory control sleeve includes a contact surface for engaging a corresponding surface on the bone cutting tool, the surfaces configured so as to limit the penetration of the cutting tool into the vertebral body to a prescribed depth.

In some embodiments, the posterior surface of the bone plate includes one or more penetrating elements configured to impinge into the vertebral bone tissue to improve fixation and resist the torsional forces associated with bone cutting procedures. In some embodiments, the bone plate includes an anatomically-orienting feature to establish the position of the bone plate relative to the medial centerline of the vertebral body. In some embodiments, the bone plate includes a biocompatible material. And in some embodiments, at least a posterior surface of the bone plate is of sufficiently porous composition to support in-growth of bone.

In various embodiments, the bone-cutting tool is any of a drill, a reamer, a burr, or cylindrical cutting tool, such as a core cutter or a trephine. In some of these embodiments, the cutting element of the bone-cutting tool has a cutting diameter of between about 5 mm and about 7 mm.

As noted above, embodiments of the implantable bone repair device have an external geometry complementary to the internal geometry of the access channel. These bone repair device embodiments may be sized to be insertable through an opening of the bone plate, the opening also being sized to receive the bone cutting element. In some embodiments, the bone repair device includes an abutting surface configured to engage a corresponding surface of the bone plate through which it is implanted, the engagement of these surfaces adapted to prevent the bone repair device from penetrating too deeply into or through the access channel of the vertebral body. In some embodiments, the bone repair device includes receiving features in or on its anterior surface configured to accommodate the attachment of an insertion tool.

In some of these embodiments, bone repair device and the bone plate have mutually engageable orientation and locking features. In various embodiments, the locking engagement results from the application of an axial force to snap the locking feature into a corresponding retaining feature of the bone plate. In other embodiments, the locking engagement results from the application of a torsional force to engage the locking feature into a corresponding retaining feature in or on the bone plate.

In some embodiments of the surgical system the bone repair device comprises a porous cage with a porosity sufficient to permit through movement of biological fluids, such as blood, and bone cells. The composition of the porous cage portion of the device may include any of a polymer, a metal, a metallic alloy, or a ceramic. An exemplary polymer may polyetheretherketone (PEEK), which may be present in the form of PEEK-reinforced carbon fiber, or hydroxyapatite-reinforced PEEK. In some embodiments of the bone repair device with a porous cage, the porous cage device includes a closeable opening through which harvested bone material (such a native bone from the access channel site) may be passed. And in some of these embodiments, the porous cage device includes a closeable cap configured to increase pressure on the harvested bone within the cage as the cap is closed. Further, some embodiments include an internal element adapted to enhance compressive force applied to the contents of the porous cage upon application of compressive force to the cage, such force inducing extrusion of harvested bone and blood from within the cage through its porous structure to the external surfaces of the cage.

Some embodiments of the surgical system include a trajectory and depth visualization device. In some of these embodiments, the trajectory and depth visualization device includes a radio-reflective feature so as to confirm the location of the bone plate device on the appropriate vertebral body and to facilitate the extrapolation of the projected trajectory of the bone cutting tool using a radiographic image. In some embodiments, the trajectory and depth visualization device includes visual markings to indicate the distance from the point of contact with the vertebral body and cutter penetration control feature on the bone cutter guide device.

A method for performing a procedure through a vertebral body overlaying a site in need of a medical procedure includes attaching the bone plate on the anterior surface of the vertebral body, engaging the trajectory control sleeve to the bone plate, inserting a bone cutting tool through the trajectory control sleeve, and forming an access channel body by removing bone with the bone cutting tool (the channel having a centerline co-incident with the centerline of the trajectory control sleeve through the vertebral), disengaging the trajectory control sleeve from the bone plate, and performing the medical procedure through the open space provided by the access channel and the opening on the posterior surface of the vertebral body.

The access channel follows a prescribed trajectory from an anterior entry point to a prescribed opening on a posterior surface of the vertebral body in the locale of the site in need of the medical procedure. The prescription for the points of entry and exit and the vectors of the access channel are determined by radiographic observations and measurements, as summarized above. In some embodiments of the method, forming the access channel includes forming the channel with a constant, circular cross-section along a single, straight axis aligned with the trajectory control sleeve.

Before engaging the trajectory control sleeve to the bone plate, the method may include selecting the sleeve to be used in the procedure such that when the sleeve and the bone plate are engaged, the sleeve has an angular orientation relative to the bone plate that is consistent with the prescribed trajectory of the access channel. Further, before attaching the bone plate to an anterior vertebral surface, the method may include exposing one or more vertebral bodies in a spinal column by anterior incision. Further still, after performing the medical procedure, the method may include leaving the bone plate attached to the vertebral body.

In some embodiments of the method, after engaging the trajectory control sleeve to the bone plate, the method may include inserting a radiopaque locating device into the trajectory control sleeve device, radiographically observing the locating device and determining therefrom an extrapolated trajectory of the access channel toward the posterior surface of the vertebral body, and verifying that the extrapolated trajectory is consistent with the prescribed trajectory such that the point of exit at the posterior surface is proximal to the targeted site of interest.

In some embodiments of the method, after engaging the trajectory control sleeve to the bone plate, the method may include inserting a depth-measuring device into the trajectory control sleeve device to establish an optimal depth of penetration of the bone-cutting tool into the vertebral body, the depth being influenced by the disposition of the bone plate against a variable topography of the anterior surface of the vertebral body.

In some embodiments, after the completing the medical procedure through the access channel, the method further includes repairing the access channel with an implantable bone repair device, the device having an external geometry complementary to the internal geometry of the channel. In typical embodiment of the method, repairing the access channel includes implanting the bone repair device through the bone plate and into the channel. And in some of these embodiments, the method includes securing a proximal portion of the bone repair device to the bone plate.

In some embodiments of the method, repairing the access channel includes in-growing bone from the vertebral body into at least a portion of the surface of the bone repair device. And in some embodiments, repairing the access channel includes stimulating bone growth within the bone repair device by providing an osteogenic agent within the repair device.

In some embodiments of the method, repairing the access channel includes placing a portion of harvested native bone tissue within a bone repair device that comprises a porous cage. In these embodiments, the method may further include allowing or promoting intimate contact between the bone tissue within the bone repair device and bone tissue of the vertebral body. The method may further include perfusing at least some bone tissue or bone-associated biological fluid from the bone repair device into the vertebral body. Still further, the method may include healing together the harvested native bone tissue within the bone repair device and bone tissue of the vertebral body.

In some embodiments of the system, the bone plate and the trajectory control sleeve are an integrated or integrally-formed device. In this embodiment, thus the system includes a bone cutting tool with a cutting element and an integrated device comprising a bone plate portion and trajectory control sleeve portion. The bone plate portion is configured to be secured to an anterior surface of the vertebral body and has an opening sized to receive the cutting element. The trajectory control sleeve portion has a cylinder configured to receive the cutting element of the bone cutting tool, and the integrated device is configured to guide the bone cutting tool to form the access channel with a prescribed trajectory from the anterior entry to the prescribed posterior opening.

A method for performing a procedure through a vertebral body overlaying a site in need of a medical procedure with the integrated device summarized above includes attaching the integrated device on an anterior surface of the vertebral body, inserting a bone cutting tool through the trajectory control sleeve portion of the device, forming an access channel through the vertebral body by removing bone with the bone cutting tool, the access channel prescribed as summarized above, disengaging the integrated device from the bone plate, and performing the medical procedure through the access channel and the opening on the posterior surface of the vertebral body.

In some embodiments of the system and method, the bone plate or integrally formed bone plate portion does not lie directly over the anterior entry location for the access channel. Rather, the bone plate or bone plate portion is attached to the anterior surface of the vertebral body adjacent to the entry location, and supports a trajectory control sleeve or sleeve portion which may be located adjacent to the entry location.

BRIEF DESCRIPTION OF THE FIGURES

FIG. 3A shows a trajectory control sleeve in a side view.

FIG. 3B provides a side cross-sectional view of the trajectory control sleeve, showing how the angle of the sleeve relative to its base forms an asymmetrical opening in the base.

FIG. 9A is a perspective view of a trajectory pin and a drill depth gauge assembled together FIG. 9B is a perspective view of an embodiment of the depth gauge sub-assembly.

FIG. 17 is an anterior perspective view of an alternate embodiment of an implantable bone plate.

FIGS. 18A and 18B are views of the trajectory control sleeve mounted on the bone plate embodiment of FIG. 17. FIG. 18A shows the trajectory control sleeve and bone plate from distally directed perspective.

FIG. 18B shows the trajectory control sleeve and bone plate from a side view.

FIG. 23 shows the repair device being held by a surgeon immediately prior to inserting into the access channel.

FIG. 24 shows the surgeon's finger pressing the repair device through the bone plate and into the access channel.

FIG. 25A shows the device from a proximally-directed perspective.

FIG. 25B shows the device of FIG. 25A from a distally-directed perspective.

FIG. 26A shows the device from a side view.

FIG. 26B shows the device of FIG. 26A from a proximally-directed perspective.

FIG. 27A shows the device from a proximally-directed perspective.

FIG. 27B shows the device of FIG. 27A from a distally-directed perspective.

DETAILED DESCRIPTION

Figure 1:
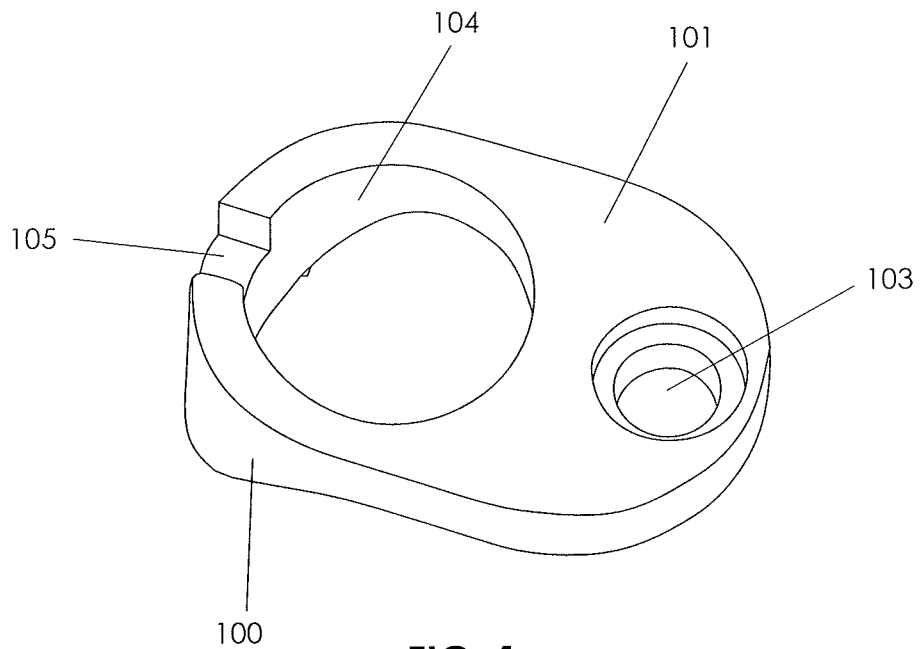
FIG. 1 is a view of an implantable bone plate device viewed from an anterior perspective.

An inventive surgical system and associated method of use are provided for transcorporeal spinal procedures that create and use an anterior approach to an area in need of surgical intervention, particularly areas at or near a site of neural decompression. Removal or movement of a source of compressing neural pathology is achieved via a surgical access channel created through a single vertebral body instead of through a disc space or through an uncovertebral joint (involving 1 or 2 vertebrae). The access channel has a specifically prescribed trajectory and geometry that places the channel aperture at the posterior aspect of the vertebra in at or immediately adjacent to the targeted compressing pathology, thus allowing the compressing neural pathology to be accessed, and removed or manipulated. The access channel is formed with precise control of its depth and perimeter, and with dimensions and a surface contouring adapted to receive surgical instruments and an implanted bone repair device.

The channel may be used to access and operate on the compressing pathology, more particularly to remove or to move a portion or the whole of a herniated disc, an osteophyte, a thickened ligament, a tumor, a hematoma, a degenerative cyst, or any other compressing pathology. As a part of the procedure, the posterior longitudinal ligament posterior to the transcorporeal access channel may be opened or removed through the access channel, thereby permitting the visualization or removal of any compressing pathology otherwise obscured by the ligament.

In some embodiments, the invention preserves native bone and disc tissue that is sacrificed by prior art procedures, and further preserves the natural motion of the vertebral joint. The procedure also preserves at least the anterior half of the vertebral endplate of the vertebral body upon which the cutting occurs. Removal or the movement of the compressing pathology can proceed even when a portion of the compressing pathology resides beyond the limits of the transcorporeal access channel. Further, removal of the compressing pathology may occur without inducing posterior or inward compression on the dura mater protective layer surrounding the spinal cord and exiting nerve roots, or exerting direct pressure on the spinal cord or exiting nerve roots. Also, the compressing pathology removal may occur without lacerating the dura mater protective layer surrounding the spinal cord and exiting nerve roots.

Embodiments of the system and method also pertain to therapeutic occupation and repair of the vertebral body void created by making such an access channel. This repair is achieved by inserting an implantable vertebral repair device that has a conformation complimentary to the internal geometry of the access channel after the procedure is complete, and by securing the implant in the inserted position by means of a vertebral bone plate. The external surface of the vertebral repair device is in substantial contact with the internal surface of the access channel after insertion is complete, thereby substantially restoring structural and mechanical properties of the vertebrae. Such repair occurs without directly or indirectly inducing compression of underlying dura mater or neural structures. The repair further occurs without the subsequent anterior migration of the vertebral repair device, which could cause injury to soft tissue structures located anterior to the spine.

In some embodiments, the implanted device has a bioabsorbable composition that allows replacement of the implant device by in-growth of native bone tissue, or which is incorporated into the native bone tissue. As a whole the system increases the objectivity of considerations associated with spinal surgery, reduces patient risk, and contributes to better and more predictable surgical outcomes.

Various aspects and features of the invention will now be described in the context of specific examples and with the illustrations provided by FIGS. 1-37.

Figure 28:
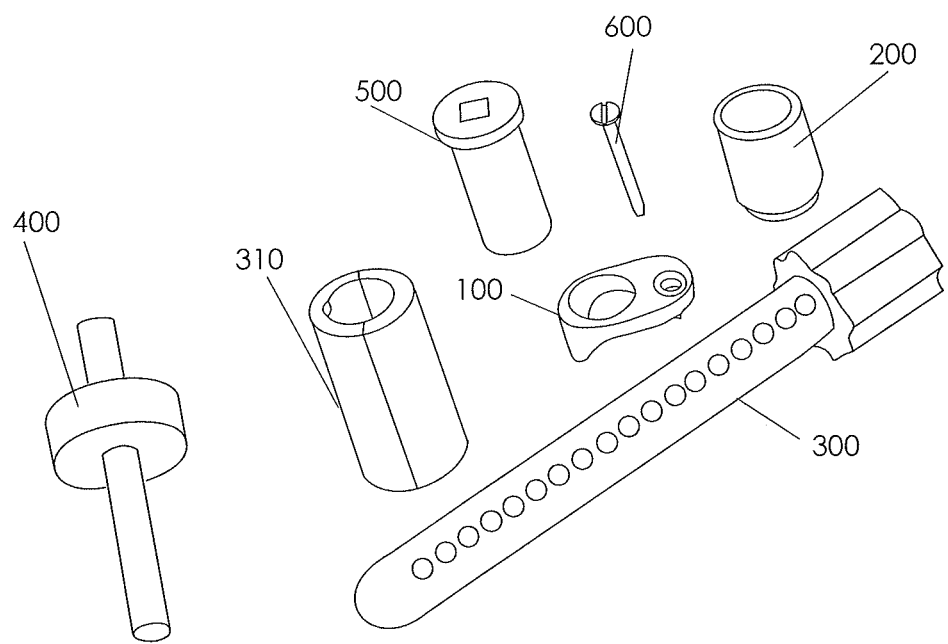
FIG. 28 shows the primary components of an exemplary system associated with the creation and repair of the intravertebral access channel.

A number of tools and instruments are included in or used within the system and methods described herein. FIG. 28 shows some of these system elements: an implantable vertebral plate 100, a cutting tool guide 200, a confirmation device or depth gauge 300, a collar 310 for the confirmation device, a cutting tool 400, an implantable device 500, and an implant locking device 600.

An implantable vertebral plate 100 is adapted to attach to the anterior surface of a vertebra. A trajectory control sleeve 200 is adapted to detachably mount the implanted bone plate 100 to establish the entry point, trajectory, and depth of an access channel created through the vertebral body. A confirmation device 300 is adapted to temporarily engage the cutter tool guide for the purposes of confirming placement of the trajectory control sleeve on the correct vertebra, for visualizing the projected trajectory of the bone cutting device, and for measuring the actual distance between the trajectory control sleeve and the anterior bone surface so as to accurately and predictably penetrate through the vertebra without impinging on the dura-mater or other neural tissue at the posterior aspect of the channel. The pin-shaped confirmation device 300 is typically radio-reflective or radiopaque, thus allowing confirmation of all geometries on a surgical radiograph taken prior to the excision of any tissue.

A cutting tool 400 is generally adapted to remove bone material and create the vertebral access channel; the tool 400 has the precise cutting geometry necessary to produce the prescribed access channel geometry within the vertebral bone. The access channel provides various forms of advantage for aspects of procedures as described further below.

A surgical cutting instrument is used to open or partially remove the posterior longitudinal ligament which can obscure a view of the pathology of interest, but becomes observable by way of the access channel. A cutting tool used to remove osteophytes (bone spurs) at or adjacent to the base of the vertebral body can be approached by way of the access channel proximal to the neural elements to be decompressed. An instrument for grasping or moving herniated disc material or other compressing pathology can be provided access to the site located at or near the base of the access channel.

An implantable bone repair device 500 is adapted repair the vacant vertebral volume created by the formation of the access channel.

An implant locking device 600 is adapted to retain the implant in the desired position. The locking device is adapted to positively engage the anterior surface of the repair implant and engagably lock it in place with respect to the implanted bone plate device 100. Fasteners such as elements 600 and 900 (seen in later figures) are applied to retain a bone plate or locking cap (see in other figures) in a desired position.

Each of these aforementioned system elements and their role in surgical procedures on the spine are described in further detail below.

Figure 2:
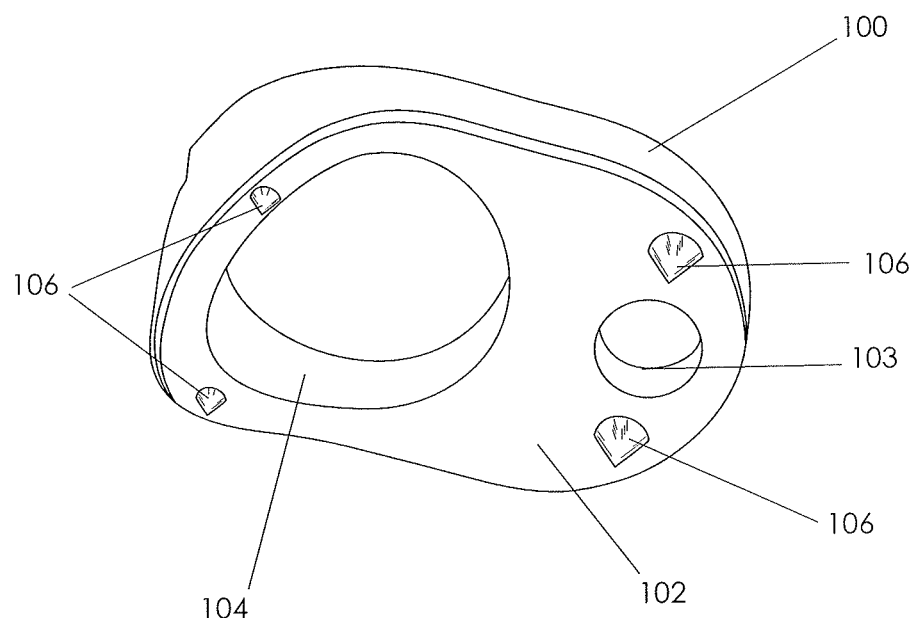
FIG. 2 is a view of an implantable bone plate device viewed from a posterior perspective.

FIGS. 1 and 2 show anterior and posterior views, respectively, of an implantable transcorporeal bone plate device 100 with a first or anterior facing surface 101 and a second or posterior facing surface 102, the posterior facing surface being configured to be proximal or in contact with the anterior surface of a vertebral body after implantation. The device further has one or more holes 103 that form an aperture between surfaces 101 and 102 to accommodate and secure retention screws there to secure the device 100 to vertebral bone.

Embodiments of implantable bone repair described and depicted herein are may include a multiple number of orifices, as for example, for inserting attachment elements, or for viewing, that have various sizes and typically are circular or ovular in form. These are merely exemplary forms and profiles of openings which may vary depending on particulars of the application of the device, such that size and profile may vary, and for example, by taking the form of any of circular, trapezoidal, multilateral, asymmetrical, or elongated openings.

The device also has a passage 104 for receiving and detachably-engaging a bone cutting guide device such as a drill or ream. The device 100 further may have one or more engaging features 105 configured to receive and engage a corresponding feature on the trajectory control sleeve in a manner that prevents relative motion of the trajectory control sleeve and its accidental disengagement from the implanted bone plate. The device may have one or more protrusions 106 on the posterior surface (FIG. 2), the protrusions being adapted to impinge into or through the cortical bone so as to increase the stability of the implant on the bone and to allow for temporary placement of the device prior to insertion of the bone screws through the opening 103. Protrusions 106 further act to stabilize the bone implant and to transfer loads around the vertebral access channel after a surgical procedure is complete, thereby further reducing the risk of bone fractures or repair device expulsion.

Figure 3A:
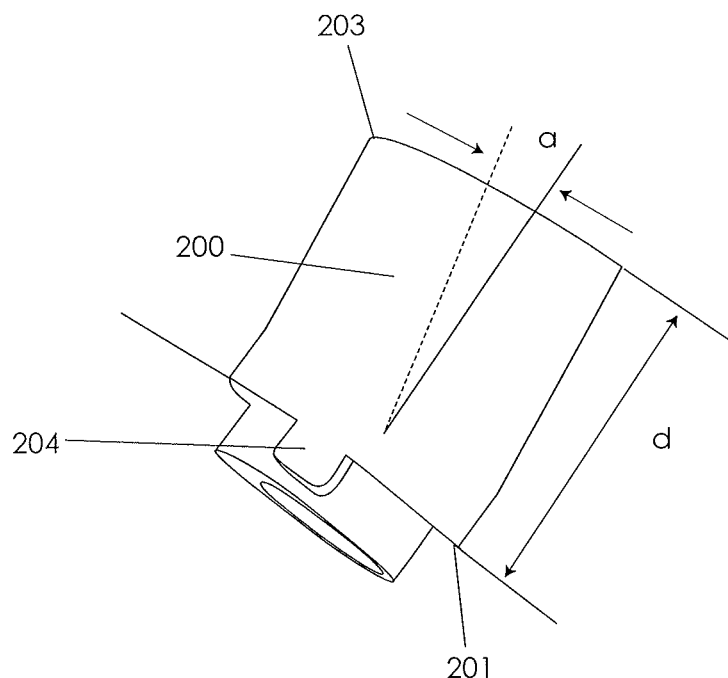
FIGS. 3A and 3B provide views of a trajectory control sleeve attachment.
Figure 3C:
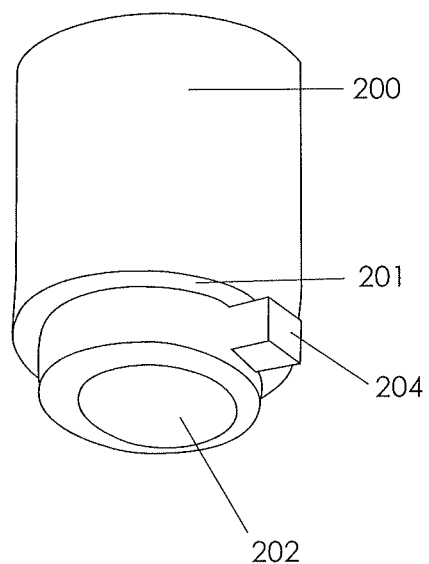
FIG. 3C shows the trajectory control sleeve from a proximally-directed perspective.
Figure 3B:
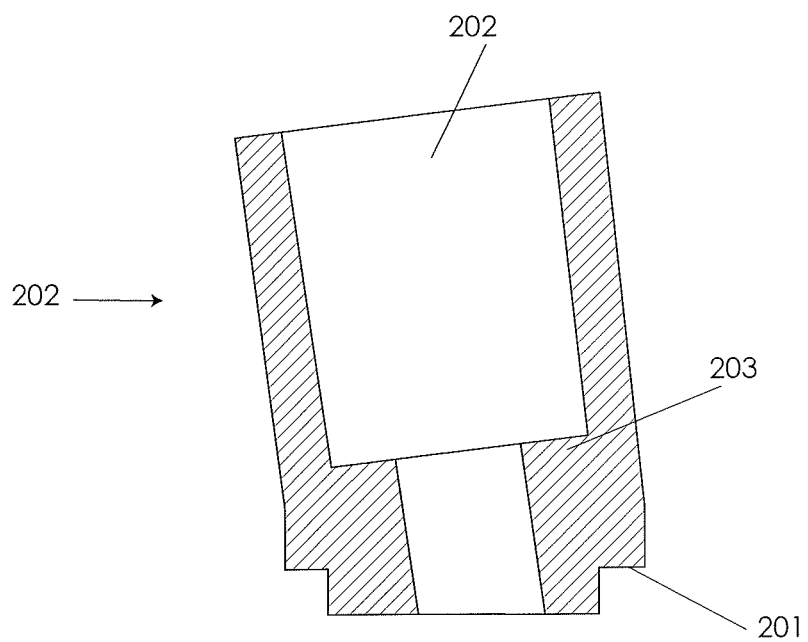

FIGS. 3A-3C show a side view and perspective view, respectively, of an embodiment of a trajectory control sleeve 200 for a bone cutting tool, a rotary cutting tool, for example, such as a drill, burr, reamer, or trephine. FIG. 3A shows a trajectory control sleeve in a side view, while FIG. 3C shows the trajectory control sleeve from a proximally-directed perspective. The trajectory control sleeve 200 has an internal cylinder 202 there through to allow passage of a bone-cutting tool, such as a drill or trephine, and to establish and control the angle α of penetration of the drill through a vertebral body. As seen in FIG. 3B the angle α refers to the angular difference from a right angle approach with respect to the plane formed by an implantable bone plate 100 to which the trajectory control sleeve is engaged. More specifically, angle α can represent a compound angle according to a cranio-caudal axis and a medial lateral axis with respect to a reference plane tangential (such as would be represented by an implanted bone plate) to the access channel entry on the anterior surface of vertebral body. The angle α is prescribed by a physician by making use of radiographic images of the spine that focus on the target vertebrae and the underlying pathology that are the subject of surgical or diagnostic interest. Such procedures are typically performed prior to surgery, and they may be repeated after the bone plate is attached to the surgical site. FIG. 3C provides a cross sectional view of an exemplary control sleeve 200, which shows the tilt of the annular ring 203 in accordance with angle α, and the consequent off-center opening at the base of the trajectory sleeve, which generally aligns with the base of the bone plate when the two components are engaged.

In some embodiments of the system and method, a transcorporal access channel is formed using a trephine type device such as those provided by Synthes, Inc (West Chester Pa.), which offers particular advantages. The trephine device produces a cylindrical channel through the vertebral bone while maintaining the core to be removed in an intact state. The core can be removed from the trephine after the tool itself has been removed from the vertebral body, and the bone tissue can be subsequently re-used as graft volume after the surgical procedure is completed.

Figure 4:
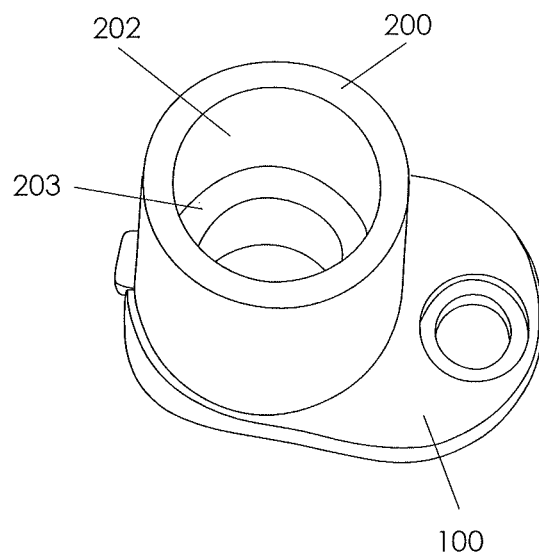
FIG. 4 is an anterior perspective of the trajectory control sleeve mounted to an implantable bone plate.

Trajectory control sleeve 200 has a surface 201 adapted to be in intimate contact with and be co-planar to an anterior facing surface 101 of a bone plate implant device 100 (after engaging the device, as in FIG. 4) so as to assure that the axial distance d is well established and controlled. The trajectory control sleeve 200 further has an annular abutting surface 203 surrounding the opening of the internal cylinder 202, the surface being adapted to positively engage a corresponding feature such as a flange or collar of the drill so as to prevent its over-penetration into the vertebral body. This abutment may be internal or external to the guide device as shown in FIG. 4 and FIG. 3A respectively. Trajectory control sleeve 200 also has an engaging and interlocking feature 204 adapted to detachably-engage a corresponding feature 105 (see FIG. 5) on the implantable bone plate 100. The trajectory control sleeve 200 is further generally adapted to protect surrounding vascular and soft tissue from accidental injury or cutting by providing a solid protective sheath around the sharp edges of the drill while it is operating.

Figure 5:
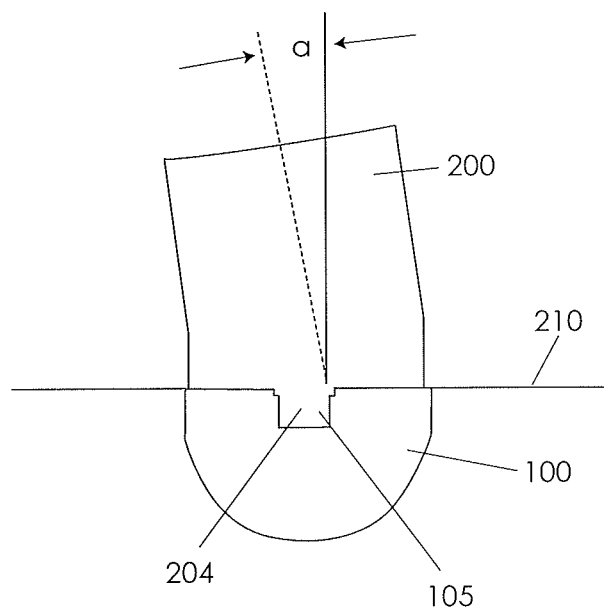
FIG. 5 is a lateral view of the trajectory control sleeve mounted to an implantable bone plate.

FIGS. 4 and 5 show a perspective view and side view, respectively, of trajectory control sleeve 200 and an implantable bone plate 100 in their mutually interlocked positions. FIG. 4 shows the internal cylinder 202 for providing access, guiding and controlling the penetration of a drill into vertebral bone. FIG. 4 further shows an alternate embodiment of the device that has an abutting surface 203, in which the abutting surface is internal to the trajectory control sleeve. FIG. 5 shows the planar engagement of the anterior surface of an implanted bone plate 101 with the corresponding surface 201 of the trajectory control sleeve. This engagement establishes a reference plane 210 from which angle α and distance d are controlled and referenced relative to the vertebral body. FIG. 5 further shows the engagement of the detachable locking features 205 of the trajectory control sleeve and of the bone plate 105.

Figure 6:
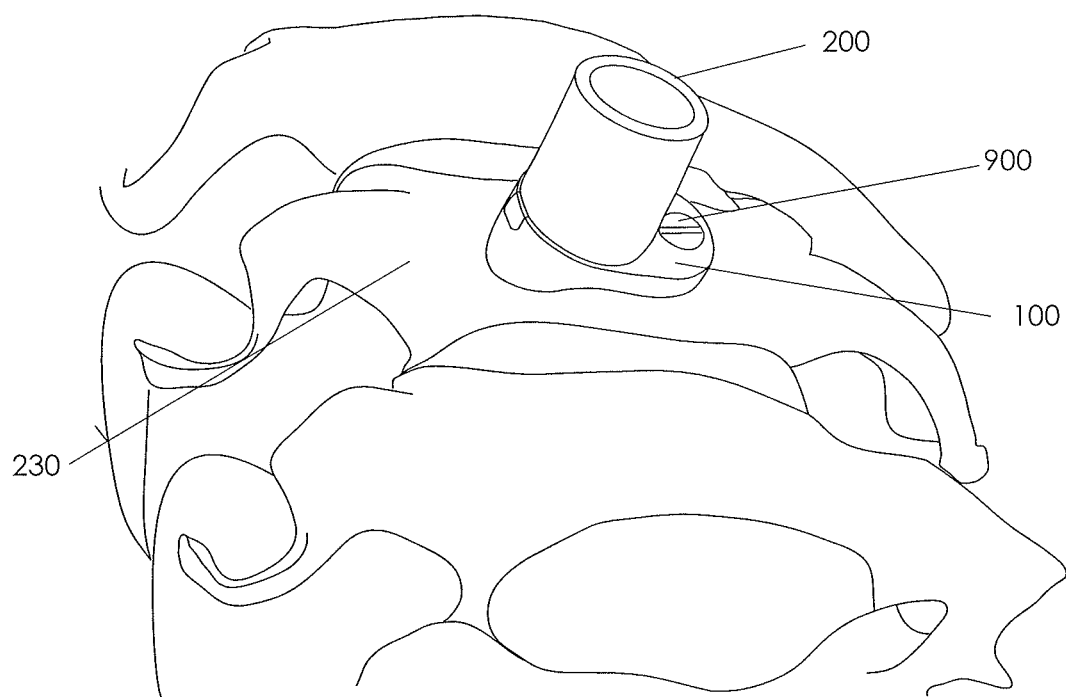
FIG. 6 is a perspective view showing an implanted bone plate screwed a vertebral body and with a trajectory control sleeve mounted thereon.
Figure 7:
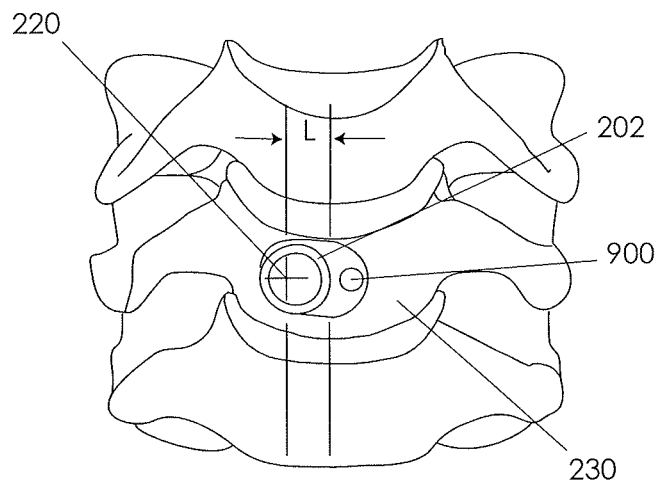
FIG. 7 is an anterior view showing an implanted bone plate screwed to a vertebral body and a trajectory control sleeve mounted thereon.
Figure 8:
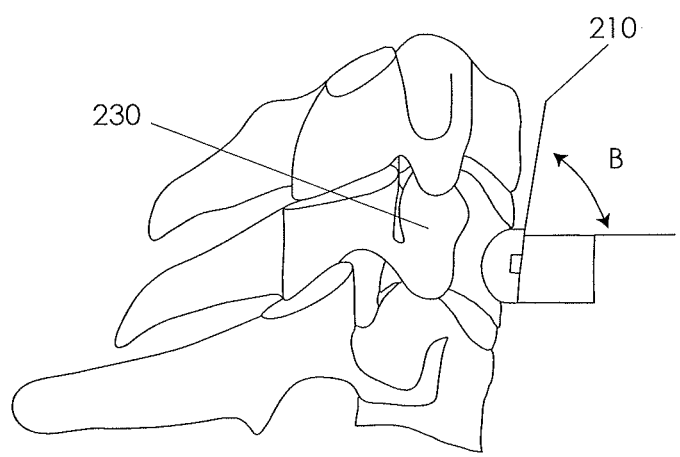
FIG. 8 is a lateral view showing an implanted bone plate screwed to a vertebral body and with a trajectory control sleeve mounted thereon.

FIGS. 6-8 relate to the placement of a mutually-engaged bone plate 100 and a trajectory control sleeve 200 to a vertebral body 230, in preparation for creating an access channel through the vertebral body. FIG. 6 provides a surface perspective view of bone plate 100 in an implanted position on a vertebral body 230, the plate secured by a bone screw 900, and further shows trajectory control sleeve 200 in its engaged position on the bone plate 100. FIG. 7 shows an anterior view of a bone plate 100 and trajectory control sleeve 200 mutually engaged and, the engaged assembly in it installed position on vertebral body 230. A bone screw 900 is inserted at or near the medial centerline 231 of the vertebral body 230, thus positioning the center point 220 of the trajectory control sleeve cylinder at a prescribed distance 1 from the centerline. As seen in FIG. 8, an angle β is the compliment to angle α shown in FIG. 5. After installation of the bone plate implant 100 on a vertebral body 230, the reference plane 210 may be delineated relative to the vertebral body 230 and as a baseline reference for the angle and depth of drill penetration into the vertebral body.

Figure 9A:
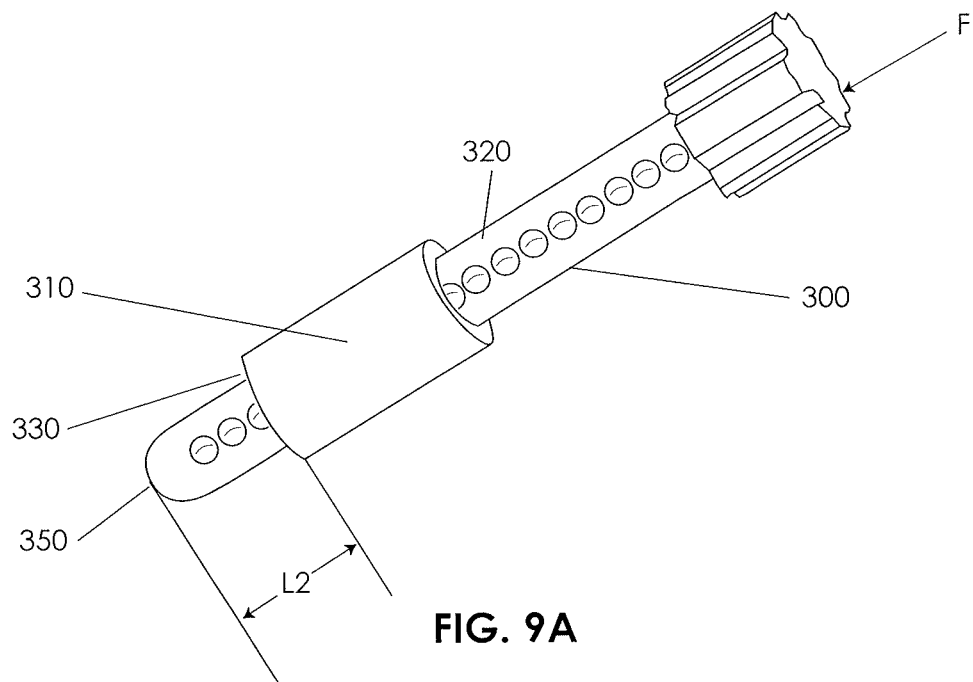
FIGS. 9A-9B show various views of a trajectory pin and a drill depth gauge.
Figure 9B:
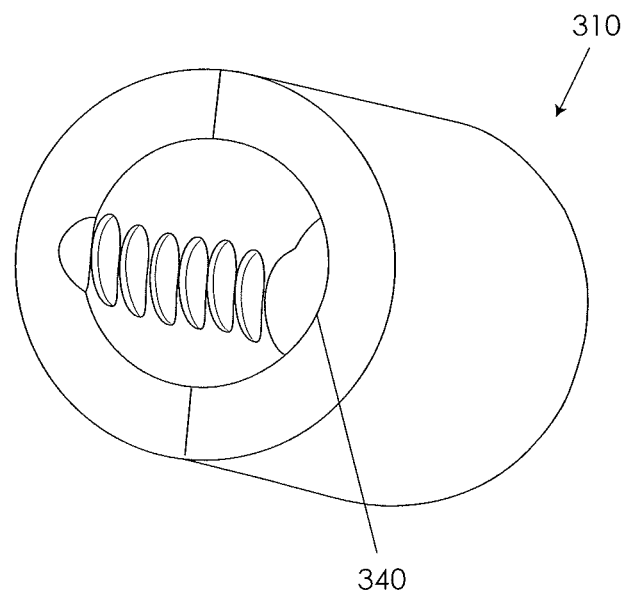

FIGS. 9A and 9B show a pin or plug type confirmation device 300 used for confirming vertebral position prior to excision of bone or other tissue and a collar 310 into which the confirmation device is inserted. A standard procedure in spinal surgery is to insert a radiographically reflective screw or pin into the vertebral body and to take an x-ray of the cervical spine prior to beginning any procedure so as to assure that the procedure is being performed at the correct vertebral level. In the embodiment described the confirmation device 300 is slidably inserted within the internal diameter of the control sleeve 200 and progressed axially therethrough until the proximal end of the device 300 is in contact with the anterior surface of the vertebral body. A radiographic image is taken inter-operatively and reviewed prior to the excision of any vertebral bone tissue. The examination includes an extrapolation of the trajectory through the vertebral body so as to confirm that the actual point of exit at the posterior surface of the vertebra is at the surgically prescribed location. Further, the axial distance from the both the anterior and/or posterior surfaces of the vertebra are measured and used as references to control the depth of bone cutting necessary to produce the access channel and to prevent over penetration into the dura mater or neural tissue. In some instances the device 300 may be used during the bone cutting procedure as a checking device to determine the actual progression of the channel across the vertebra.

FIG. 9B shows a trajectory confirmation pin 300 and a collar 310 that slidably-engages the external diameter of the pin by way of features 320 that engage complementary features 321 on the internal diameter of the collar. In this exemplary embodiment, the trajectory pin features 320 are convexities that are complementary to concave collar feature 321. Collar 310 can slide axially along the length of the pin diameter 320 and frictionally-engage the pin diameter in a manner that requires an axial force to be applied to the collar to induce axial movement. Collar 310 has a surface of engagement feature 330 that is adapted to make intimate contact with the annular surface 203 of the trajectory control sleeve when the pin is inserted into the trajectory control sleeve. Once surfaces 203 and 330 are engaged, insertion force F (FIG. 9A) applied by a surgeon causes pin 300 to travel axially through the internal diameter of collar 340, increasing the distance L2 between point 350 on the tip of the pin and the control surface 330 of the collar 310.

Figure 10:
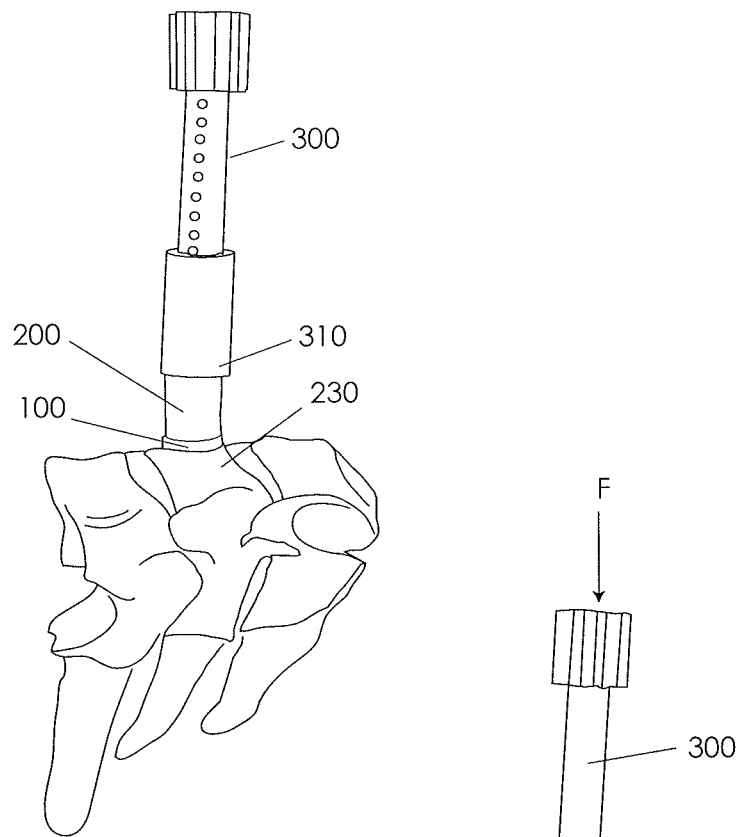
FIG. 10 is a lateral view of the trajectory pin assembly shown in FIG. 9A engaged in a trajectory control sleeve.
Figure 11:
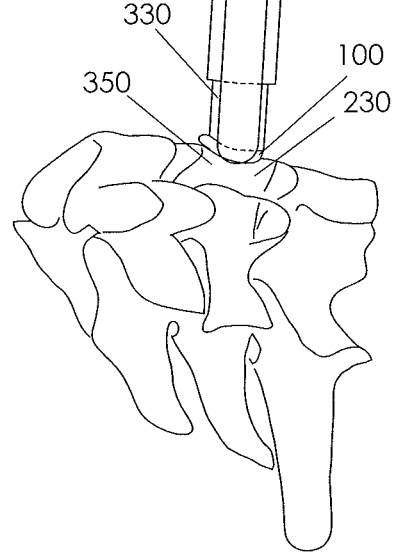
FIG. 11 is a cross sectional view showing a trajectory pin in full engagement with vertebral bone and a trajectory control sleeve.
Figure 12:
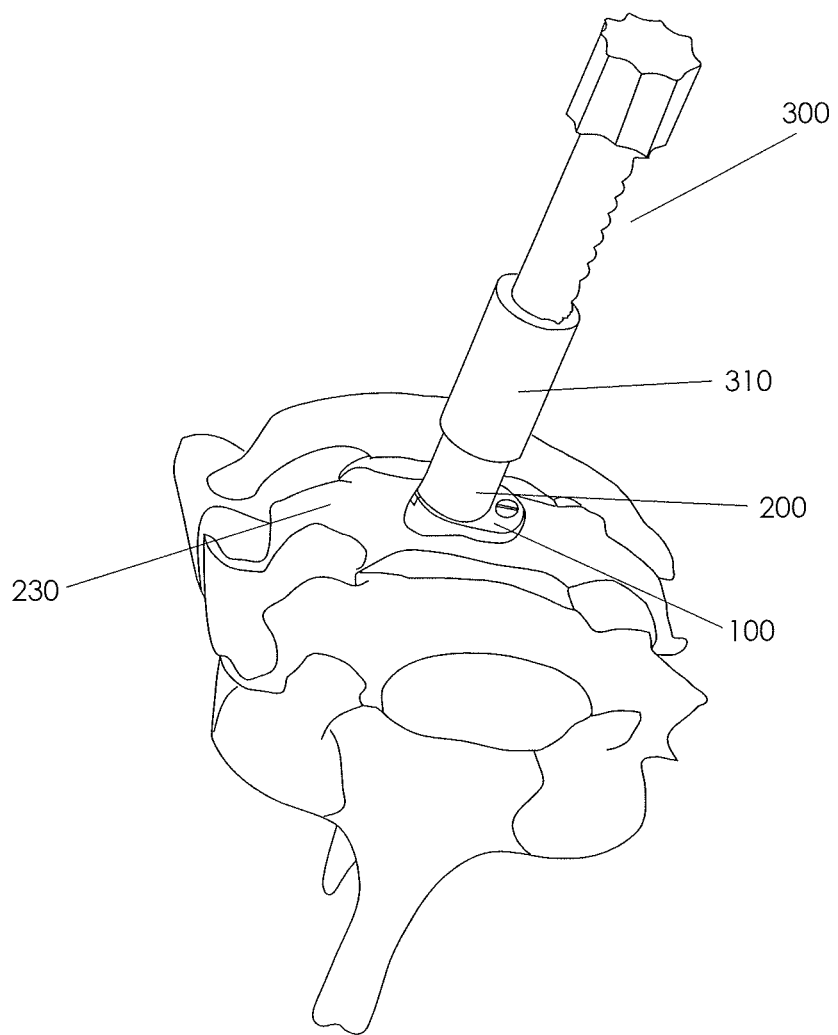
FIG. 12 is an anterior perspective view of a trajectory pin and depth gauge engaged within a trajectory control sleeve.

FIGS. 10-12 relate to the use of a trajectory confirmation pin 300, a collar 310, and trajectory control sleeve 200 in the context of a bone plate 100 in place, as implanted in a vertebral body 230. An embodiment of a pin device 300 is temporarily inserted into the internal cylinder of the trajectory control sleeve 200 and an x-ray is taken. The x-ray confirms the location of the vertebral body 230 and an anterior-to-posterior extrapolation along the centerline of the device through the image of vertebral body indicates the trajectory of the drill or cutting tool and the projected point of exit at or near the posterior longitudinal ligament. Angular and distance measurements may be made using the radiograph, and if adjustments are required, the surgeon disengages the trajectory control sleeve and installs another device with the desired geometry.

FIG. 11 shows the confirmation pin 300 at its maximum depth of penetration through the transparently rendered trajectory control sleeve 200 and bone plate implant 100. In this position, tip 350 of the pin device is in intimate contact with the surface of the vertebral bone 230. Because of the mechanical engagement of the collar 310 on the external surface, the collar remains in position relative the bone-contacting tip of the pin 350. Upon removal of the pin, distance L2 (see FIG. 9A), as measured between the collar surface 330 and the pin contact tip 350, provides a reference dimension with which the penetrating depth of the bone drill can be controlled by setting a mechanical stop that engages the annular surface 203 of the trajectory control sleeve. For ease of use, the surface of the confirmation pin 300 may have linear graduations.

Figure 13:
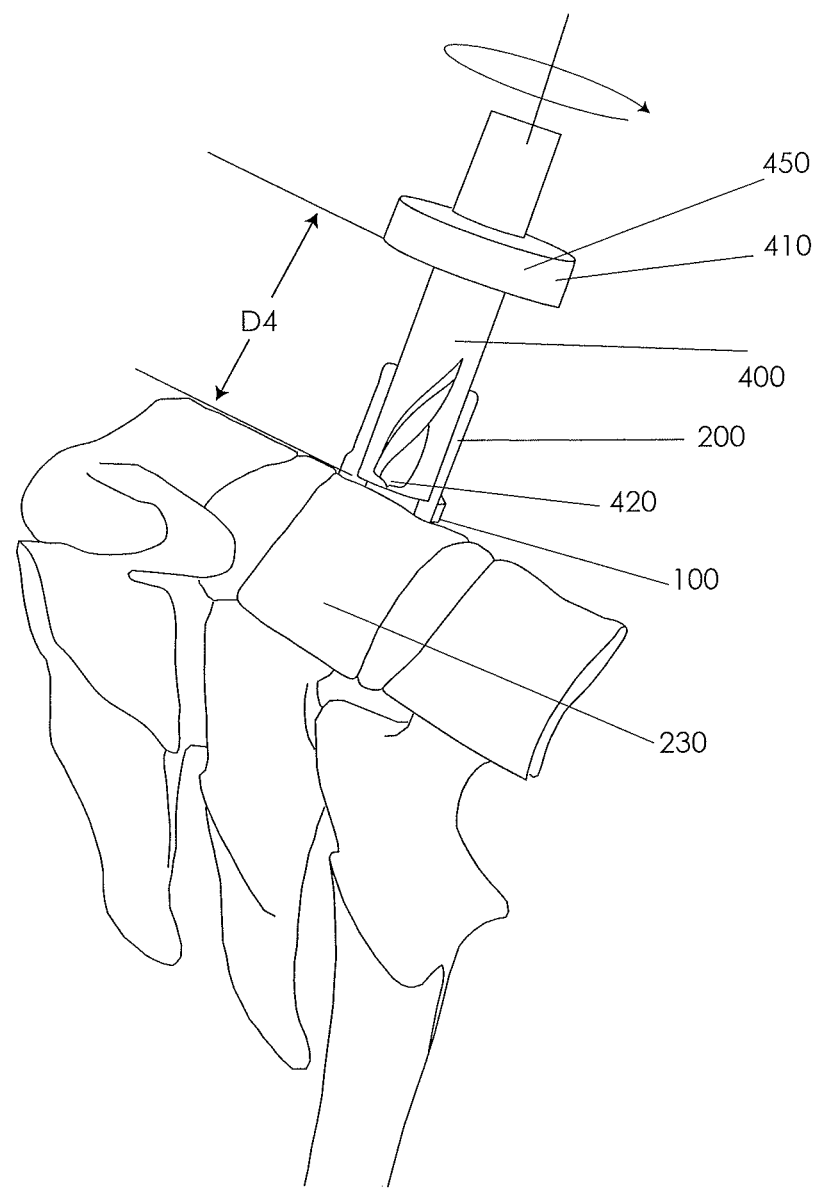
FIG. 13 is a cross section view showing a bone drill in position relative to a bone plate and trajectory control sleeve prior to cutting bone tissue.

FIG. 13 shows a bone cutting tool 400, such as a drill, burr, or reamer, inserted through the trajectory control sleeve 200 and the bone plate implant 100 with the tip of the cutting tool 420 at the initial point of contact on the vertebral body. Cutting tool 400 has a mechanical stop 450. The distance D4 from the drill tip 420 to the lower surface 430 of the drill stop 450, is a prescribed dimension equivalent to the measured distance L2 (see FIG. 9A) plus the desired depth of penetration into the vertebral body, such depth being established by the surgeon through radiographic analysis.

Figure 14:
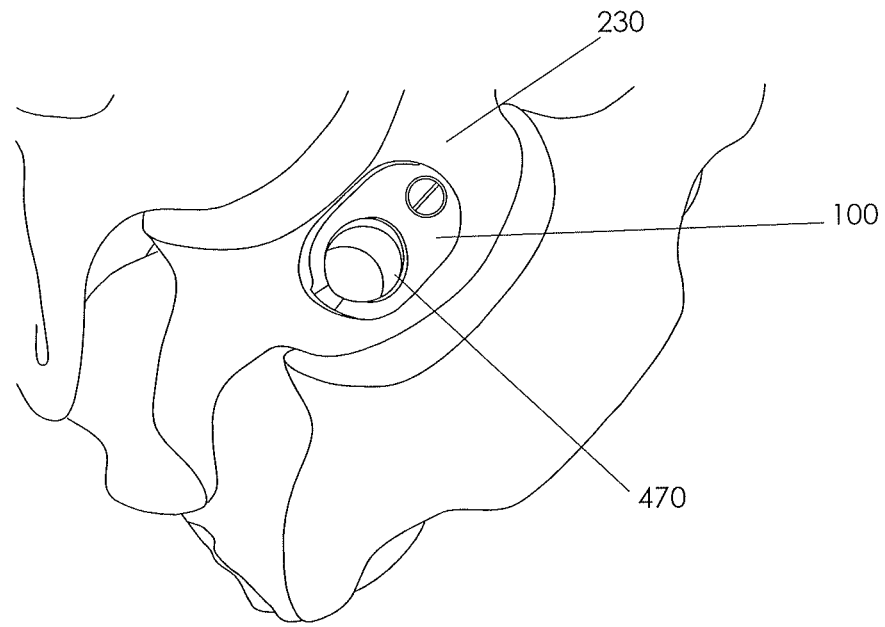
FIG. 14 is a perspective view of a bone plate after drilling has been completed and the trajectory control sleeve has been disengaged from the implanted bone plate.

FIG. 14 shows a surgical access channel 470 in a vertebral body 230, as viewed through the bone plate implant 100 after drilling has been completed and the trajectory control sleeve has been removed from the plate. After removal of the trajectory control sleeve, a neural decompression or other surgical procedure is performed through the access channel. On completion of the procedure, an intra-vertebral bone implant 500 is inserted (FIGS. 15 and 16) into access channel 470 to fill an close it, restore mechanical strength and stability to the host vertebral body 230, and to provide a medium within the vertebral body suitable for osteogenesis.

In some embodiments of the invention, the intra-vertebral access channel 470 (FIG. 14) of an implantable bone plate has a diameter of about 5 mm to about 8 mm. This size creates a surgical field that is sufficiently open enough for typical procedures, and is sufficiently large enough to minimize the possibility that the access channel will not intersect the area of neural compression. In some embodiments, the angle of entry a provided by the access channel is about 10-30 degrees, with the center of the point of entry being generally at mid-point on the cranio-caudal length of the vertebra. While these dimensions are typical, alternative embodiments of bone plate implants may have varying widths and geometries so as to accommodate wide anatomical variations. In various alternative embodiments, trajectory control sleeve devices also may include a wide range of angles and depths for the same reason.

Figure 29:
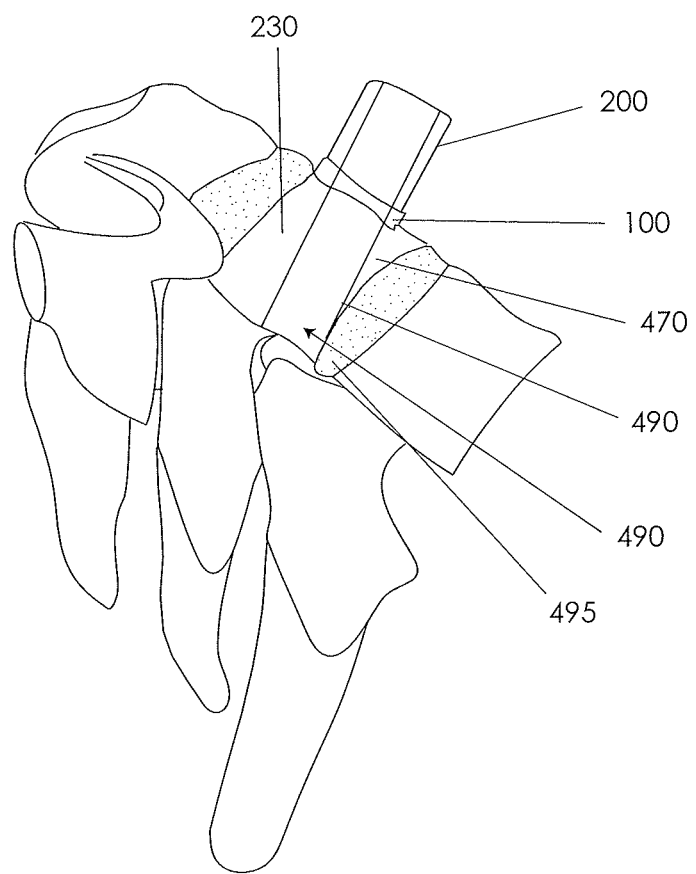
FIG. 29 shows a typical access channel that may be produced with the inventive systems and methods.

With a combination of the angle of entry, the point of entry into the vertebral body, and the size of drill used to create the access channel 470, some embodiments may result in a penetration of the posterior disc space in the posterior 20%-30% of the disc volume 480, leaving the vertebral end plate 490 and the native disc tissue 495 substantially intact. FIG. 29 illustrates a typical access channel 470 that may be formed using a 6 mm drill diameter, about a 10 degree angle of entry, with an entry point on the cranio-caudal centerline of the vertebral body.

Figure 15:
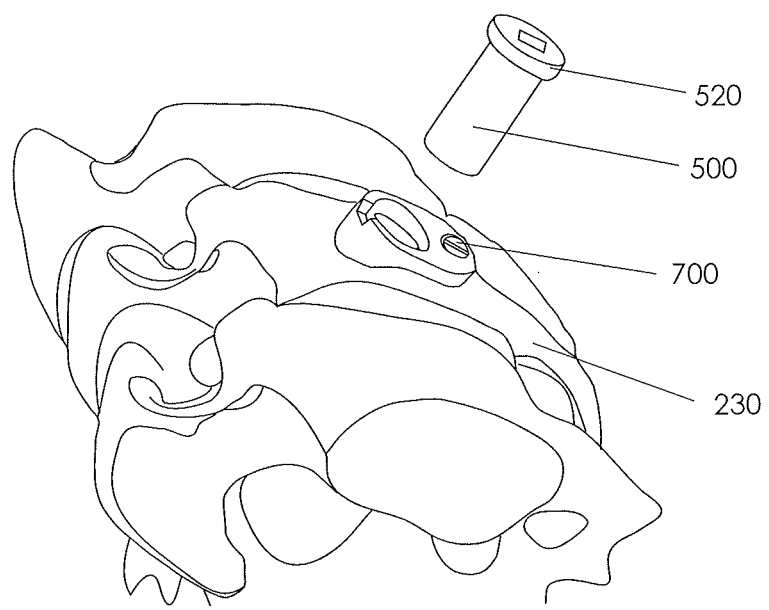
FIG. 15 is a perspective view of a spinal repair implant in the pre-insertion position relative to the implanted bone plate.
Figure 16:
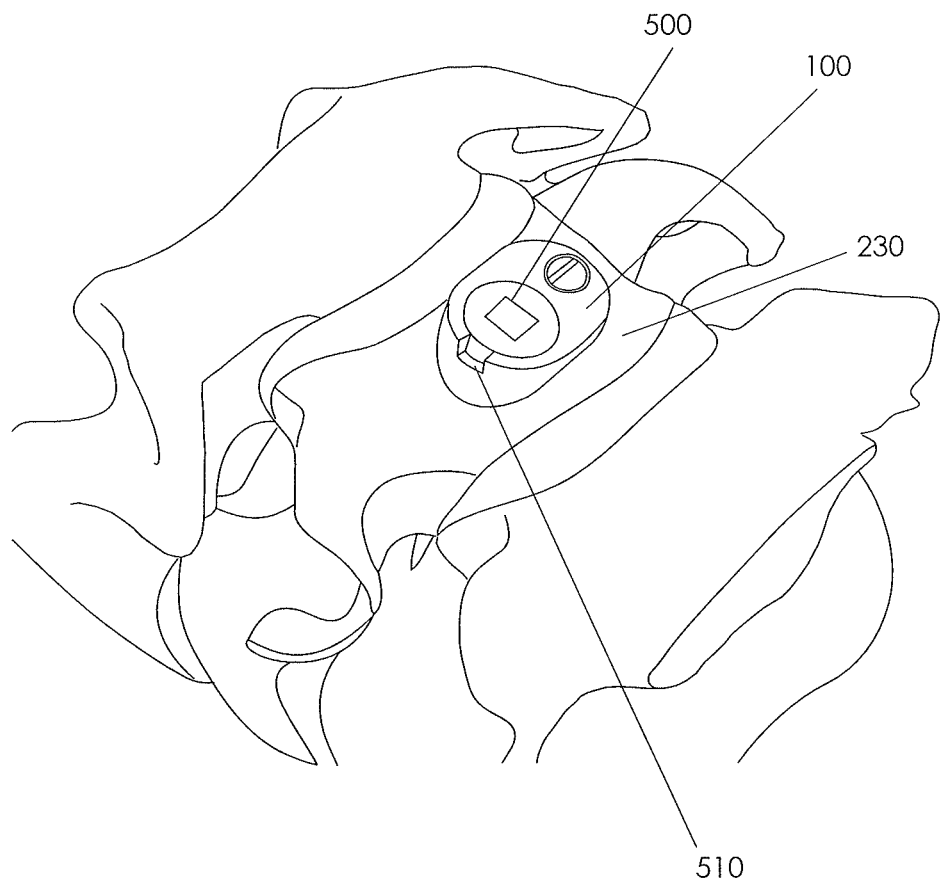
FIG. 16 is a perspective view of a spinal repair implant installed into an access channel through an implanted bone plate.

FIG. 15 shows an intra-vertebral implantable bone repair device 500 positioned for implantation within the vertebra 230 through the bone plate implant 100. Various embodiments and features of a bone repair device are described in U.S. Provisional Patent Application No. 60/990,587 of Lowry et al. (filed on Nov. 27, 2007, entitled "Methods and systems for repairing an intervertebral disk using a transcorporal approach"), which is incorporated herein in its entirety by this reference. In the embodiment shown, implant 500 has an abutting surface 520 adapted to engage with a corresponding surface of the bone plate implant. This arrangement prevents excess penetration of the implant through the access channel and prevents the implant from compressively engaging neural elements. FIG. 16 shows the implantable device 500 in the final installed position relative to the bone plate 100. The device 500 has a locking mechanism 510, such as a conventional bayonet mount, for engaging the bone plate in order to prevent migration of the implant within or out of the access channel.

FIG. 17 shows an alternative embodiment 620 of an implantable bone plate as previously described and shown in FIGS. 1 and 2. In this present embodiment, bone plate 620 has a larger lateral dimension to accommodate particular anatomies that may be encountered, including those of patients, for example, with small stature, degenerative bone conditions, or osteophytes or other abnormalities that may require alternate fixations. To assure accurate location of the device relative to the medial centerline of the vertebra, implant device 620 may include a viewing port 650 or some other positioning indicator. FIGS. 18A and 18B show anterior perspective and side views, respectively, of the engagement of a trajectory control sleeve 200, as previously described, with the alternative bone implant device embodiment 620.

In another alternate embodiment, an implantable bone plate and bone cutting device may be formed as a unitary device and temporarily fixed to the vertebral body. In this embodiment an intra-vertebral access channel is created using the temporarily implanted device; subsequently, the device is removed, the surgical procedure performed, and the access channel repaired using the intra-vertebral implant as previously described. In this embodiment, a bone cutting device may have a least two cutting diameters or widths, the first being that necessary to produce the access channel, the second being a larger diameter configured to remove an annulus of bone on the anterior vertebral surface so as to provide an abutting surface against which the implant would rest in order to prevent over-penetration of the intra-vertebral repair implant within the vertebra.

Figure 19:
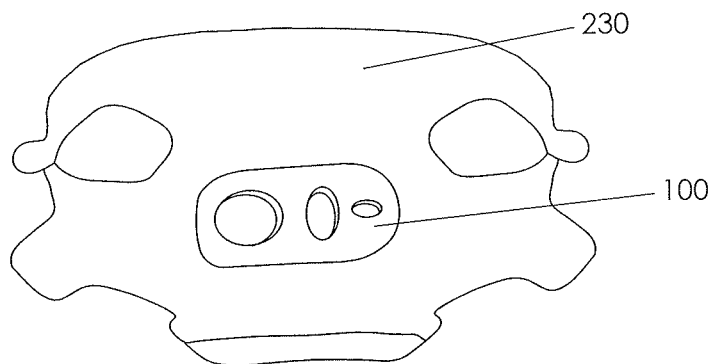
FIG. 19 shows an implantable bone plate in situ on a vertebral surface.
Figures 20, 21:
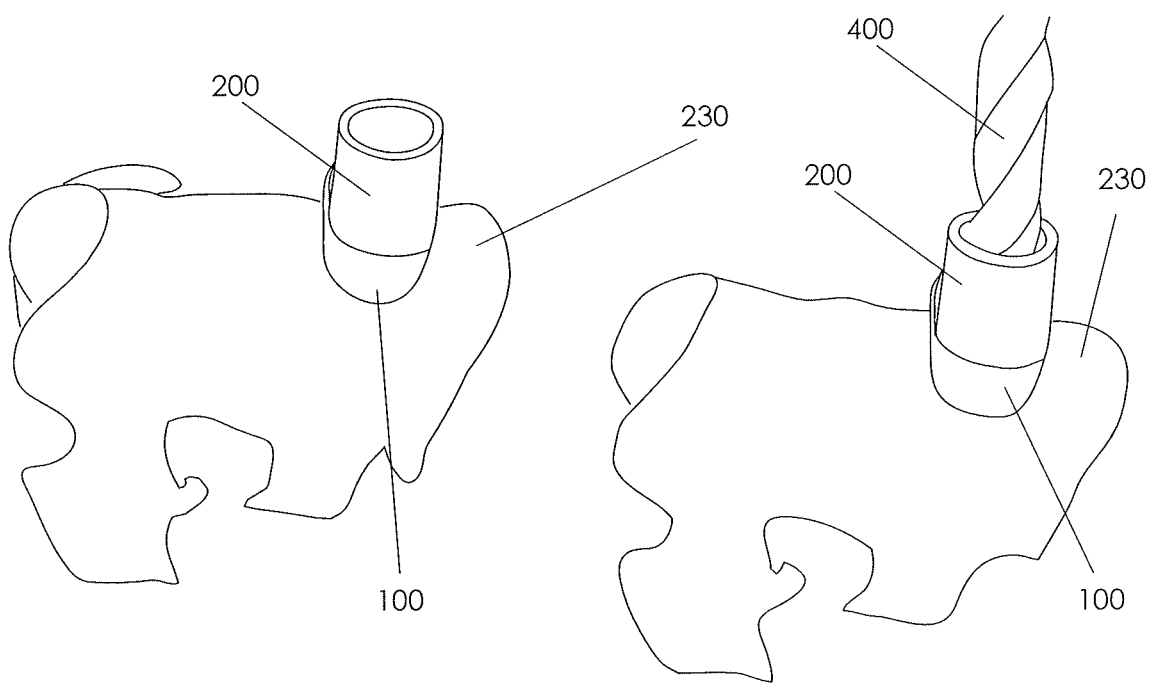
FIG. 20 shows a perspective view of an implantable bone plate and trajectory control sleeve in situ on the vertebra surface.
FIG. 21 shows a drill cutter engaging vertebral bone tissue through the trajectory control sleeve.
Figure 22:
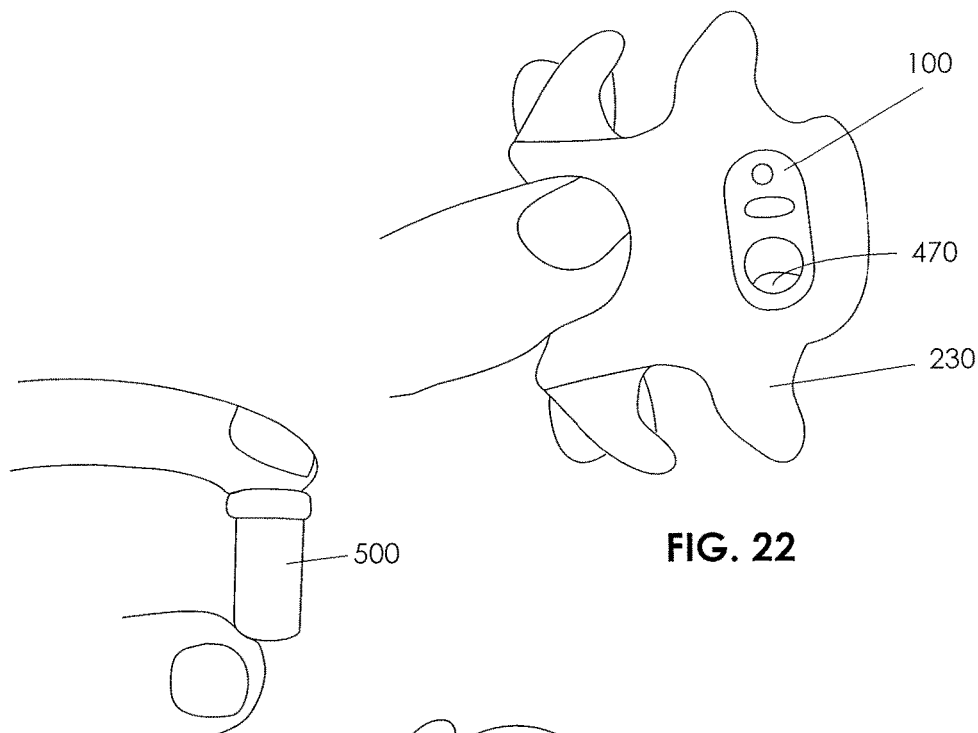
FIG. 22 shows an access channel through an implanted bone plate and into vertebral bone tissue.
Figure 23:
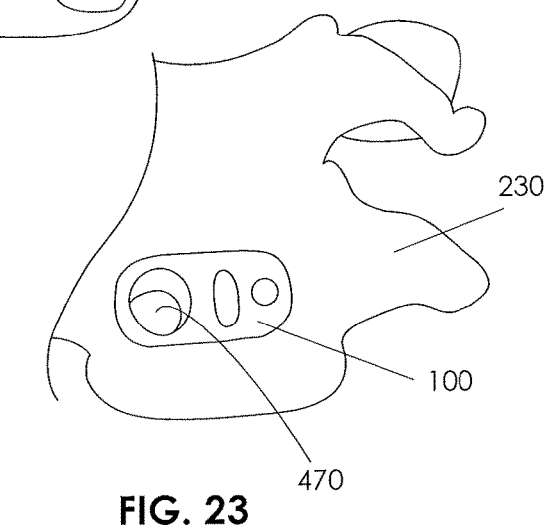
FIGS. 23 and 24 show an intra-vertebral repair device engaging vertebral bone through the bone plate.
Figure 24:
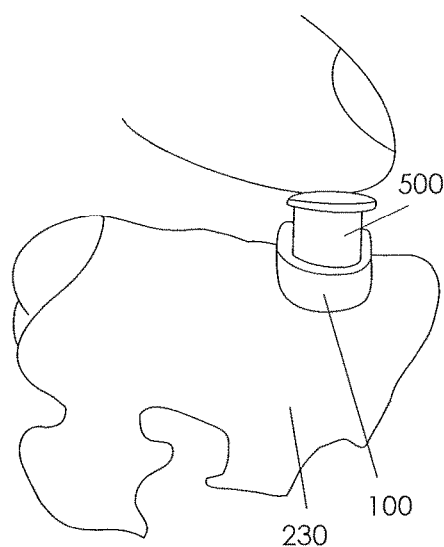

FIGS. 19-24 show exemplary devices being put to exemplary use to evaluate the practical viability, fit, and the functionality of methods for their use. FIG. 19 shows an implantable bone plate 100 in situ on a vertebral surface 230. FIG. 20 shows a perspective view of the implantable bone plate and trajectory control sleeve 200 in situ on the vertebral surface. FIGS. 21-24 include a view of surgeon's finger to show scale and feasibility of manual manipulation of elements of the inventive system. FIG. 21 shows a bone cutting tool 400 engaging vertebral bone tissue through the trajectory control sleeve 200. FIG. 22 shows an access channel 470 through the implanted bone plate and into vertebral bone tissue. FIG. 23 shows an intra-vertebral repair device 500 being readied for engaging vertebral bone through the bone plate 100.

Figure 25A:
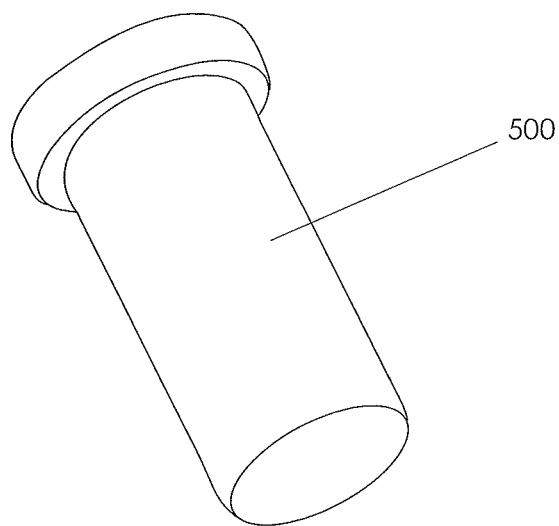
FIGS. 25A and 25B show views of an intravertebral repair device embodiment with a proximal abutting surface orthogonal to the body of the device.
Figure 25B:
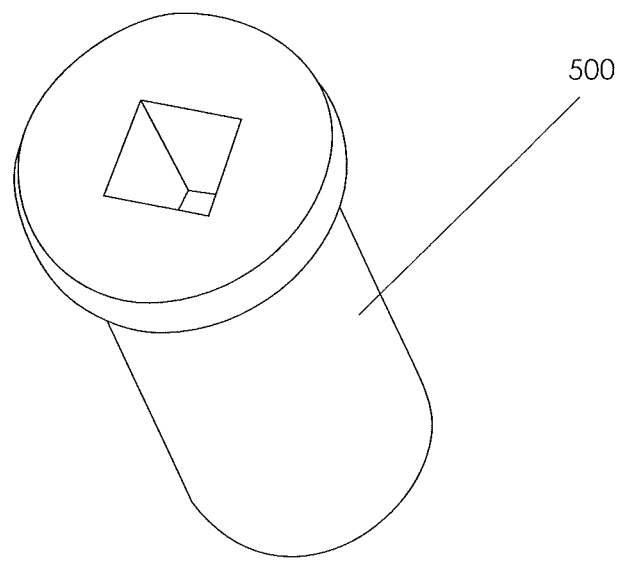

FIGS. 25A-27B show embodiments of alternative external geometries of the intra-vertebral implantable devices 500 as may appropriate for particular patients or procedures. FIGS. 25A and 25B show views of what may be considered a default embodiment of an intravertebral repair device with a proximal abutting surface orthogonal to the body of the device. FIG. 25A shows the device from a proximally-directed perspective, while FIG. 25B shows it from a distally-directed perspective.

Figure 26A:
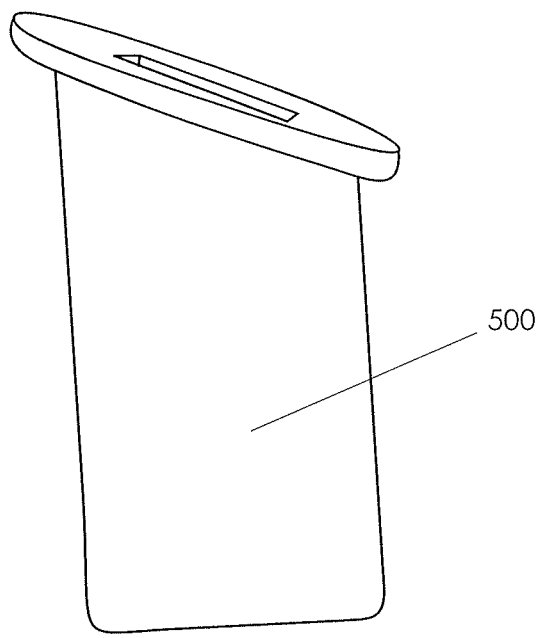
FIGS. 26A and 26B show views of an intravertebral repair device embodiment with a proximal abutting surface canted with respect to main axis of the body of the device.
Figure 26B:
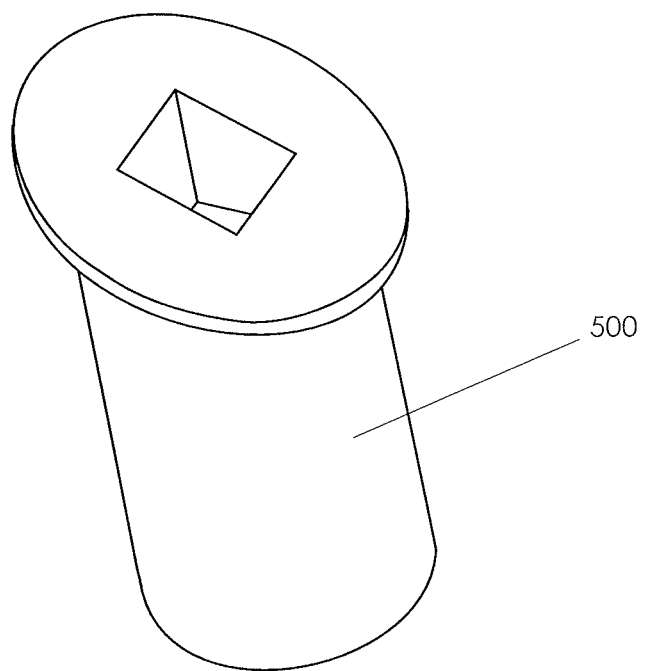
Figure 27A:
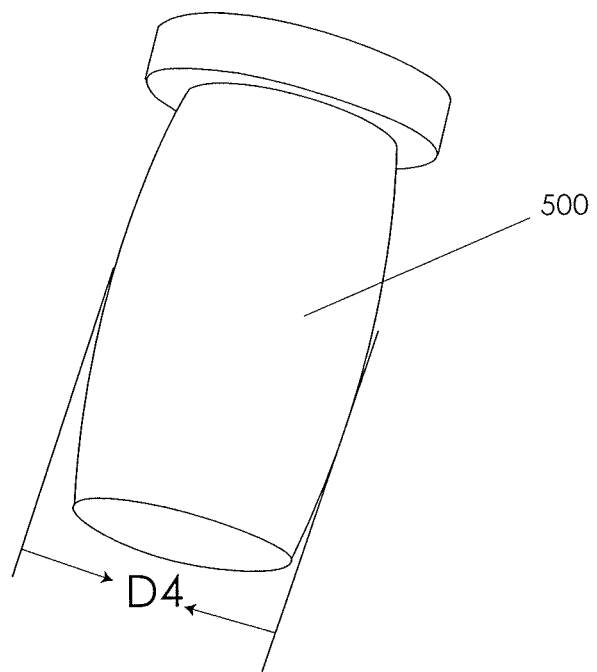
FIGS. 27A and 27B show views of an intravertebral repair device embodiment with a convex external profile, wider in its central portion, narrower at proximal and distal ends.
Figure 27B:
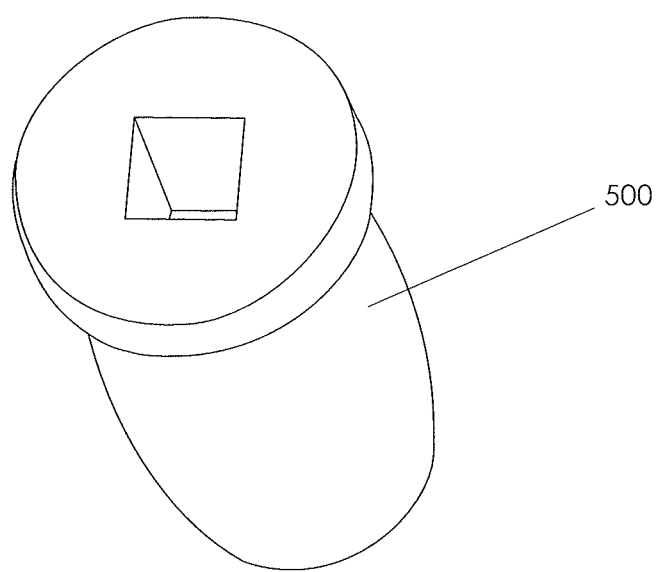

FIGS. 26A and 26B show and embodiment wherein abutting surface 520 is canted at an angle not orthogonal to the central axis of the device 500. FIGS. 27a and 27b show an intra-vertebral implant device 500 with a convex external profile where dimension D4 is nominally larger than the internal diameter of the access channel so as to compressively engage the cancellous bone tissue. Such a compressive engagement can improve the interference fit of the device therein and to inter-diffuse cancellous bone tissue within the implant volume to improve osteogenesis.

FIG. 28 shows an assemblage of some of these system elements, and was described at the outset of the detailed description; shown is an implantable vertebral plate 100, a cutting tool guide 200, a confirmation device or depth gauge 300, a collar 310 for the confirmation device, a cutting tool 400, an implantable device 500, and an implant locking device 600. FIG. 29 provides an exemplary embodiment of the invention that was discussed earlier in the context of the formation of an access channel, in conjunction with associated description of FIGS. 14-16.

Implantation of the patient's own bone tissue (an autologous graft) is a generally advantageous approach to repairing bone, as autologous grafting typically yields high success rates and a low rate of surgical complications. Accordingly, some embodiments of the invention include using core bone tissue harvested from the fanning of the access channel, and implanting the plug, intact, in the form of bone repair graft. An advantage to recovering and making use of bone derived from the channel includes the absence of a need to harvest bone from a second site. Embodiments of the invention, however, do include harvesting bone from secondary sites on the patient, such as the iliac crest, as may be appropriate in the practice of the invention under some circumstances. In some embodiments, for example, it may be advantageous to supplement bone derived from the access channel with bone from other sites. In still other embodiments, under various clinical circumstances, it may be appropriate to make use of bone from donor individuals. Bone from other autologous sites or other donor individuals may be used as a repair device in the form of an appropriately formed plug, or bone may be fragmented or morselized, and packaged as a solid plug, or bone may be included as a preparation provided in a porous cage, as described further below.

Some embodiments of methods provided make use of a trephine type bone cutting system, as noted above. With a trephine bone cutting system, the external diameter of the bone tissue core is about equal to the internal diameter of the trephine device, while the internal diameter of the access channel is about equal to the external diameter of the device. Thus, a trephine-derived bone plug from forming the access channel provides an appropriately-sized piece to be inserted into the channel for repair and healing, but does not necessarily make intimate contact with the inside surface of the channel due to the width of the kerf created by the trephine.

Optimal healing and recovery from implantation of bone material into an access channel occurs when there is an intimate or compressive engagement of the graft material with the vertebral bone tissue (substantially cancellous bone), as this intimate association provides for rapid blood profusion and bone healing while providing mechanical support during healing. Accordingly, an embodiment of the bone repair device provided herein includes a device with bone tissue inside a porous cage, as described in detail below.

The porosity of the cage is a particularly advantageous feature for allowing cell to cell contact through the boundary of the device. To some degree, it may also allow cell migration, however the most advantageous factor in promoting rapid healing is cell to cell contact that initiates sites of tissue unification, which can then spread, stabilize a healing zone around the graft or bone repair device, and ultimately lead to effective fusion and integration of the graft within the host vertebral body.

A porous cage, as provided by aspects of this invention, also has a compressibility, such that when the contents of the cage are subject to a compressive force, however transient and minimal, blood or plasma and bone cells that are present in the harvested cancellous bone are forced outward into the environment within and around the access channel site. Extrusion of biological fluid in this manner, advantageously packs bone tissue closer together within the cage, and bathes the periphery of the graft and the host-graft intersectional zone with a medium that is optimal for exchange of dissolved gas and nutrients that are critical in the initial stages of healing. Some embodiments of the invention include bathing the bone tissue preparation in a supportive liquid medium before implantation. Such bathing may occur prior to placing the bone tissue preparation in the porous cage and/or after placing the preparation in the cage. The liquid medium may be any appropriate cell culture medium, and may be further supplemented with biological agents, such as osteogenic agents or other growth factors.

Embodiments of the implantable porous cage bone repair device, as provided herein, encapsulate the bone tissue contained therein, and provide mechanical stability to the access channel during healing. These embodiments compensate for the volumetric loss associated with the bone cutting process of the trephine and promote contact between the bone volume within the device and the surrounding vertebral bone tissue. The device, as a whole, and like other bone repair embodiments provided, cooperates with the implanted bone plate so that the orientation and penetration depth of the implant device within the access channel may be controlled. These forms of control assure that the device does not over-penetrate through the channel, thereby compressing the dura mater or neural elements within the vertebra, and assuring that the implanted device cannot migrate in an anterior direction out of the access channel.

Exemplary embodiments of the porous cage device and associated method of use will now be described in further detail, and in the context of FIGS. 30-37.

Figure 30:
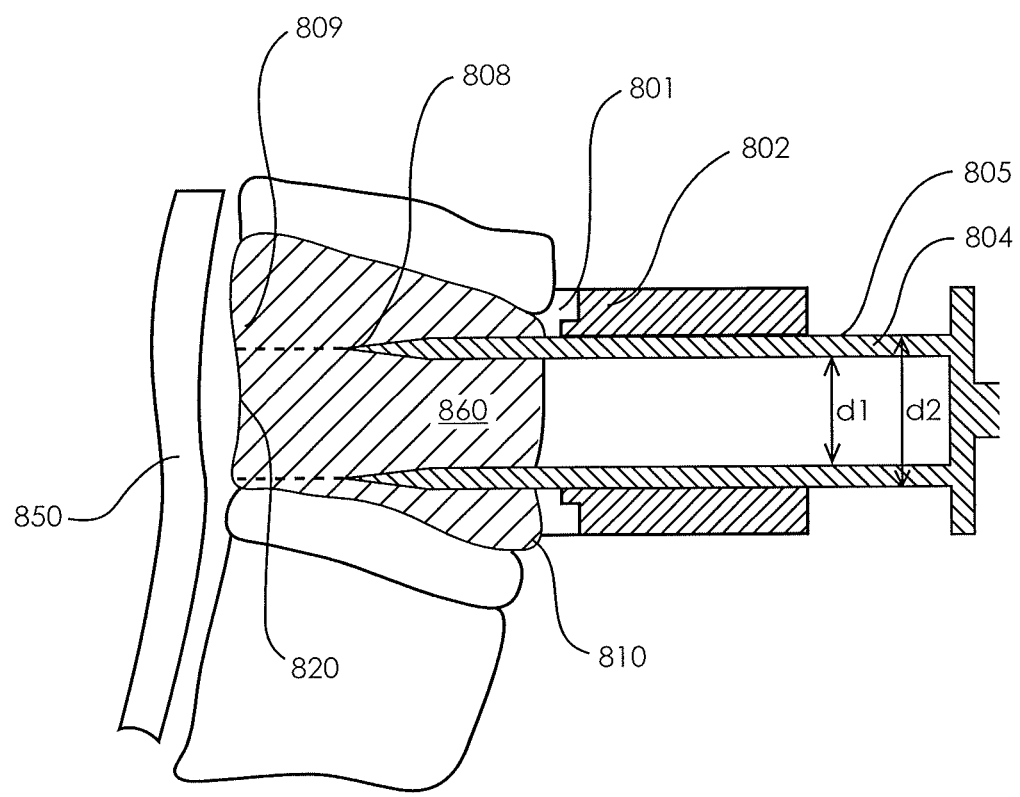
FIG. 30 shows a cross sectional view of an access channel being formed in a vertebral body with a hollow cutting tool, a trephine, which forms an access channel with a removal bone plug.

FIG. 30 provides a cross-sectional view of a vertebral body 809 with a bone plate 801 attached to the anterior bone surface 810. Mounted on the bone plate is a trajectory control sleeve 802 cooperating with the bone plate 801 to establish and control the trajectory of a bone cutting tool 804 with a cutting surface 808 through the vertebral body to direct the trajectory of the formed access channel to a prescribed point of exit at the posterior surface of the vertebra 820, in the locale of a site of medical interest.

The depicted exemplary bone cutting tool 804 is a hollow bone cutting tool, a trephine, with an external diameter 805 selected to be complementary to the internal diameter of the trajectory control sleeve 802, and to cooperate therewith so as to assure that the centerlines of the bone cutting tool and the trajectory control sleeve are substantially co-incident during the bone cutting process. The trephine 804 progresses through the vertebral body 820 from an anterior to posterior direction until the cutting surface 808 penetrates the cortical bone at the posterior surface of the vertebra proximal to the spinal cord 850. Upon removal of the trephine from within the vertebral body, a core of bone tissue within the interior of the trephine is extracted from the wound opening, thus creating or exposing an open access channel from the anterior surface of the vertebral body to the neural elements and the prescribed site of medical interest immediately behind the posterior wall of the same vertebral body.

Figures 31, 32:
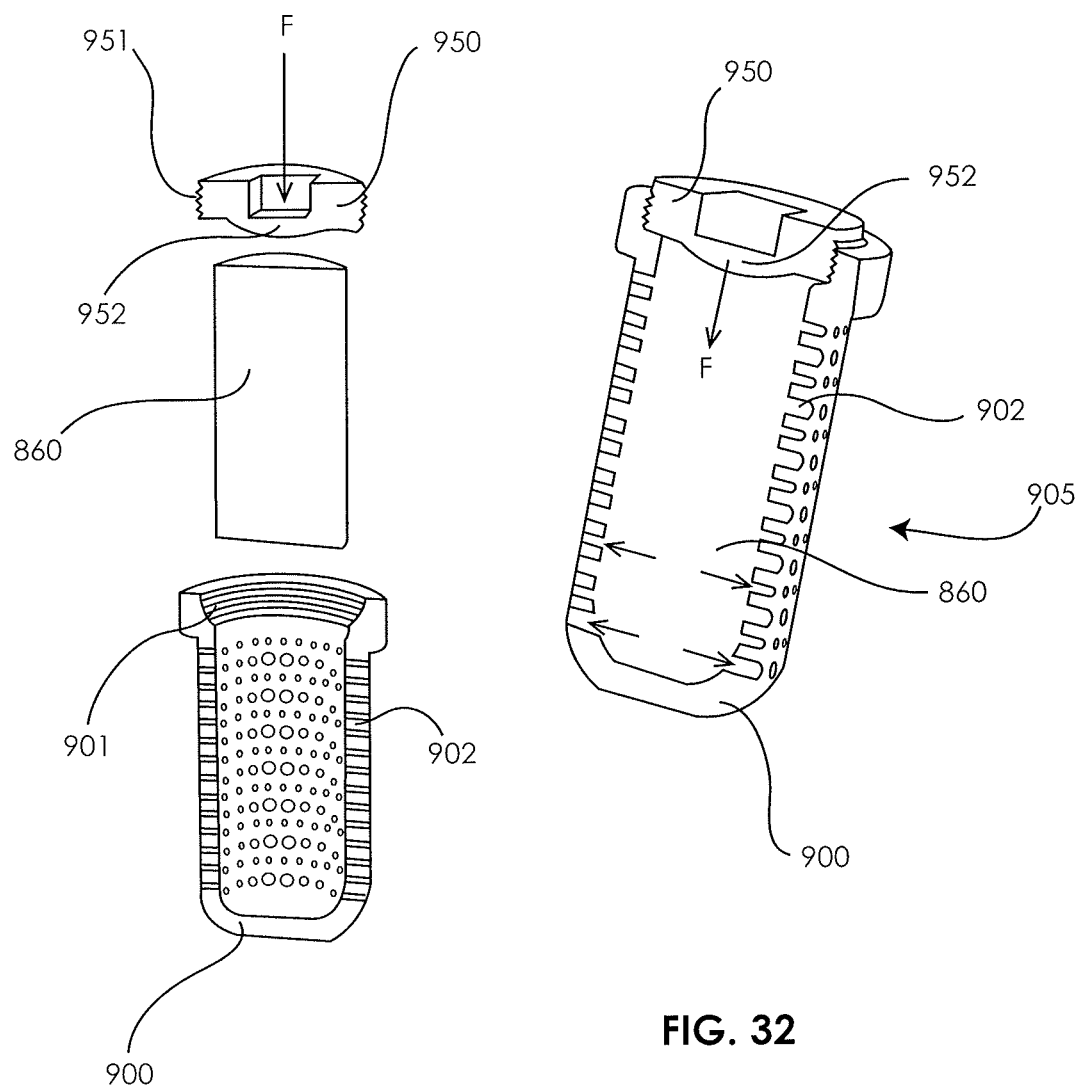
FIG. 31 shows an exploded view of a bone repair device with a porous body configured to hold bone tissue, and to allow compression of the tissue upon closing the porous body.
FIG. 32 shows a cut away cross sectional view of the bone repair device of FIG. 31 in assembled form.

FIG. 31 shows components of an exemplary bone repair device in a linearly exploded view from an external perspective. At the top, a cap 950 is above a vertebral bone core 860; the bone core is positioned for placement in a porous cage 900. FIG. 32 is a cross-sectional view of the fully assembled device 905. According to aspects of the inventive method, the vertebral bone core 860 is placed within an implantable intravertebral bone repair device 900 with a porous wall, and encapsulated by a cap or closing element 950. In this exemplary embodiment the cap has a screw thread 951 disposed to engage a mating thread 901 on the body 900 of the implantable device; the cap further has a compression element 952 disposed to exert a compressive force F on the bone graft core 860 when the cap is being closed on the body 900 of the repair device, and consequently inducing extrusion of native tissue within the device, through open pores 902 contained within the perimeter wall of the implant device. As described above, the bone tissue placed within the body of the repair device is not necessarily an integral bone plug intact from the trephine used to form the channel; the bone tissue may be a fragmented or morselized preparation, it may include bone from another site on the patient, and it may include bone from another donor.

Figure 33:
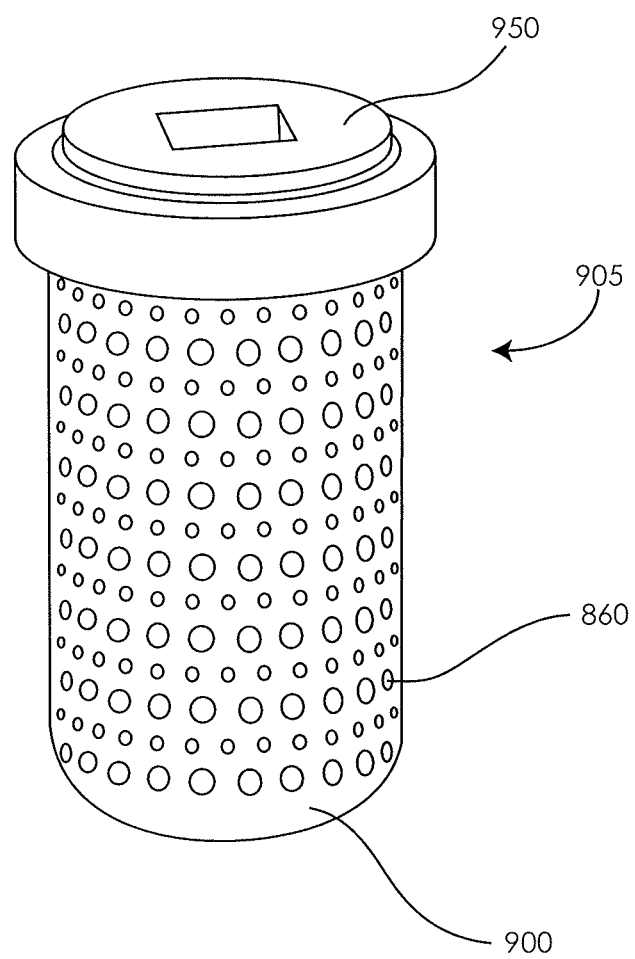
FIG. 33 shows an external view of the assembled bone repair device of FIG. 33 with bone tissue and associated fluid being extruded under pressure.

FIG. 33 provides an external perspective view of an assembled bone repair device 905. This view captures a moment shortly after the cap 950 has been closed, and by such closing has increased the pressure on the bone tissue contained within the device. By virtue of this elevated pressure within the porous walled body 900, bone core graft tissue and associated biological fluid are extruding through the porous perimeter wall. In some embodiments of the method, the cap 950 is closed on the porous body 900 of the repair device immediately prior to insertion of the assembled device 905 into the access channel within the host vertebral body, and in some embodiments of the method, the cap is closed after insertion of the porous body 900, thereby forming the complete assembly 905 in situ.

Figure 34:
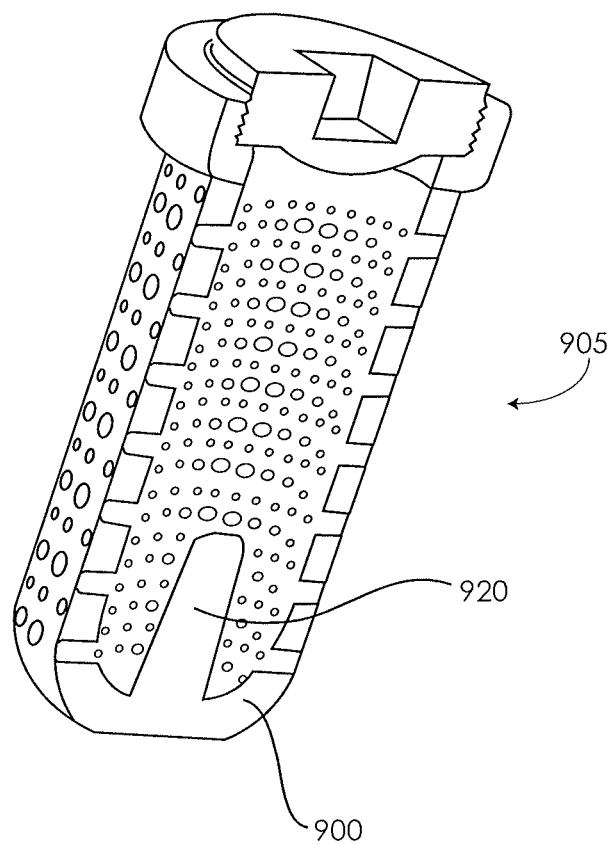
FIG. 34 shows an alternative embodiment of an assembled bone repair device with a porous body and with an internal pressure-amplifying feature.

FIG. 34 shows a cross sectional view of an alternate embodiment of the porous body portion 900' of an assembled repair device 905' that includes an internal tissue expander feature 920 disposed to induce radial extrusion of the bone core tissue through the orifices.

Figure 35:
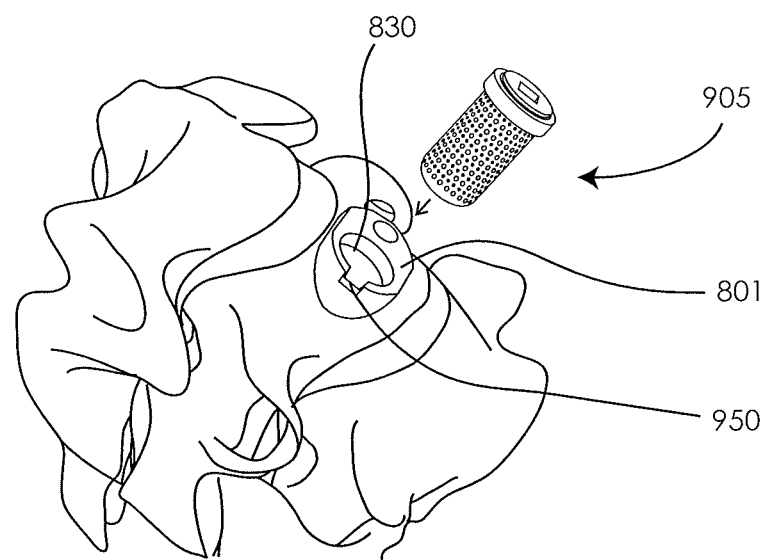
FIG. 35 shows a bone repair device with a porous body containing bone tissue poised in a position from where it is about to be implanted in an access channel within a vertebral body.
Figure 36:
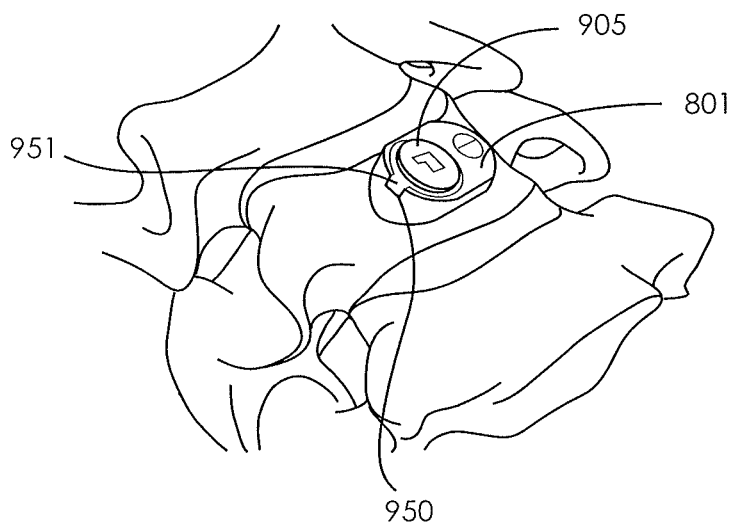
FIG. 36 shows the bone repair device of FIG. 35 implanted in the vertebral body, and locked into a bone plate.
Figure 37:
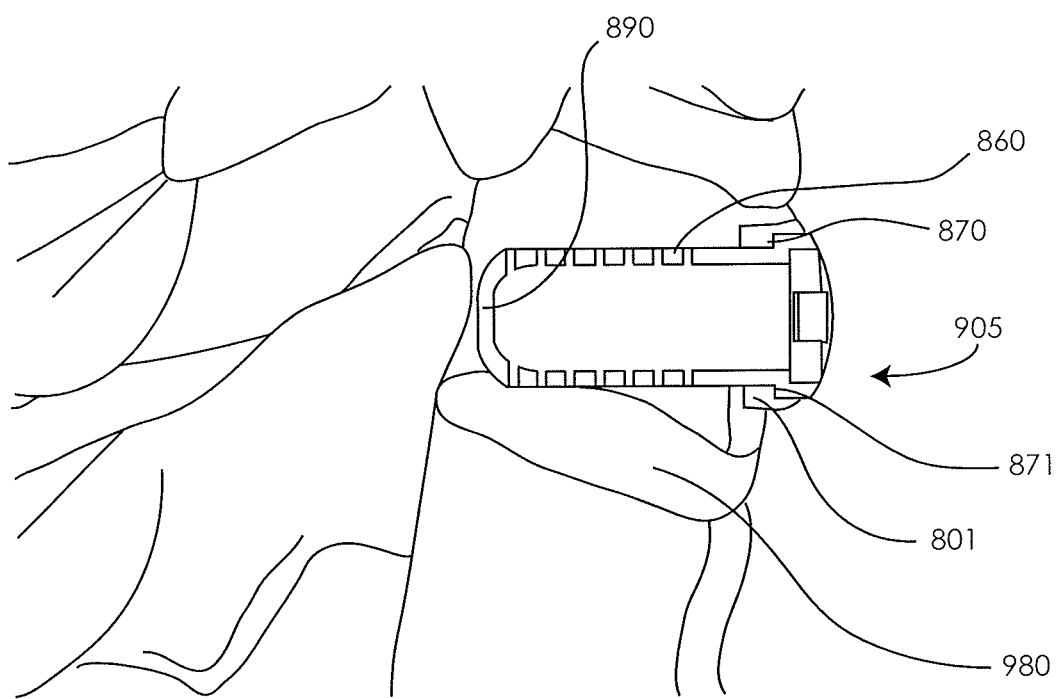
FIG. 37 shows a lateral cross sectional view of a bone repair device with a porous body containing bone tissue, in situ, within an access channel in a host vertebral body.

FIGS. 35 and 36 show similar views of the porous cage device embodiment 905 as were provided earlier by FIGS. 15 and 16 for solid bone repair device 500 embodiments. FIG. 37 shows a cross sectional view of the implanted device 905 within an intravertebral access channel 470. Upon completion of the surgical procedure through the access channel, the bone repair implant assembly 905 (containing the harvested bone graft core 860) is introduced into the transcorporal access channel through the aperture 830 in the implanted bone plate device 100. In one exemplary embodiment, the bone repair assembly 905 has an abutting surface disposed to cooperate with a mating surface of engagement 871 on the bone plate implant. The completed mating of the bone repair assembly 905 with the bone plate 100 prevents the distal tip 890 of the implant assembly from penetrating into the spinal cord volume posterior to the vertebral body.

The implantable repair device assembly 905 further has an orientation and locking feature 951 disposed to engage a mating feature 950 on the implantable bone plate 100 so as to control the radial orientation of the implant with respect to the bone plate and to lockably engage the bone repair implant device with the bone plate implant so as to prevent migration or expulsion of the bone repair implant assembly 905 out of the access channel. Such radial orientation of the implant relative to the access channel may be particularly advantageous when the bottom or distal end of the repair device body 900 is formed at an angle (not shown) to completely fill the access channel.

As a consequence of the implantation of the bone repair assembly 905 within the access channel, the general mechanical integrity of the vertebral body has been restored, the internal void of the access channel has been filled in a manner such that native disc material 980 cannot migrate into the channel, bone tissue (typically autologous) has been re-implanted in a manner that establishes intimate contact between the bone graft and the cancellous bone of the vertebra thereby promoting blood profusion and rapid bone healing.

FIGS. 38-59 show another embodiment of transcorporal spinal decompression and repair system and method of use. As in the previously described embodiments, the system and method of this exemplary embodiment involve the use of a trajectory control sleeve to form an access channel with a prescribed trajectory through a vertebral body, from an anterior surface entry to a prescribed posterior surface opening on the vertebral body. The access channel may then be used to perform a surgical procedure. For example, instruments may be inserted through the access channel for decompressing a neural element, such as an individual nerve root, a spinal cord, a cauda equine, or a combination thereof. The channel may be used to access a portion or the whole of a herniated disc, an osteophyte, a thickened ligament, a tumor, a hematoma, a degenerative cyst, or any other compressing pathology. This embodiment also includes an implant for repairing the access channel after use. In this exemplary embodiment, the trajectory control sleeve is separate from the repair implant. A common mounting hole formed in the vertebral body may be used to first secure the trajectory control sleeve, and then secure the repair implant to the vertebral body. In this embodiment, the repair implant comprises a bone cage integrally formed with a mounting plate that secures the implant to the anterior surface of the vertebral body.

Figure 38:
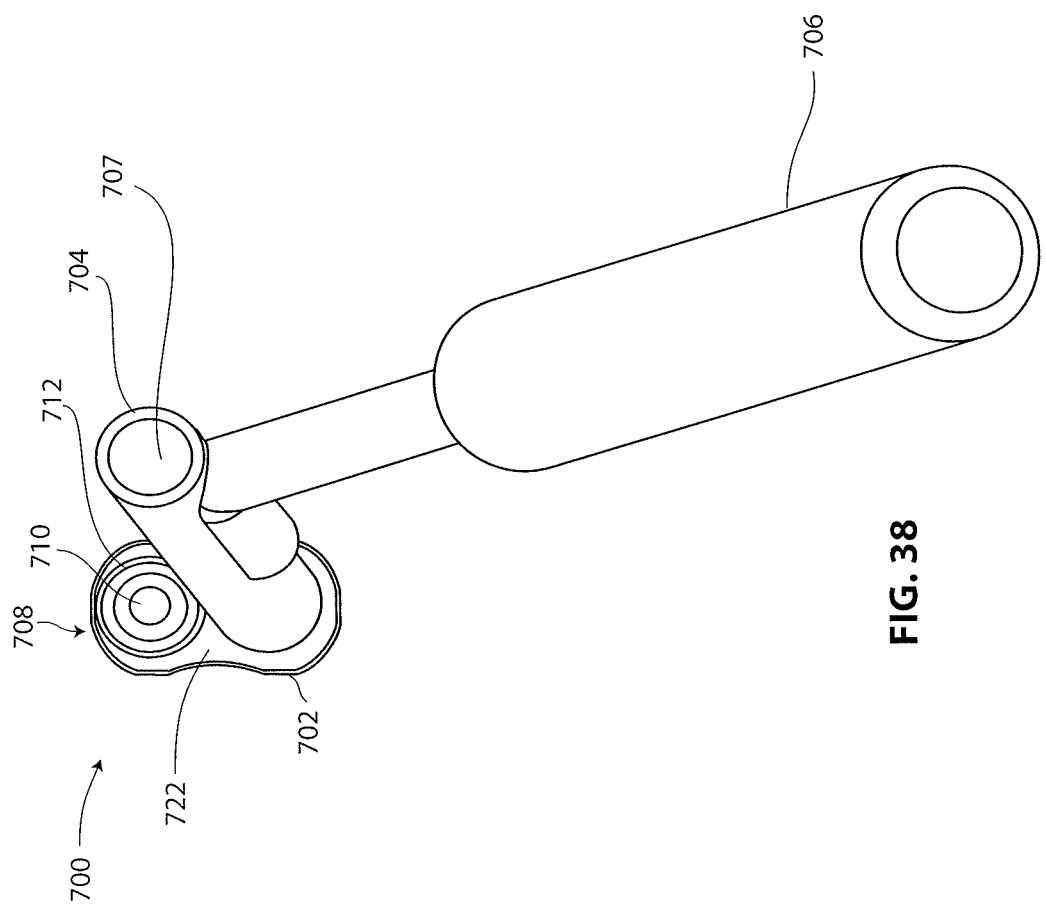
FIGS. 38-40 show various views of a trajectory control tool according to another embodiment.
Figure 39:
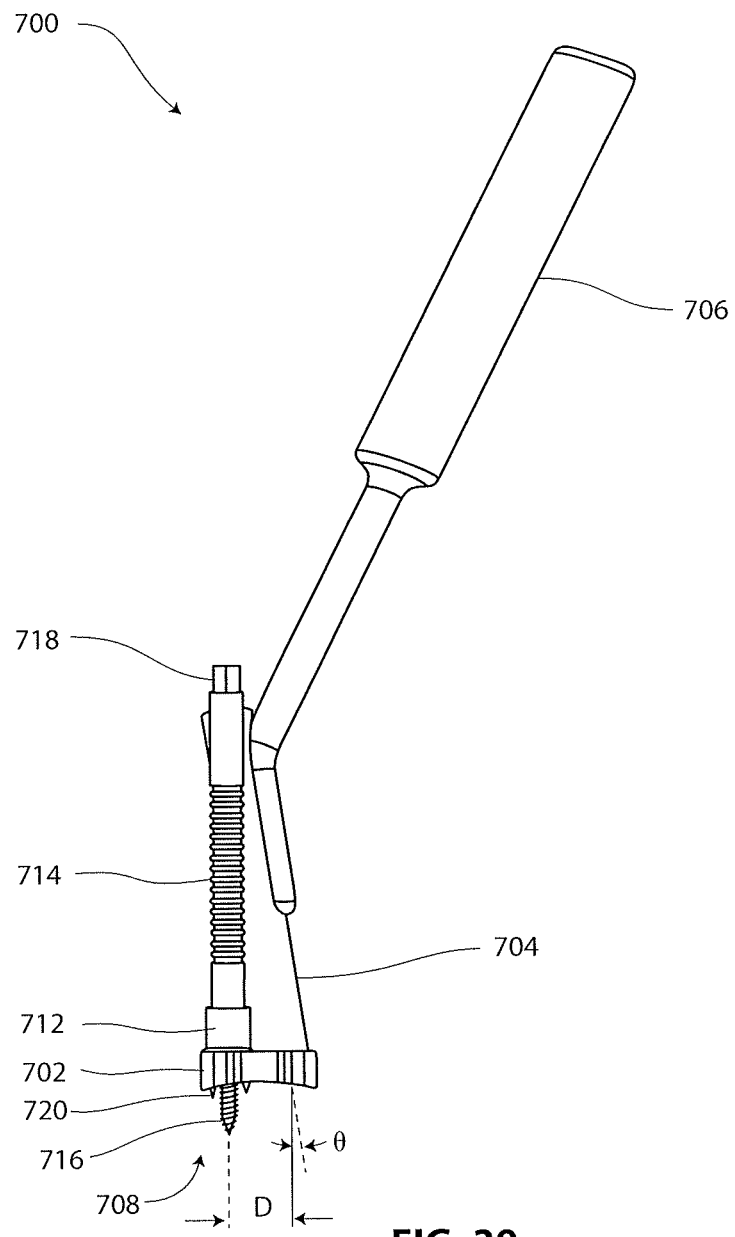
Figure 40:
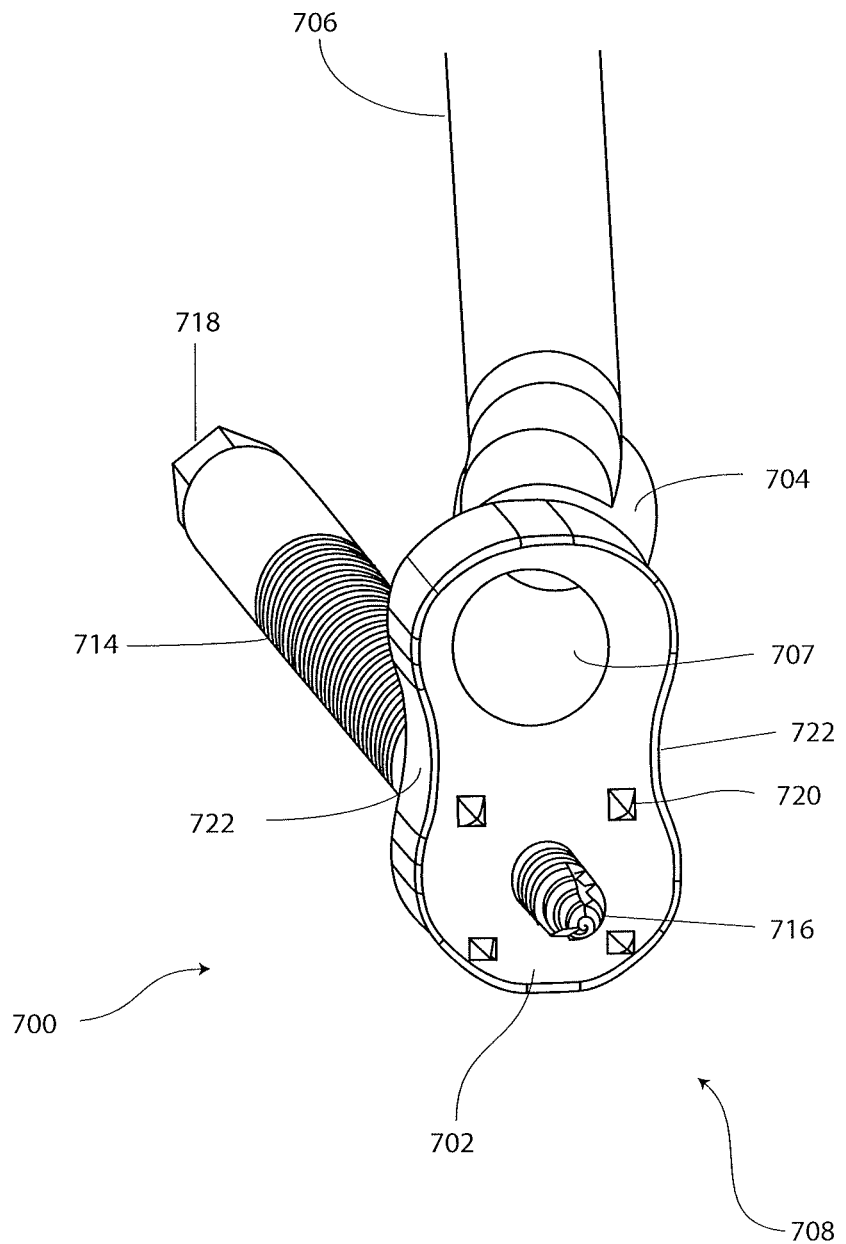

Referring to FIGS. 38-40, a trajectory control tool 700 is shown. In this exemplary embodiment, trajectory control tool 700 includes a base plate 702, a trajectory control sleeve 704 rigidly attached to the base plate 702, and a handle 706 rigidly attached to control sleeve 704. Control sleeve 704 includes a straight lumen 707 that extends from the proximal end of sleeve 704 through base plate 702 at the distal end of sleeve 704. Base plate 702 includes a fastening portion 708 configured to detachably secure tool 700 to the anterior surface of the vertebral body, as will subsequently be described in more detail. In this exemplary embodiment, fastening portion 708 includes a bore 710 through base plate 702, and a fastener sheath 712 rigidly attached to base plate 702 and coaxially aligned with bore 710. Sheath 712 may be configured with an inside diameter larger than the diameter of bore 710, thereby providing a shoulder at the bottom of sheath 712 where it joins plate 702.

As shown in FIGS. 39 and 40, bore 710 and fastener sheath 712 are configured to removably receive the distal end of an elongated fastening device 714. The distal end 716 of fastening device 714 is threaded for engaging with a vertebral body. In some embodiments, distal end 716 is configured to be self-drilling and/or self-tapping. The proximal end 718 of fastening device 714 may be provided with a keyed head as shown for attaching to a handle or other driver device (not shown). A proximal or mid-portion of fastening device 714 may be knurled and/or provided with other gripping features to allow a surgeon to at least partially tighten fastening device 714 by hand. In some embodiments, a lever or handle (not shown) may be formed at the distal end of the fastening device. Fastening device 714 may be provided with a flexible shaft so that the proximal end 718 may be angled away from trajectory control sheath 704 when being turned.

As best seen in FIG. 39, the bottom or posterior surface of base plate 702 may be curved to match the mediolateral curvature of the anterior surface of a vertebral body. Since the curvature of a vertebral body may vary from patient to patient, a series of two or more alternate trajectory control tools may be provided to a surgeon, each with a different curvature on its base plate. In some embodiments, three different sizes of a trajectory control tool are provided, each having a different radius of curvature on its base plate ranging from 15 to 30 mm. If only a single, universal trajectory control tool 700 is provided, the radius of the posterior side of the base plate 702 may be configured to match the smallest vertebral body it is expected to be attached to. With this arrangement, the lateral edges of base plate 702 will still contact the anterior surface of the vertebral body, regardless of its size, thereby preventing trajectory control tool 700 from rocking when attached to the vertebral body.

As best seen in FIGS. 39 and 40, the posterior side of base plate 702 may be provided with one or more sharp projections 720. Projections 720 are configured to bite into the vertebral bone to prevent trajectory control tool 900 from shifting once placed on a vertebral body. Projections 720 may be particularly useful when fastening device 714 is being tightened, to prevent base plate 702 from rotating with device 714 relative to the vertebral body.

As best seen in FIG. 39, trajectory control sleeve 704 may be angled in a mediolateral direction. In some embodiments, the mediolateral angle 0 of sleeve 704 is about 10 degrees from vertical or being perpendicular to base plate 702, with sleeve 704 projecting downwardly and laterally outward (away from a medial plane when mounted on a vertebral body, as will be later described.) Sleeve 704 may alternatively or also be angled in the craniocaudal direction, as seen in FIG. 40. In some embodiments, the craniocaudal angle of sleeve 704 is about 10 degrees from vertical or perpendicular. This can be either in the cranial direction or the caudal direction, depending on which side handle 706 is facing when trajectory control tool 700 is mounted on a vertebral body. Left and right versions of tool 700 may be provided such that the surgeon can specify both the direction of the access channel and the orientation of handle 706. In light of the above, it can be appreciated that trajectory control sleeve 704 forms a compound angle with base plate 702 in this exemplary embodiment. In this embodiment, the axis of fastening portion 708 is vertical or perpendicular to base plate 702 in both the mediolateral and craniocaudal directions.

As also shown in FIG. 39, fastening portion 708 may be laterally spaced apart from trajectory control sleeve 704 by a predetermined distance D, as measured between the axes of these two features where they exit the posterior side of base plate 702 and cross the anterior surface of a vertebral body.

As seen in FIG. 40, base plate 702 may be formed with a dog-bone shape having recesses 722 and/or other marking indicia (not shown) provided on opposite longitudinal sides. Recesses 722 and/or other marking indicia can assist the surgeon in aligning trajectory control tool 700 on the medial centerline of a vertebral body before attaching tool 700 to the vertebral body.

Referring to FIGS. 41-45, an exemplary repair implant 730 is shown. Implant 730 may be used to repair an access channel formed by previously described trajectory control tool 700, as will later be described in more detail. Implant 730 may include a central housing 732 and a plug portion 734. In some embodiments, plug portion 734 is rigidly attached to housing 732 and may be integrally formed therewith. Plug portion 734 may be configured to have an outside diameter that is nominally the same as the inside diameter of previously described lumen 707 of trajectory control sleeve 704. Plug portion 734 may be provided with a rounded distal tip 736 for ease of insertion into an access channel though a vertebral body.

Figure 43:
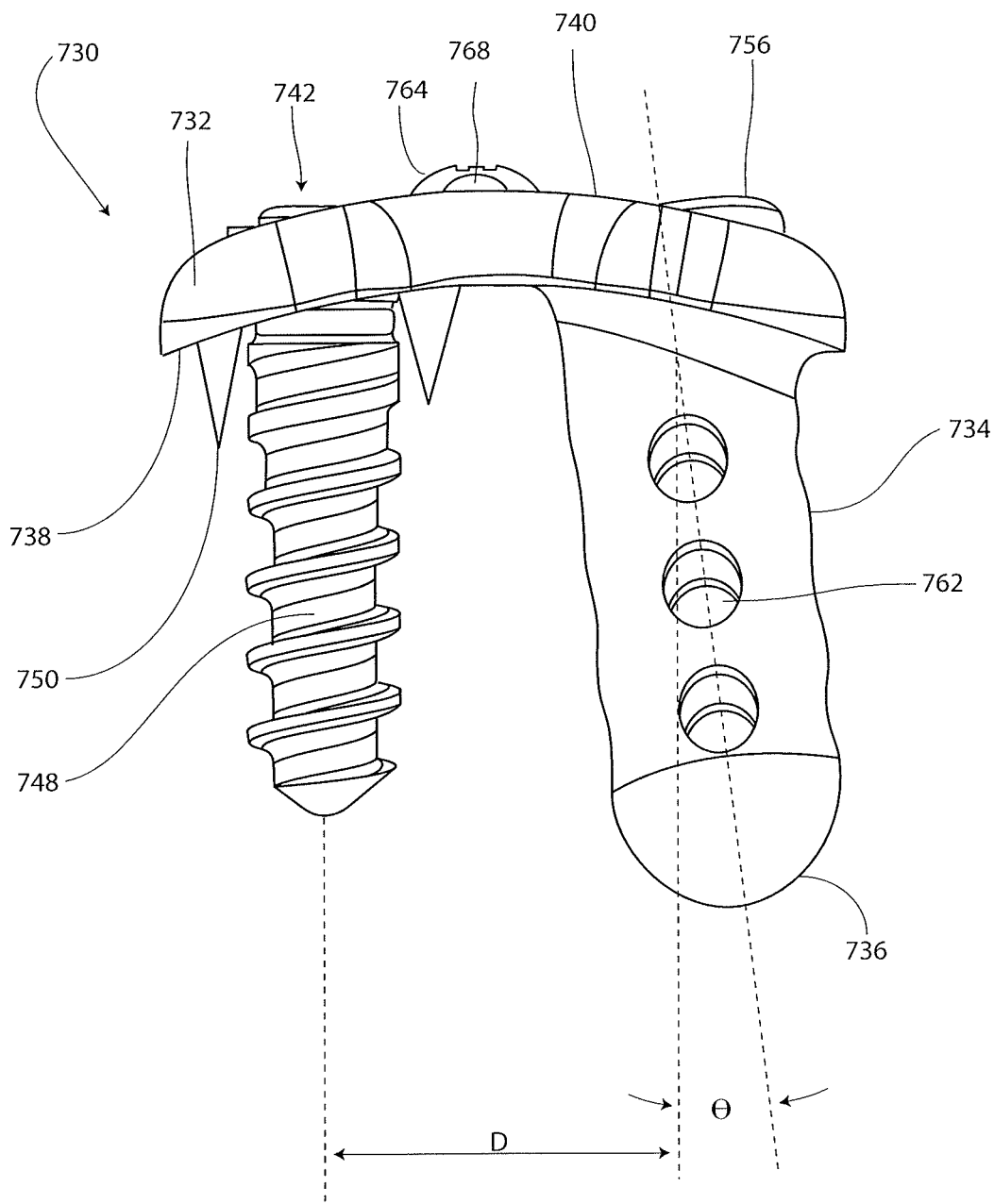

As best seen in FIG. 43, repair implant housing 732 may be configured with a curved posterior surface 738. The curvature of posterior surface 738 may be selected in manner similar to that of the radius of curvature of the posterior surface of tool 700 as previously described. In some embodiments, a series of two or more implants may be provided, each with a different radius of curvature. With this arrangement, a closely fitting implant may be selected to match a particular patient's anatomy. The anterior surface 740 of implant housing 732 may also be curved as shown. All exposed edges and corners may be rounded as shown to avoid interfering with surrounding tissue when implanted.

Figure 45:
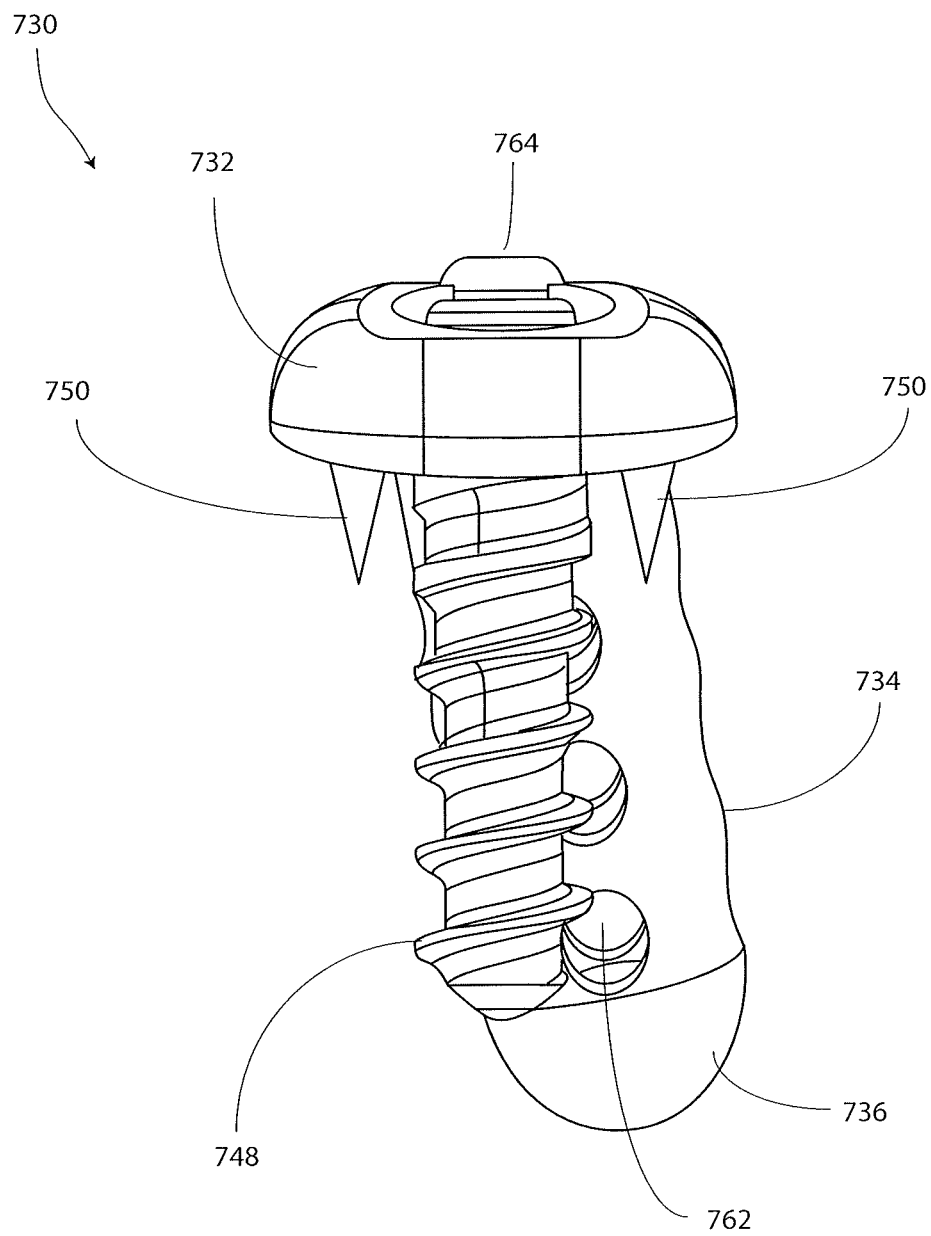

As shown in FIG. 43, plug portion 734 may be angled in the mediolateral direction. In this exemplary embodiment, plug portion 734 is angled about 10 degrees laterally outward to match the angle of previously described trajectory control sleeve 704. Similarly, plug portion 734 may be angled in the craniocaudal direction, as best seen in FIG. 45. In this embodiment, plug portion 734 has an angle of about 10 degrees in the craniocaudal direction to match the craniocaudal angle of sleeve 704.

Figure 41:
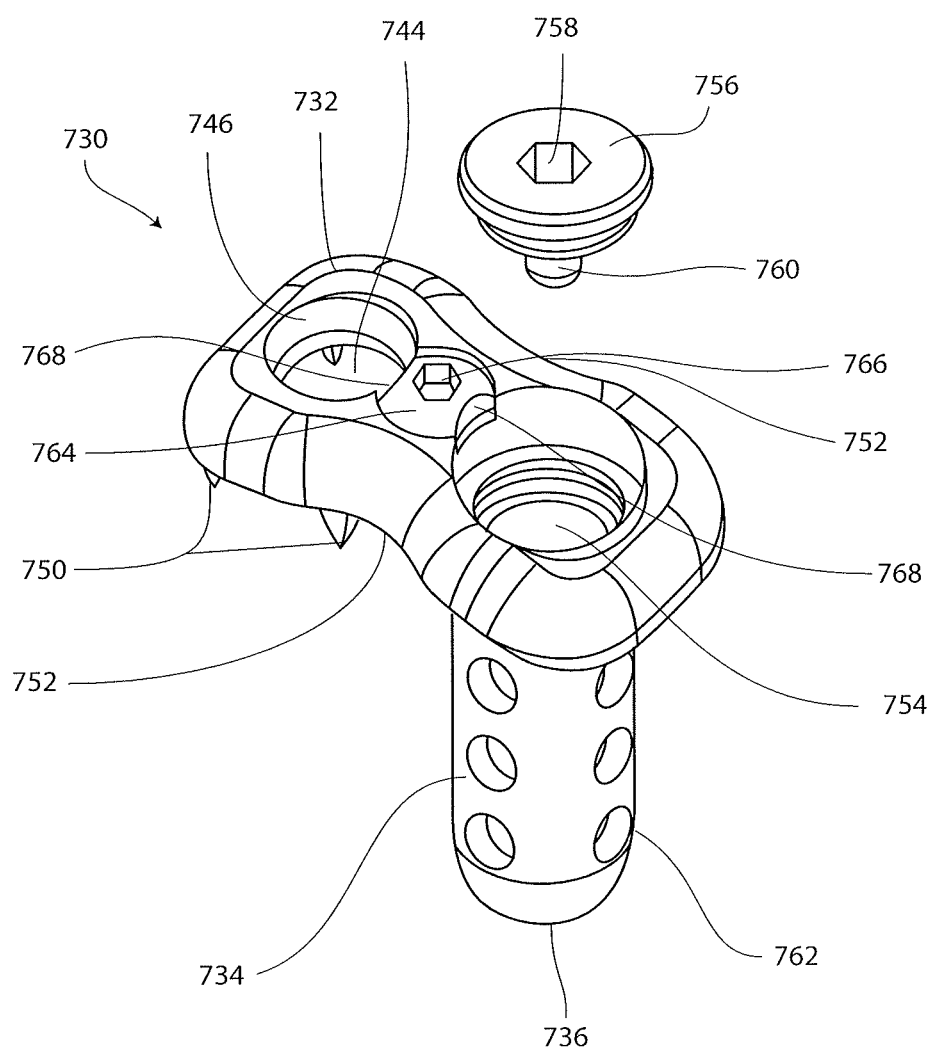
FIGS. 41-45 show various views of a repair implant according to another embodiment.
Figure 42:
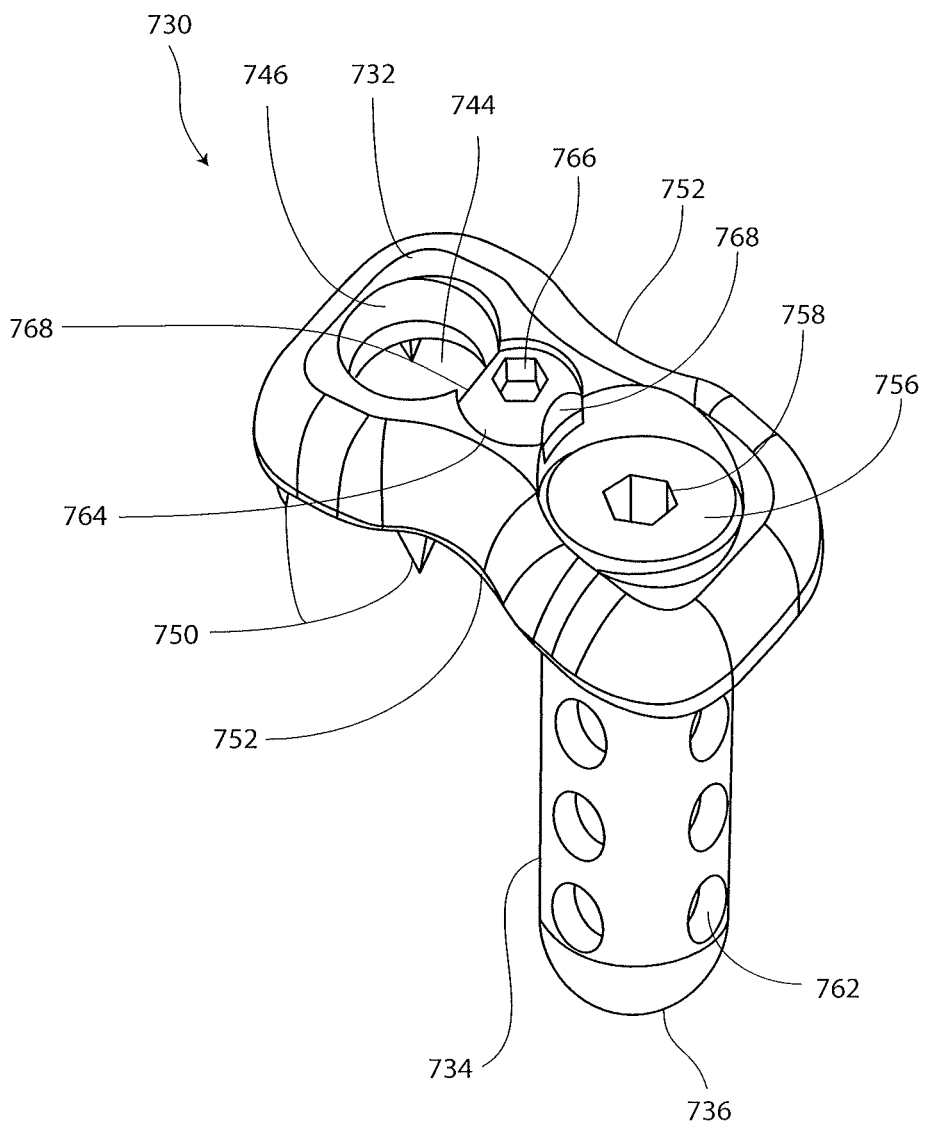
Figure 44:
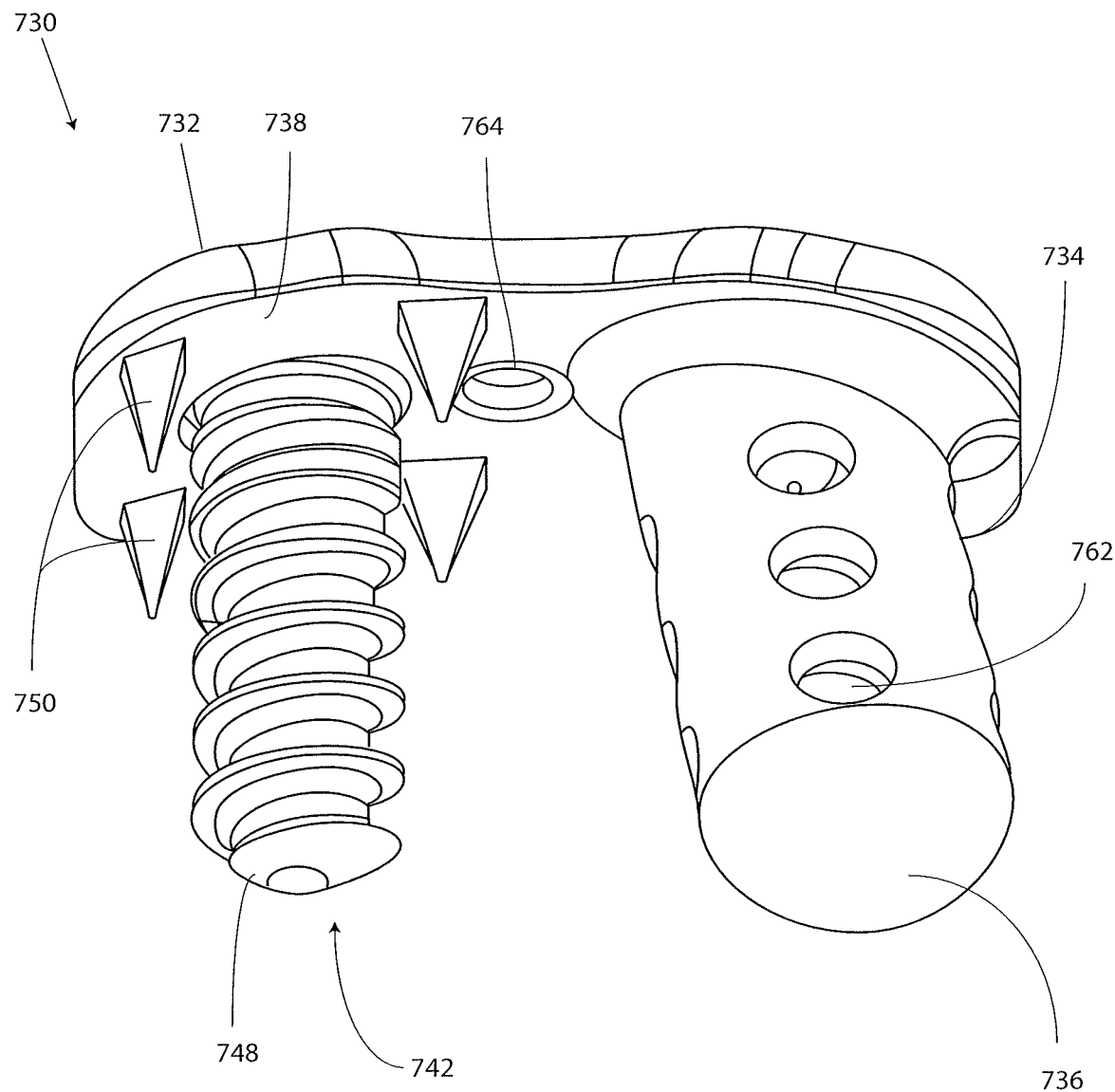

Implant housing 732 may also comprise a fastening portion 742. In some embodiments, fastening portion 742 includes a bore 744 vertically through housing 732, as shown in FIG. 41. The anterior end of bore 744 may be provided with a countersunk portion 746 for mating with the head of a bone screw. An exemplary bone screw 748 is shown in FIGS. 43-45 inserted through the bore. In some embodiments, screw 748 is a variable angle screw. As shown in FIG. 43, the axis of fastening portion 742 may be offset from the axis of plug portion 734 where it passes through the posterior surface 738 of housing 732 and into the anterior surface of a vertebral body. In some embodiments, this offset distance D, shown in FIG. 43, is configured to be the same as the predetermined distance D of tool 700, shown in FIG. 39. In the current embodiment shown in FIGS. 38-59, the compound angle and diameter of plug portion 734 matches the compound angle and diameter of an access channel formed by tool 700 in a vertebral body. With this configuration, plug portion 734 may be inserted into the access channel, and implant screw 748 may be threaded into the same screw hole formed in the vertebral body to temporarily receive the previously described distal end 716 of fastening device 714, as will be more fully described below.

As best seen in FIG. 44, one or more sharp protrusions 750 may be provided on the posterior surface 738 of implant 730. In this exemplary embodiment, the locations of protrusions 750 are chosen to match the relative locations of protrusions 720 of tool 700, so as to use the same indentions in the vertebral body formed by protrusions 720. Such an arrangement can help align implant 730 when it is being placed on the vertebral body. Protrusions 750 of implant 730 may be made larger than the protrusions 720 of tool 700 to ensure that they fully engage the vertebral body. Implant housing 732 may be provided with recesses 752 on opposite longitudinal sides, similar to previously described recesses 722 of tool 700. Recesses 752 can aid the surgeon in gripping and aligning implant 730.

In some embodiments, the plug portion of repair implant 730 is solid. The outer diameter of the plug portion may be slightly tapered as shown to assume a compressive fit in the bone defect. As best seen in FIG. 41, plug portion 734 may include a hollow cavity 754 that extends toward the distal end 736 of plug portion 734 and is open at the proximal end. A removable cap 756 may also be provided for closing the hollow cavity 754. External threads may be provided on cap 756 for engaging with internal threads in implant housing 732 as shown. In other embodiments, a bayonet, cam or other connection may be provided to couple the cap to implant housing 732. A keyed socket 758 may be provided in cap 756 for receiving a mating driver tip for tightening cap 756 on housing 732. Cap 756 may include a downwardly projecting protrusion 760. A similar upwardly projecting protrusion (not shown) may be provided at the bottom of hollow cavity 754. In some embodiments, plug portion 734 may be formed of a porous material. In the embodiment shown, holes 762 are provided between hollow cavity 754 and the outer surface of plug portion 734.

As with the bone cages of previously described embodiments, autologous, allogeneic, or synthetic bone fragments and/or other osteogenic or therapeutic material may be placed into hollow cavity 754. In some embodiments, this material is compressed when cap 756 is placed on implant housing 732 and tightened. In some embodiments, downwardly projecting protrusion 760 and/or a similar upwardly projecting protrusion assist in moving the compressed material radially outward through holes 762. Holes 762 allow intimate contact between the material in cavity 754 and the surrounding bone tissue of the vertebral body.

Figure 59:
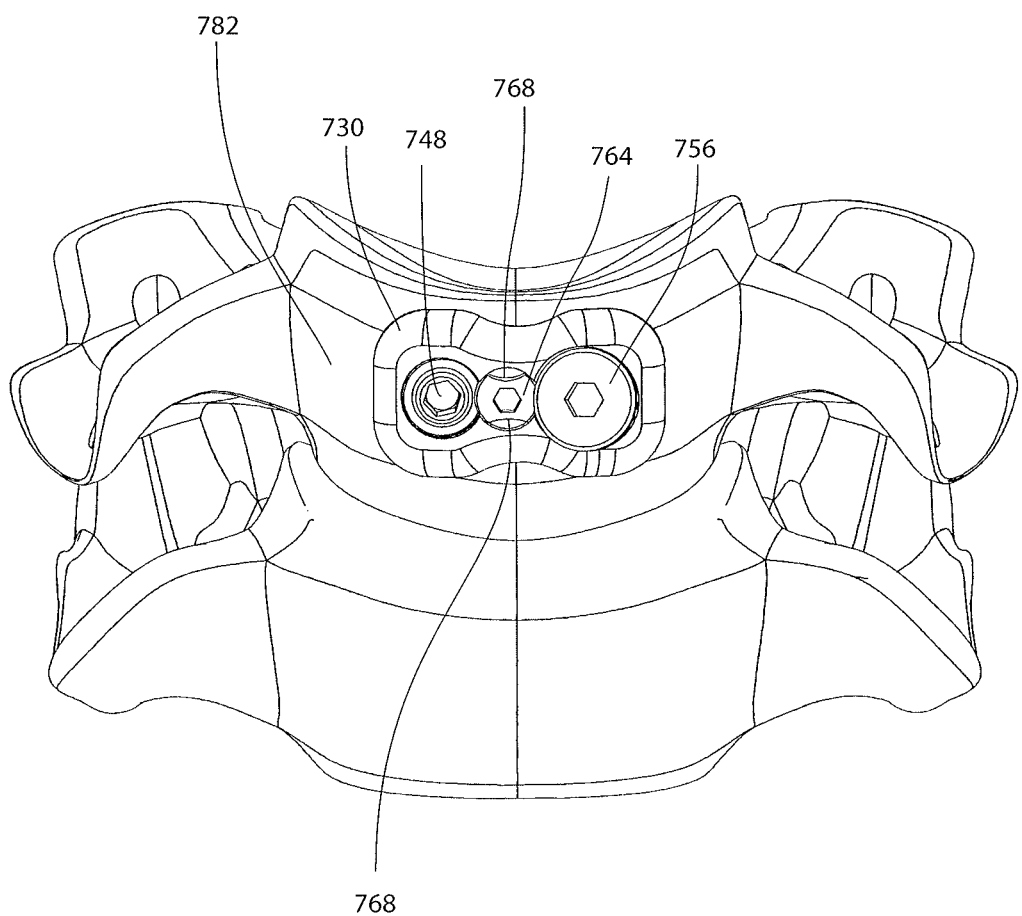

A retainer may be provided to lock cap 756 in place. In some embodiments, the retainer is movable between an unlocked position and a locked position, with the retainer covering at least a portion of cap 756 when in the locked position. In some embodiments, a similar retainer may be provided for preventing bone screw 748 from backing out of the bone. In the embodiment shown, a single retainer 764 is used to secure both cap 756 and bone screw 748. In this embodiment, retainer 764 comprises an element that is rotatably attached to implant housing 732 in a recess within the anterior surface of housing 732. Retainer 764 has a keyed socket 766 within its anterior face for receiving a driver tip to rotate the retainer. Retainer 764 may be rotated between an unlocked position, as shown in FIG. 41, and a locked position, as shown in FIG. 59. When in the unlocked position, curved cutouts 768 in the periphery of retainer 764 line up with the bores that receive cap 756 and screw 748. Once cap 756 and screw 748 are in place, retainer 764 may be rotated about 90 degrees such that solid portions of its periphery cover a portion of both cap 756 and screw 748, thereby preventing their removal until such time that retainer 764 may be unlocked.

In some embodiments, some or all of the components of implant 730 are made from a polymer, a metal, metallic alloy, or a ceramic. Suitable polymeric materials include polyetheretherketone (PEEK), PEEK-reinforced carbon fiber, and hydroxyapatite-reinforced PEEK. Suitable metals include titanium. Constructing the implant from a polymer may allow for easy monitoring of in-growth into the implant after the procedure. Using a polymer also may also make the implant easily cuttable and/or removable. In some embodiments, components made be constructed of bio-absorbable material(s). In some embodiments, the distal tip 736 of the plug portion 734 may include a tantalum pin for ease of imaging the depth of the implant into the vertebral body.

Referring to FIGS. 46-59, an inventive surgical procedure for creating, using, and repairing a transcorporal access channel using previously described trajectory control tool 700 and implant 730 will now be described. This exemplary procedure may be used, for example, to create an access channel with a prescribed trajectory through a cervical vertebral body, from an anterior surface entry to a prescribed posterior surface opening on the vertebral body. In some embodiments, removing vertebral bone material to create the posterior surface opening may be the ultimate objective of the procedure. In other embodiments, the access channel may then be used to perform a surgical procedure adjacent the posterior surface opening of the vertebral body. For example, instruments may be inserted through the access channel for decompressing a neural element, such as an individual nerve root, a spinal cord, a cauda equine, or a combination thereof. The channel may be used to access a portion or the whole of a herniated disc, an osteophyte, a thickened ligament, a tumor, a hematoma, a degenerative cyst, or any other compressing pathology.

Figure 46:
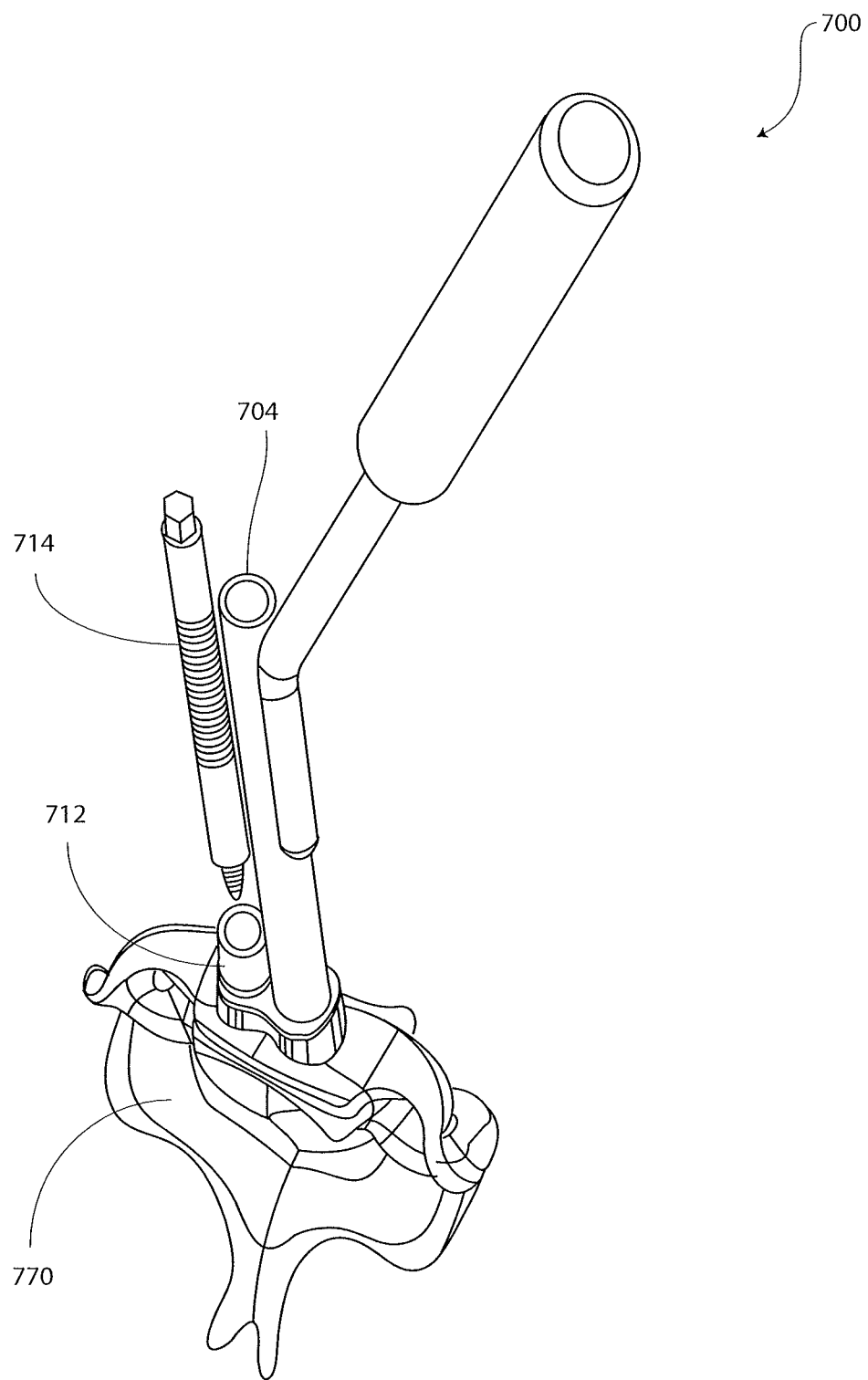
FIGS. 46-59 show various views of a surgical procedure for creating, using, and repairing a transcorporal access channel using the trajectory control tool of FIGS. 38-40 and the repair implant of FIGS. 41-45.
Figure 47:
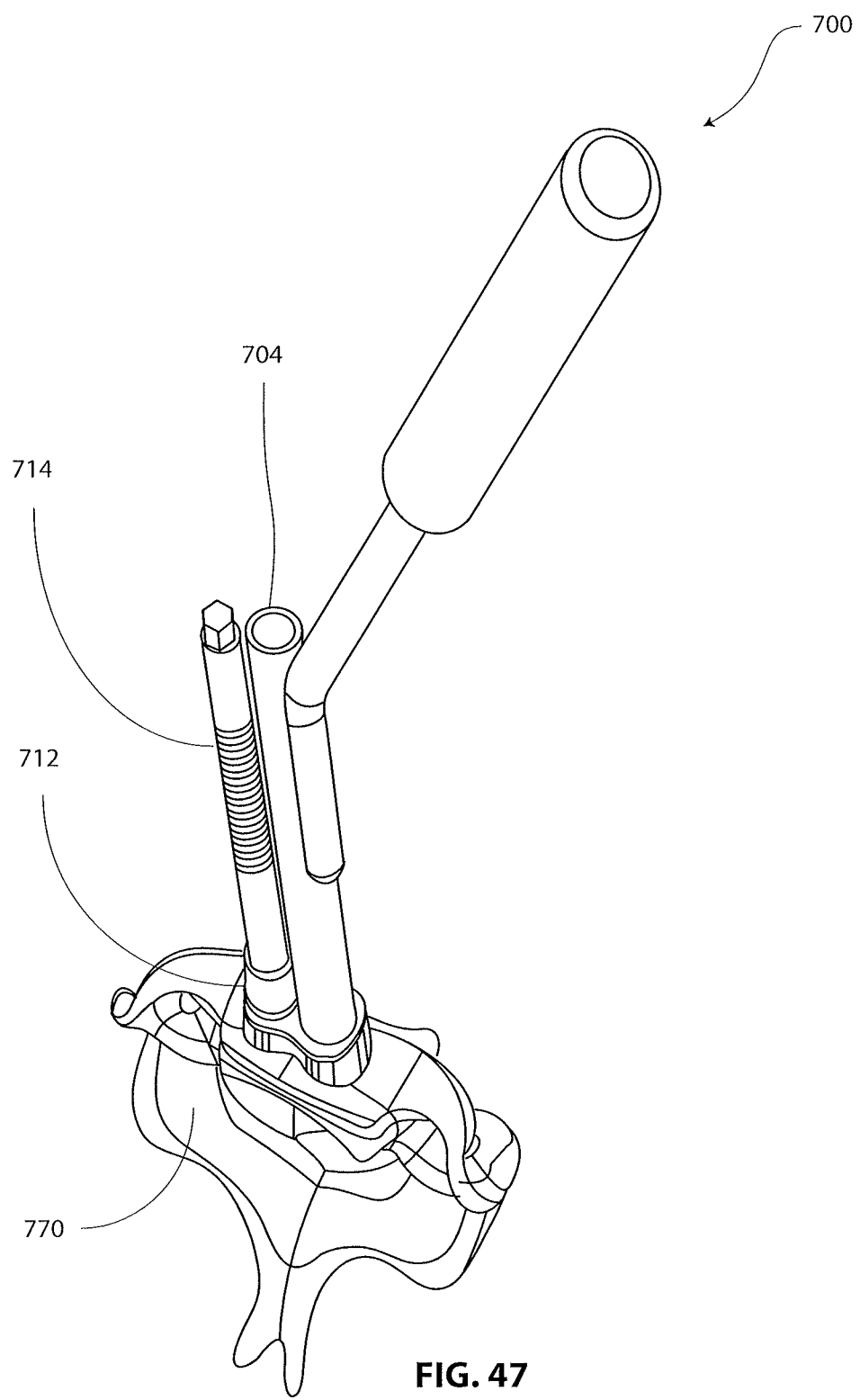

In this exemplary embodiment, an incision is first made adjacent to the anterior surface of a vertebral body 770 through which an access channel is to be created. Retractors may be used to move soft tissue to further expose the anterior surface of vertebral body 770. Tool 700 may then be placed on the anterior surface as shown in FIG. 46, and may be centered mediolaterally and craniocaudally on the anterior surface. A fastening screw hole may be prepared by inserting a drill and/or a tap (not shown) into fastener sheath 712 of tool 700. In some embodiments, these screw hole preparation steps may be omitted. Fastening tool 714 may then be aligned with fastener sheath 712, as shown in FIG. 46. The distal end 716 of fastening tool 714 may be inserted through fastener sheath 712 and threaded into vertebral body 770, as shown in FIG. 47. As previously described, fastening tool 714 may have a flexible mid or proximal portion to allow a driver or handle to be attached and operated. The proximal ends of both the fastening tool 714 and trajectory control sleeve 704 may extend outside of the patient for increased accessibility. In some embodiments, fastening tool 714 may be permanently coupled to trajectory control tool 700, or may be inserted into fastener sheath 712 prior to tool 700 being inserted into the surgical site. The above steps temporarily attach trajectory control tool 700 to vertebral body 770.

Figure 48:
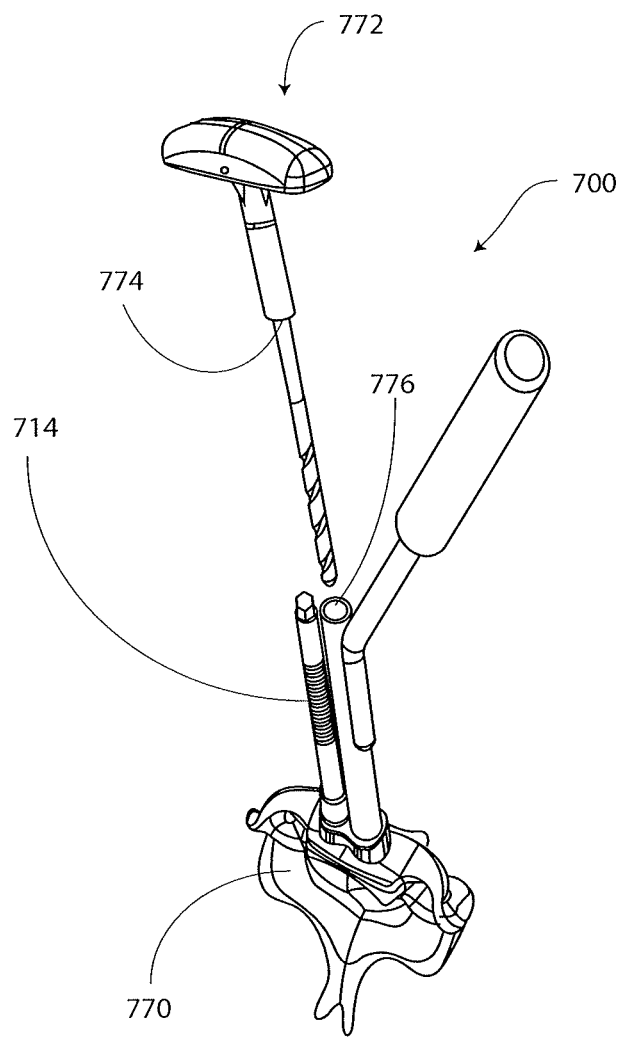
Figure 49:
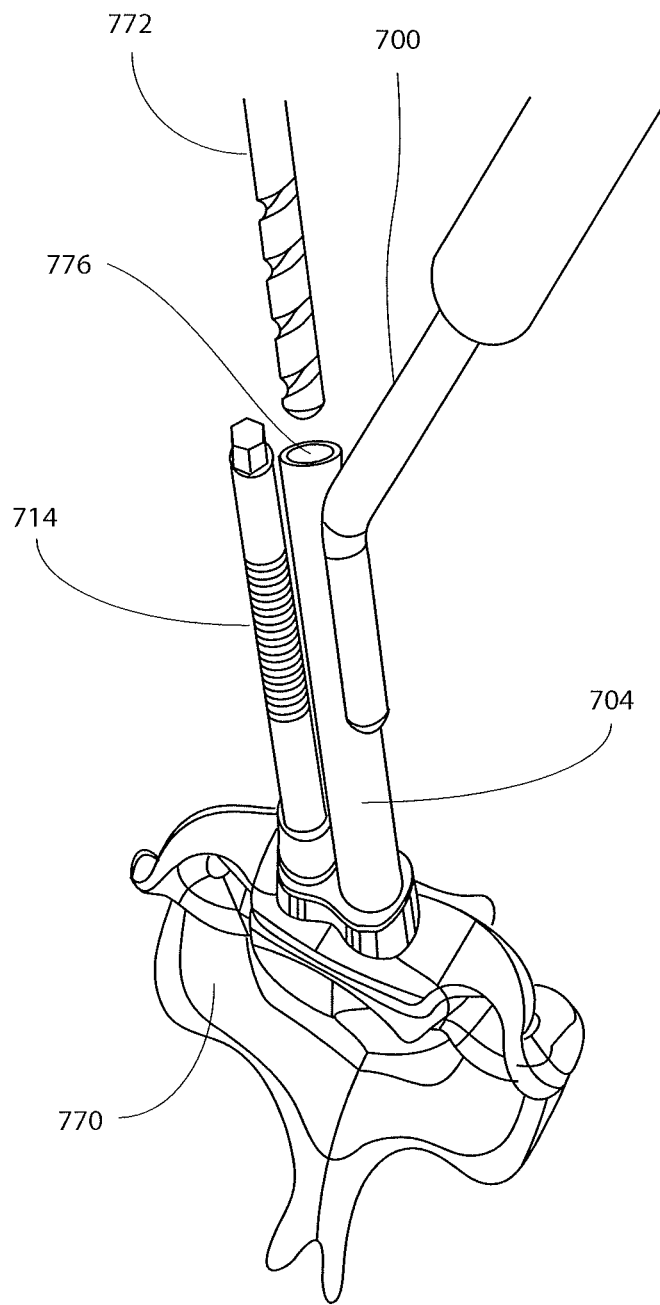
Figure 50:
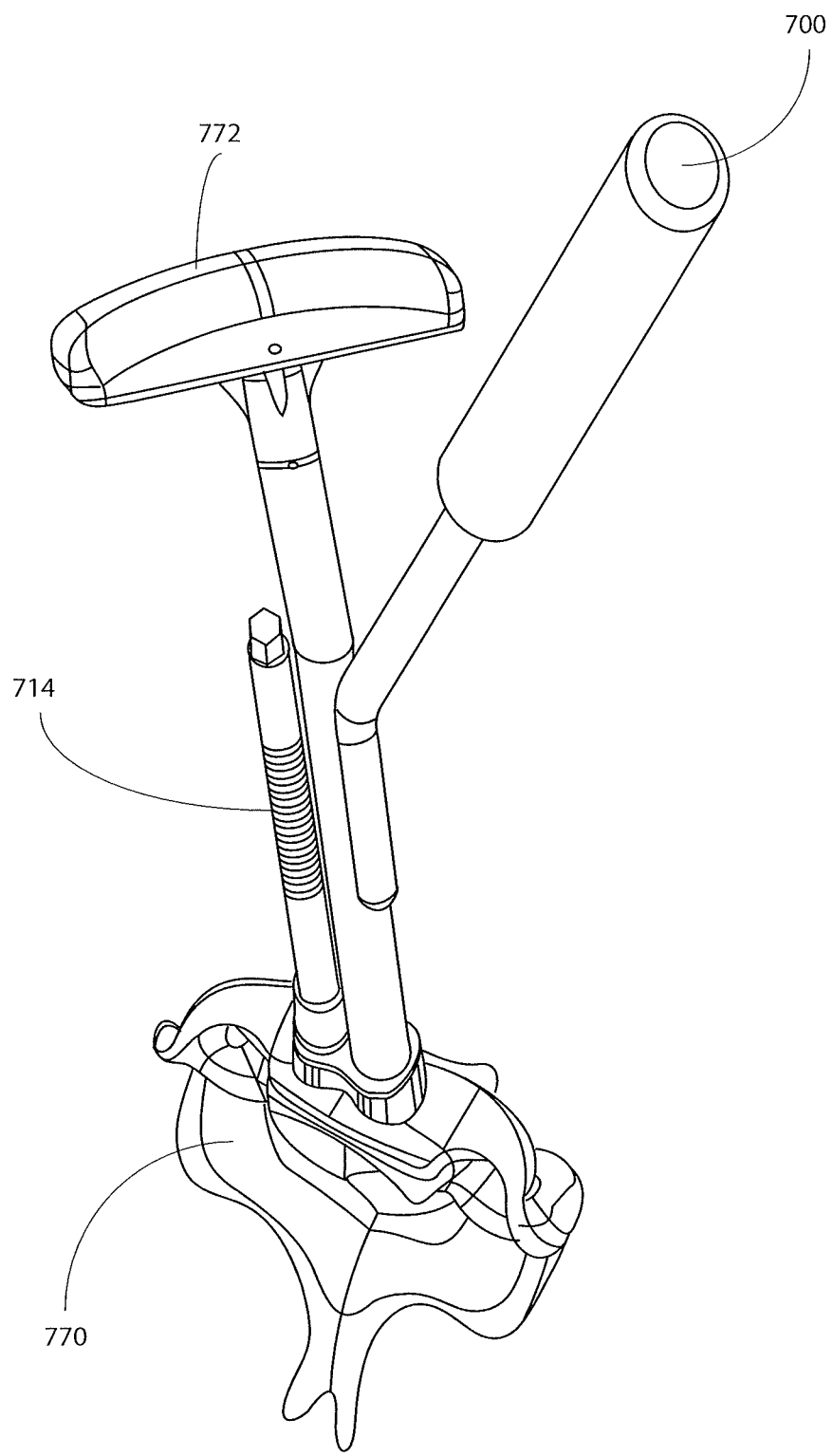

As shown in FIGS. 48 and 49, a bone cutting tool 772 may be aligned with trajectory control sleeve 704 for inserting therein. Tool 772 may have a handle as shown, or be motor driven. Although a drill bit is shown, a mill, burr, trephine, reamer, saw and/or other bone cutting tool may be inserted into sleeve 704 to create an access channel through vertebral body 770. An accurately controlled end stop surface 774 may be provided on bone cutting tool 772 for engaging the proximal surface 776 of trajectory control sleeve 704, as shown in FIG. 50, to control the depth of the access channel being created in the vertebral body 770. In some embodiments, the position of end stop surface 774 is adjustable.

In some embodiments, a series of drills are provided. Each drill has the same diameter shank to match the nominal inside diameter of trajectory control sleeve 704. However, each drill has a different cutting diameter at its distal end, ranging from 2 to 7 mm. Drills of the same cutting diameter may also be provided with different cutting depths. In some embodiments, one or more drills are provided that each has more than one cutting diameter. With this arrangement, a stepped access channel may be created having a smaller diameter at its distal end (adjacent the posterior side of the vertebral body), and a larger diameter at its proximal end (adjacent the anterior side of the vertebral body). This allows more room at the proximal end for angling tools through the access channel, and allowing for a larger repair implant to reside in the proximal end of the channel. It also prevents excess material from being removed from the posterior side of the vertebral body which might excessively weaken it and/or require additional healing time. In some embodiments, an implant with a stepped diameter is provided to fill the entire access channel. A series of different repair implants may be provided with any of the above drill sets to allow a surgeon to select a particular approach depending on the anatomy and pathology of each patient.

Figure 51:
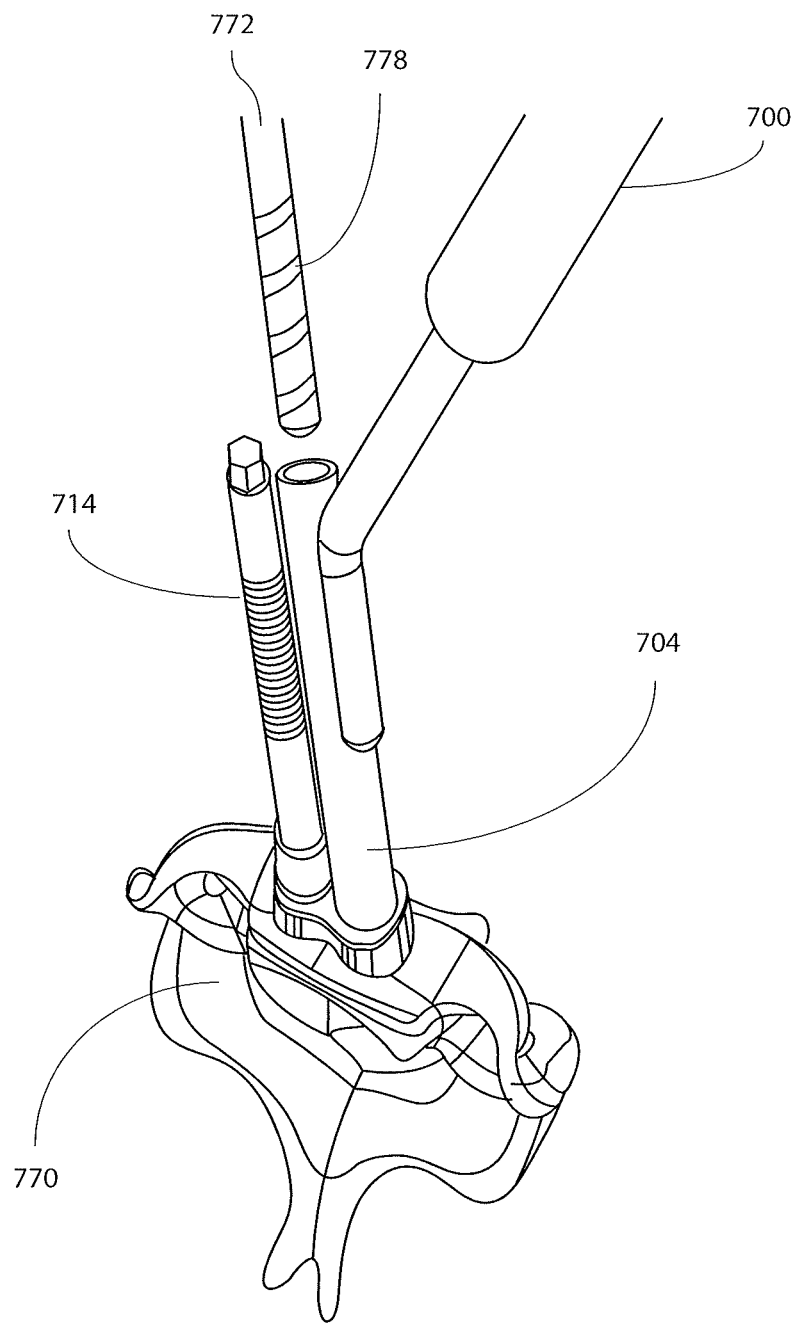

FIG. 51 shows bone cutting tool 772 being removed from trajectory control sleeve 704. Tool 772 and sleeve 704 may be configured to cooperate to retain for harvesting the bone tissue 778 that is removed when creating the access channel. In some embodiments, bone tissue 778 is removed from the flutes of cutting tool 772 by tapping tool 772 over a collection tray, or by picking the tissue 778 from the flutes. A positive rake angle may be provided on the bone cutting tool 772 to enhance bone tissue harvesting.

Figure 52:
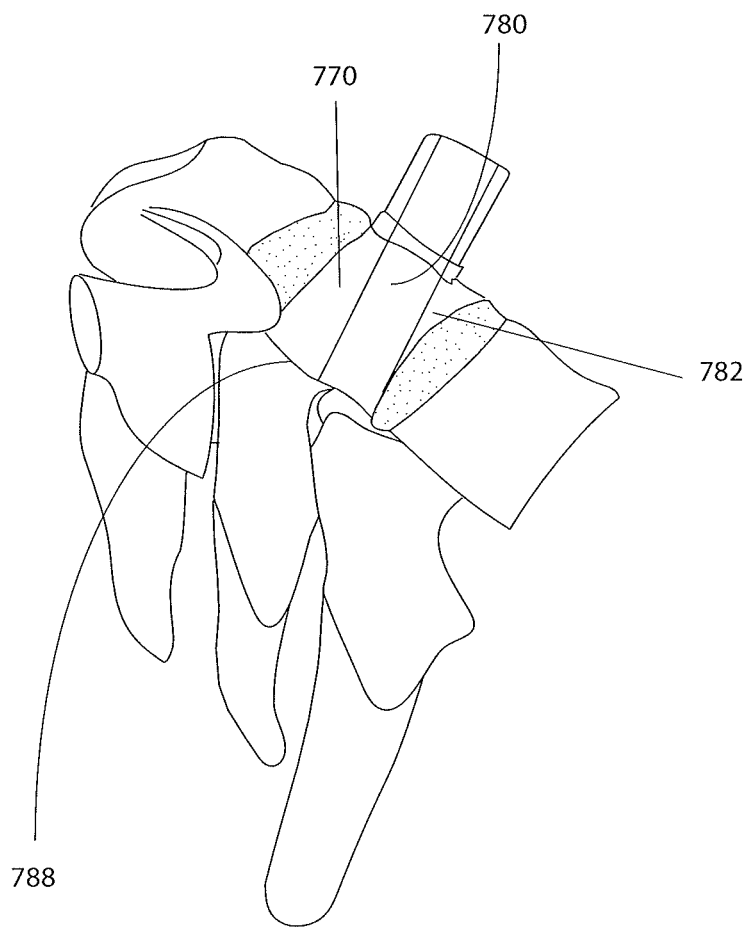
Figure 53:
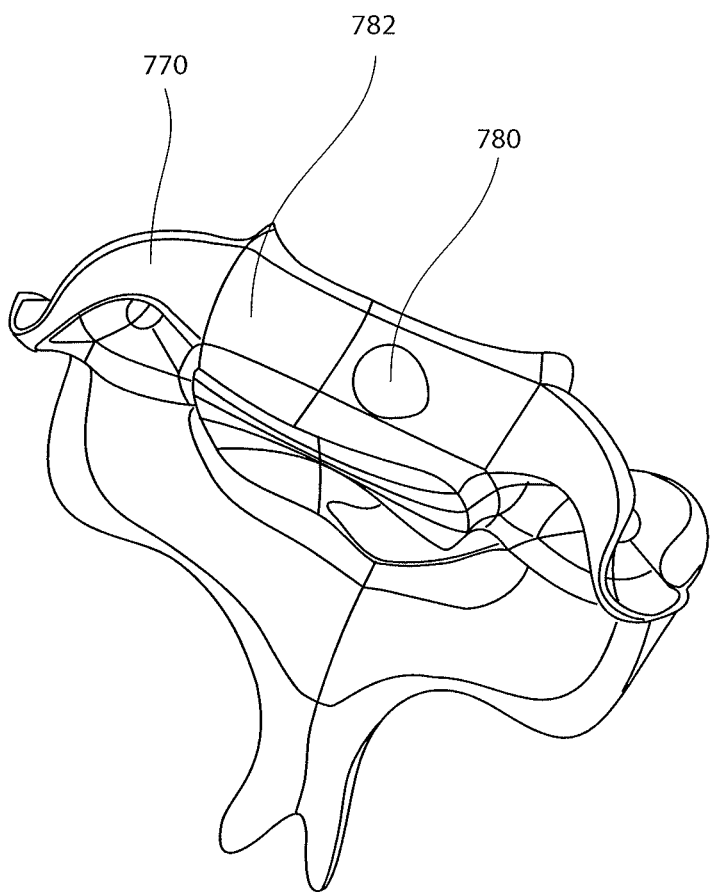
Figure 54:
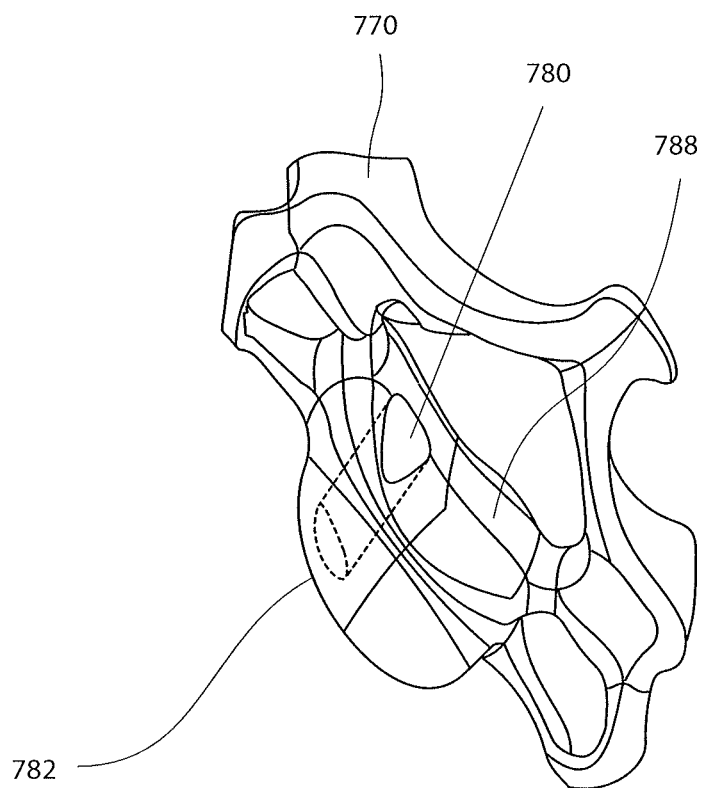

FIGS. 52-54 show various views of the access channel 780 created through vertebral body 770 by trajectory control tool 700 and bone cutting tool 772 after the tools have been removed. Tool 700 is removed from vertebral body 770 by unscrewing fastening tool 714 in the reverse manner in which it was tightened. As previously described, access channel 780 is created with a prescribed trajectory through vertebral body 770, from an anterior surface entry to a prescribed posterior surface opening on the vertebral body. In some embodiments, tools 700 and 772 are used to create an access channel that stops just short of the posterior surface, and then the posterior opening of the channel is created by manually picking, chipping or otherwise removing the final bone tissue at the end of the channel. In some embodiments, this can create a desirable flared out channel opening on the posterior surface of vertebral body 770, thereby providing increased access to adjacent target pathology.

As previously described, a decompression or other surgical procedure may now be performed through access channel 780. In some embodiments one or more kerrisons, rongeurs, curettes, nerve hooks and/or other elongated instruments are placed through access channel 780 to perform the procedure.

Referring to FIGS. 55-59, exemplary steps for repairing access channel 780 are shown. Prior to inserting plug portion 734 of repair implant 730 into access channel 780, osteogenic and/or other therapeutic material may be placed into plug portion 734, in any manner previously described in relation to bone repair device 905 or plug portion 734.

Figure 55:
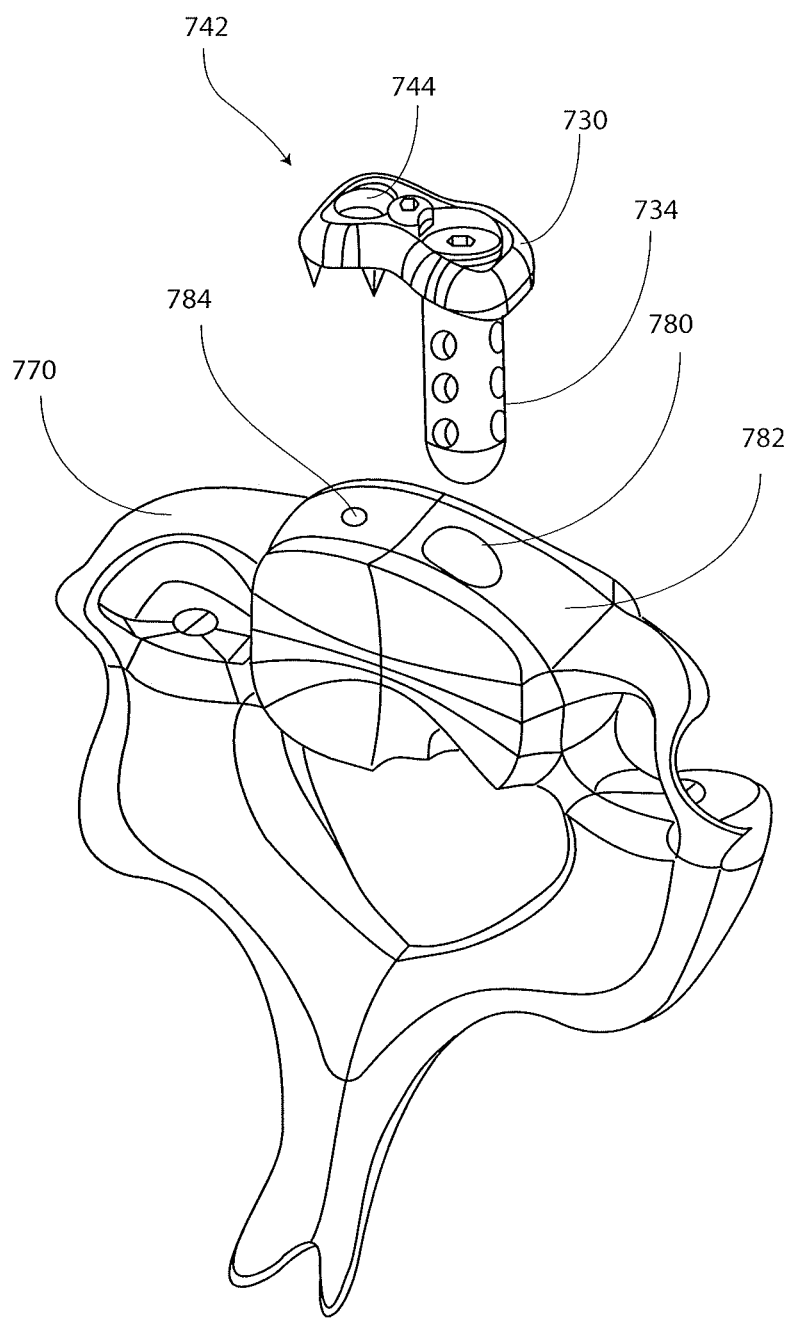

As shown in FIG. 55, repair implant is introduced to the anterior surface 782 of vertebral body 770 by aligning plug portion 734 over access channel 780 and aligning bore 744 of fastening portion 742 over the screw hole 784 in vertebral body 770. Screw hole 784 was formed when the distal end 716 of fastening tool 714 was inserted into vertebral body 770 to temporarily attach trajectory control tool 700. In some embodiments, screw hole 784 may not have been previously formed, and may be formed at this time.

Figure 56:
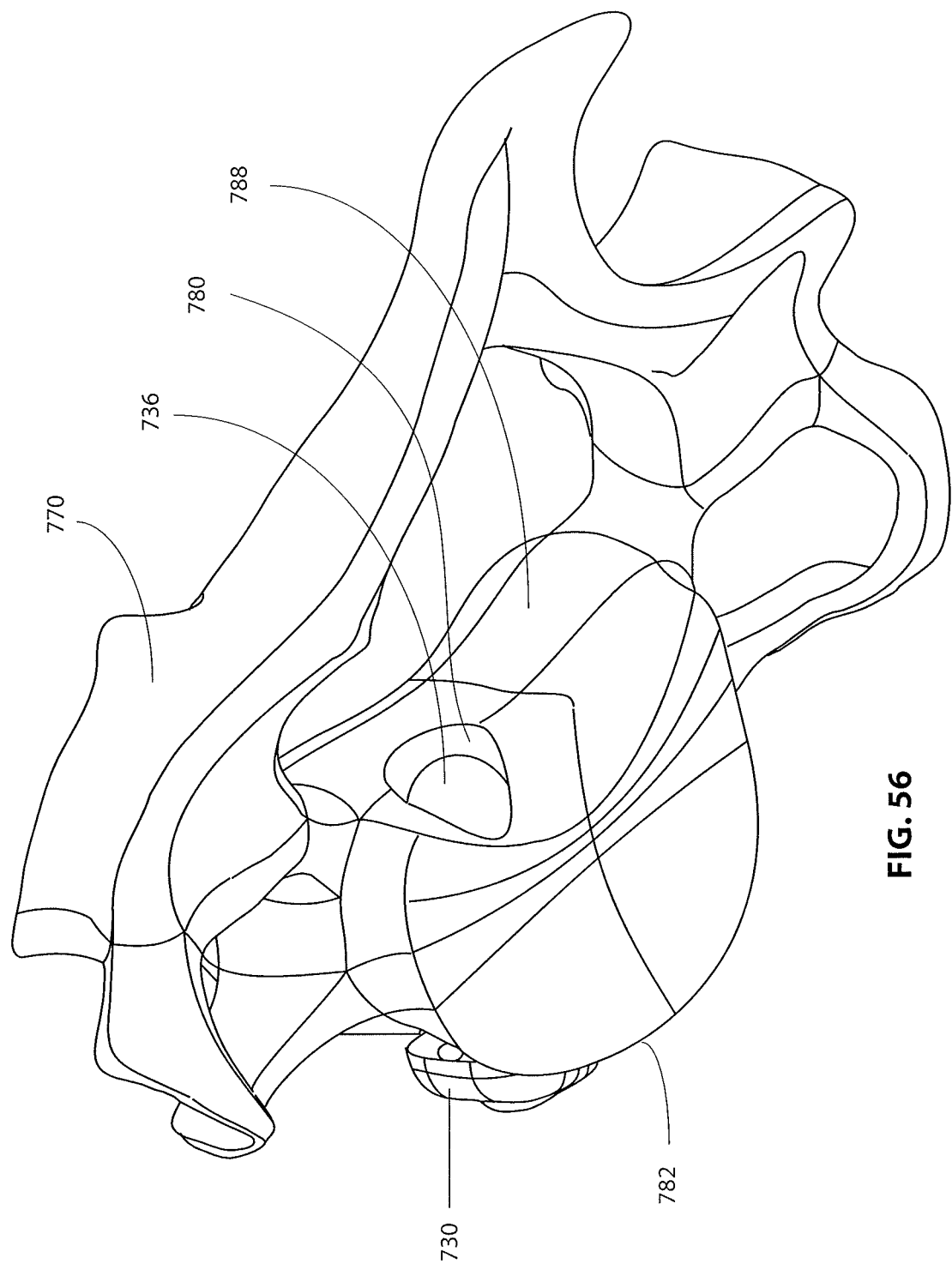

As shown in FIG. 56, plug portion 734 of implant 730 may be introduced into access channel 780 until its distal end 736 is adjacent to the opening 786 in the posterior surface 788 of vertebral body 770.

Figure 57:
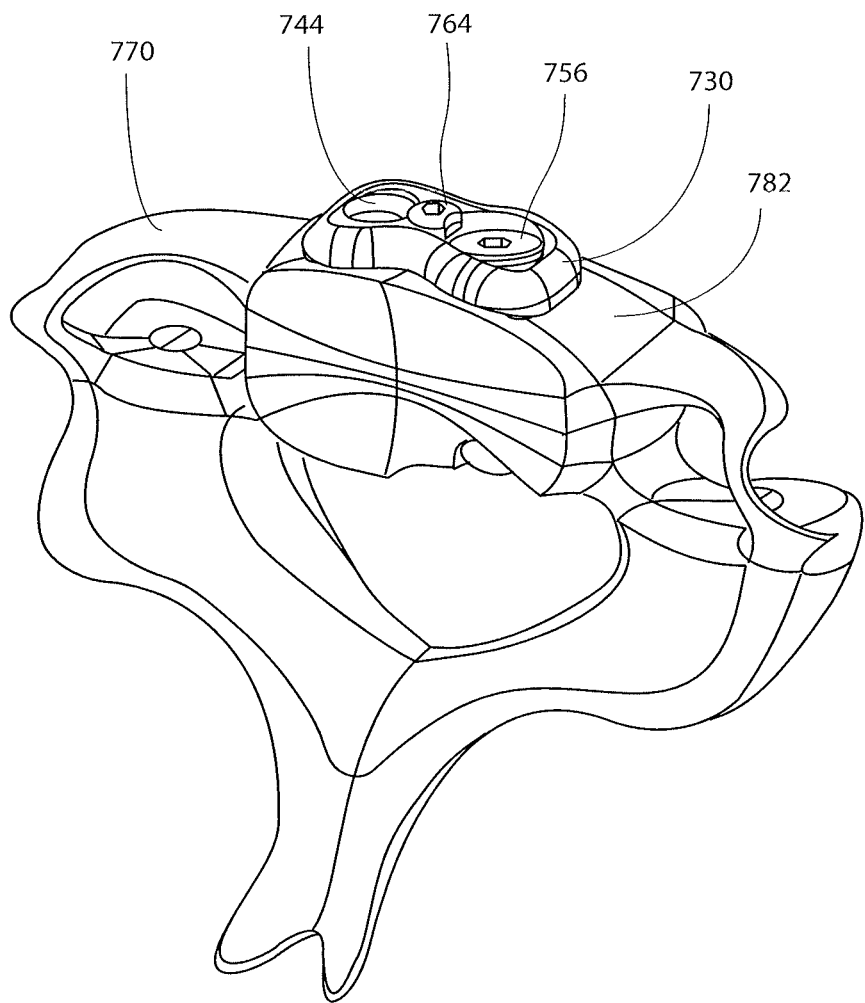

Referring to FIG. 57, implant is shown in its permanent position on the anterior surface 782 of vertebral body 770.

Figure 58:
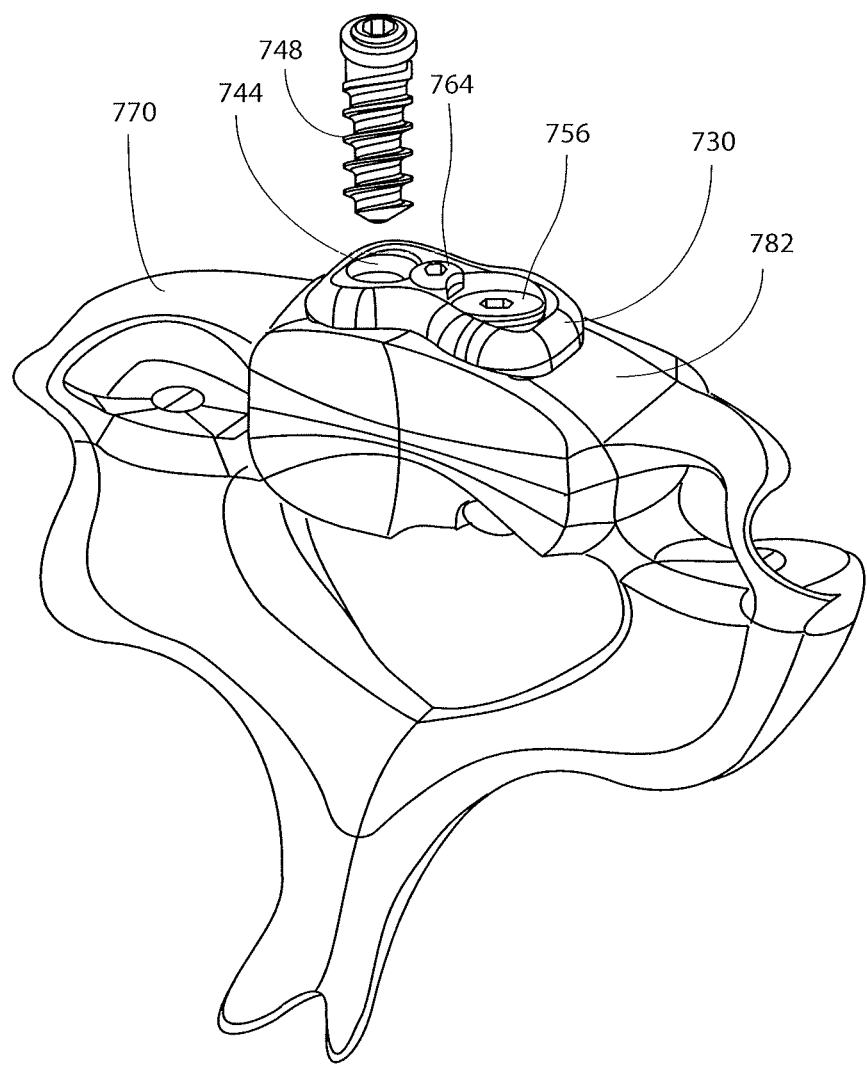

Referring to FIG. 58, bone screw 748 is shown being inserted into bore 744 of repair implant 730. At this point retainer 764 is in an unlocked position.

Referring to FIG. 59, repair implant 730 is shown secured to the anterior surface 782 of vertebral body 770 by screw 748. Once implant 730 is in place, cap 756 may be further tightened to force osteogenic material from within implant 730 into intimate contact with the walls of the access channel to promote rapid more rapid bone ingrowth and healing. Retainer 764 may be rotated into the locked position as shown to cover a portion of screw 748 and cap 756 and thereby prevent them from backing out. With the installation of implant 730 complete, the access incision may then be closed.

Figure 60:
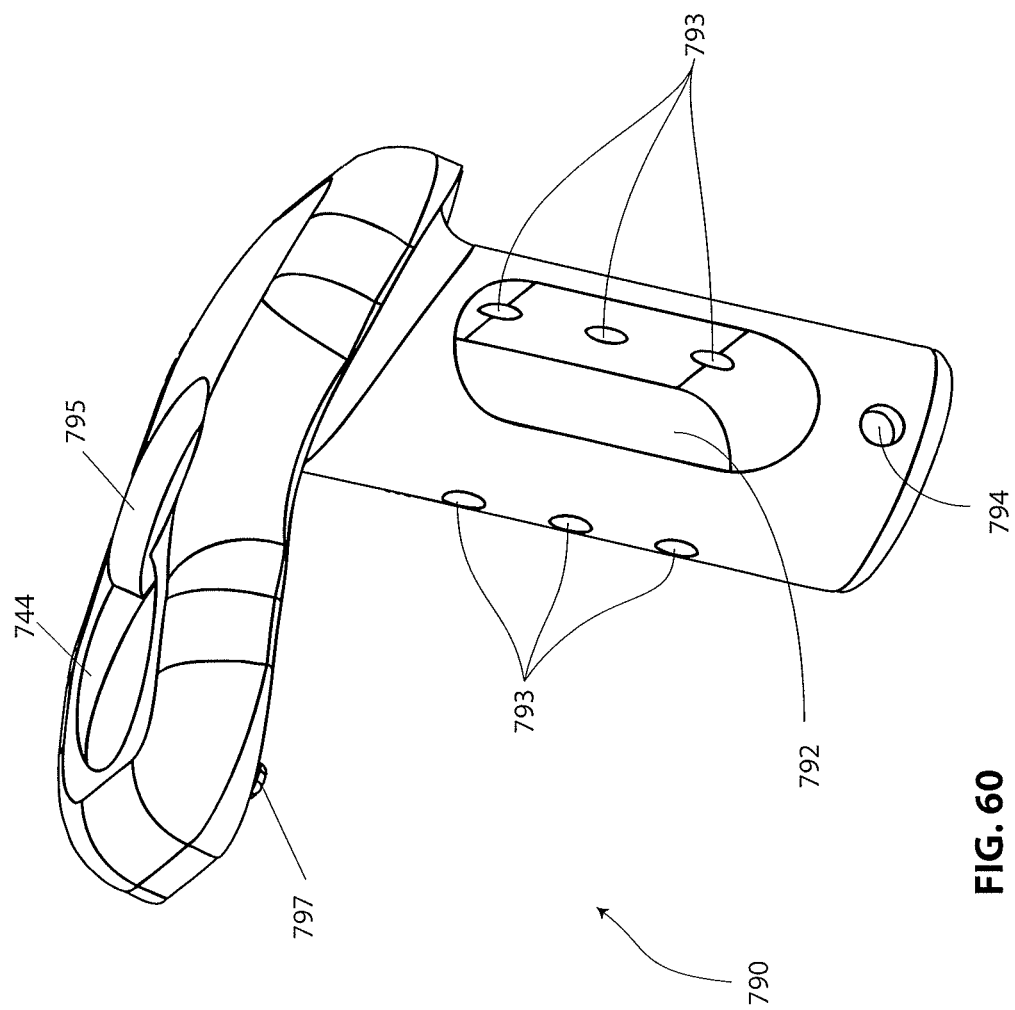
FIGS. 60-62 show various views of a repair implant according to yet another embodiment.
Figure 61:
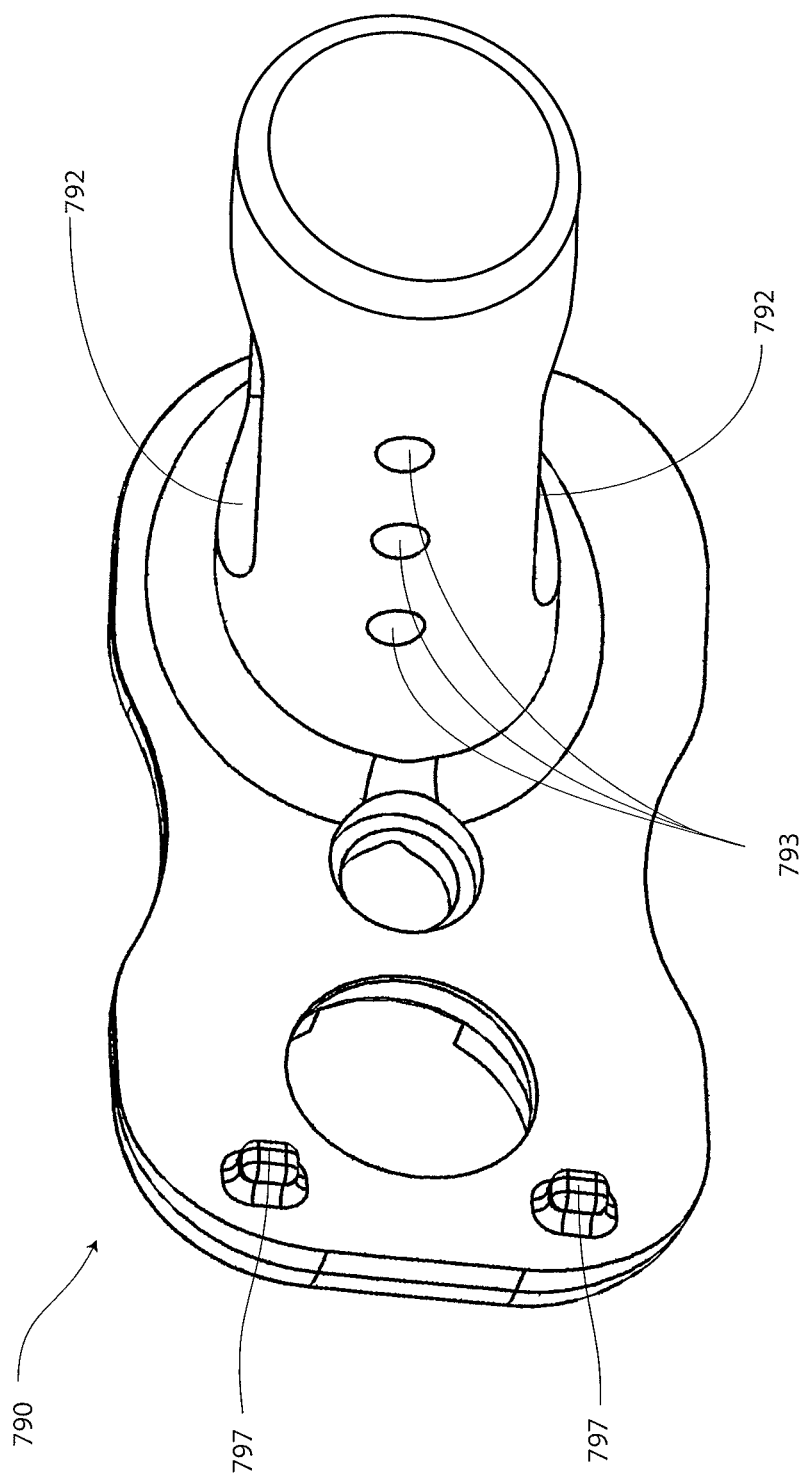
Figure 62:
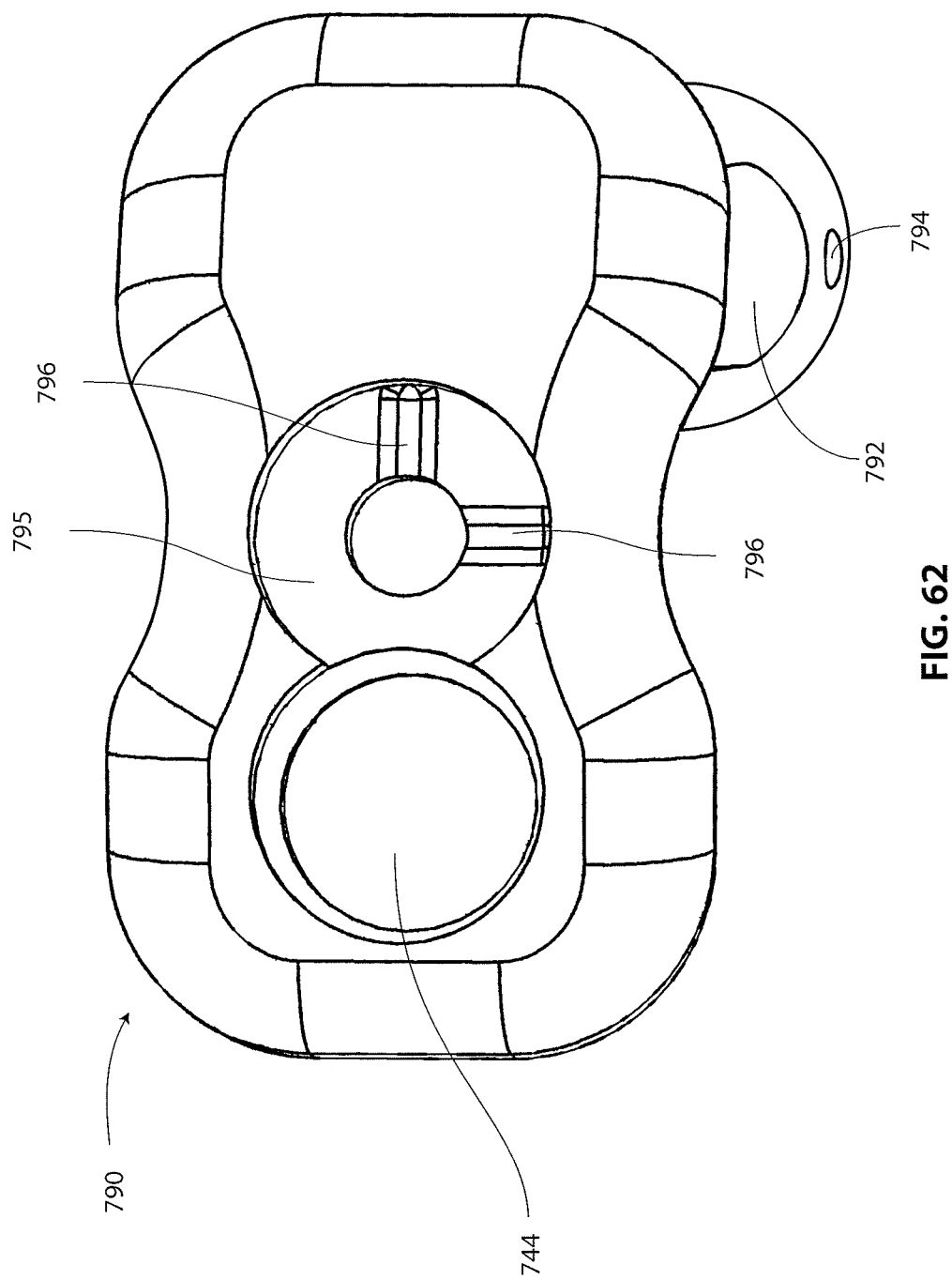

Referring to FIGS. 60-62, another embodiment of repair implant is shown. Repair implant 790 is constructed and functions in a similar manner to previously described repair implant 730. Implant 790 includes a central graft slot 792 extending transversely through the plug portion of the implant. In this exemplary embodiment, graft slot 792 has openings in the cephalad and caudal directions. Transverse holes 793 may be provided in the medial and lateral directions as shown, connecting a mid-portion of graft slot 792 with the exterior surface of the plug portion. Transverse hole 794 may be provided across the bottom of the plug portion for receiving a tantalum pin (not shown.) Such a pin may aid in imaging to confirm the depth of the plug portion in the access channel.

As best seen in FIG. 62, repair implant 790 in this exemplary embodiment does not include an opening or a removable cap over the plug portion, as any osteogenic material is loaded from the side of the plug portion directly into central graft slot 792. A recess 795 may be provided in the top of implant 790 for rotatably receiving a screw retaining member such as previously described retainer 764 shown in FIG. 59. Two detent slots 796 may be provided in the bottom of recess 795 for alternately receiving a mating protrusion (not shown) on the underside of retainer 764 for holding the retainer in either the locked or unlocked position. As previously described, when retainer 764 is in the locked position, it covers a portion of a screw installed in bore 744 to keep it from backing out of the bone.

As best seen in FIG. 61, blunt projections 797 may be provided on the underside of the implant housing for assisting in securing implant 790 to a vertebral body. Blunt protrusions can allow easier positioning of the implant relative to the bone before tightening the securing screw.

In some situations, repair implant 790 provides greater ease of use in the operating room. Graft material may be packed into a single large open slot 792 instead of being packed through a circular opening on top of the implant. Additionally, no securing cap is needed to retain the graft material, which can eliminate secondary assembly in the operating room. Furthermore, there is no cap to potentially come lose in the wound post-operatively. Additional advantages include ease of manufacture, since there are fewer parts to manufacture and no high tolerance threads to form. The large openings of slot 792 provide large graft contact areas, which promote faster and more complete bone ingrowth during the post-operative healing process.

What is claimed is:

1. A surgical system to form and repair an access channel through a vertebral body, the channel having an anterior surface entry and a posterior surface opening, the system comprising:
    a trajectory control tool comprising a fastening portion configured to secure the tool to the anterior surface of the vertebral body, the tool further comprising a trajectory control sleeve configured to receive at least a portion of a bone cutting tool, the sleeve configured to guide the cutting tool to form the access channel with a trajectory from the anterior entry to the posterior surface opening, the fastening portion configured to be laterally spaced apart from the sleeve by a predetermined distance on the anterior surface of the vertebral body; and
    an implant comprising a plug portion and a fastening portion separated by the same distance as in the trajectory control tool, wherein the fastening portion includes a bore with a countersunk portion for mating with a head of a screw and the plug portion includes a closeable cap.

2. The surgical system of claim 1 wherein the trajectory has a compound angle according to a cranio-caudal axis and a medial lateral axis with respect to a reference plane tangential to the access channel entry on the anterior surface of the vertebral body.

3. The surgical system of claim 1 wherein the trajectory control sleeve includes a contact surface for engaging a corresponding surface on the bone cutting tool, the surfaces configured so as to limit the penetration of the cutting tool into the vertebral body to a prescribed depth.

4. The surgical system of claim 1, wherein the plug portion of the implant comprises a porous cage with a porosity sufficient to permit through movement of blood and bone cells.

5. The surgical system of claim 4, wherein the porous cage is configured to allow bone material to be placed in the cage and be in intimate contact with an interior surface of the access channel.

6. The surgical system of claim 4 wherein the porous cage is integrally formed with a plate portion of the implant, the plate portion being configured to contact the anterior surface of the vertebral body.

7. The surgical system of claim 4 wherein the composition of the porous cage comprises any of a polymer, a metal, metallic alloy, or a ceramic.

8. The surgical system of claim 7, wherein the polymer of the composition may include polyetheretherketone (PEEK), PEEK-reinforced carbon fiber, or hydroxyapatite-reinforced PEEK.

9. The surgical system of claim 4, wherein the porous cage includes a closeable opening through which bone material may be passed.

10. The surgical system of claim 4, wherein the porous cage includes the closeable cap, the closeable cap configured to increase pressure within the cage as the cap is closed.

11. The surgical system of claim 4, wherein the porous cage includes a minimally compressive internal element adapted to enhance compressive force applied to contents of the porous cage upon application of compressive force to the cage.

12. The surgical system of claim 1, wherein a posterior surface of the repair implant includes one or more penetrating elements configured to impinge into the vertebral bone tissue.

13. The surgical system of claim 1, wherein a posterior surface of the repair implant is of porous composition to support in-growth of bone.

14. The surgical system of claim 1, wherein the bone-cutting tool is any of a drill, a ream, a core cutter or a trephine.

15. The surgical system of claim 1, wherein a cutting element of the bone-cutting tool has a cutting diameter between about 5 mm and about 7 mm.

16. The surgical system of claim 1, wherein the plug portion of the repair implant has an external geometry complementary to the internal geometry of the access channel.

17. The surgical system of claim 1, wherein the repair implant includes an osteogenic agent.

18. The surgical system of claim 1, wherein the fastening portion of the trajectory control tool comprises a sleeve configured to removably receive an elongated fastening element for securing the tool to the vertebral body.

19. The surgical system of claim 18, further comprising an elongated fastening element having a proximal end and a distal end, the distal end being configured to thread into the vertebral body, the fastening element having a length sufficient to extend the proximal end outside of a patient when the distal end is threaded into the vertebral body.

* * * * *